United States Patent
Teh et al.

(10) Patent No.: US 10,378,062 B2
(45) Date of Patent: Aug. 13, 2019

(54) NATURAL-KILLER/T-CELL LYMPHOMA (NKTCL) SUSCEPTIBILITY PREDICTION, DIAGNOSIS AND THERAPY

(71) Applicant: SINGAPORE HEALTH SERVICES PTE LTD, Singapore (SG)

(72) Inventors: Bin Tean Teh, Singapore (SG); Soon Thye Lim, Bowyer Block (SG); Choon Kiat Ong, Singapore (SG)

(73) Assignee: SINGAPORE HEALTH SERVICES PTE LTD, Singapore (SG)

( * ) Notice: Subject to any disclaimer, the term of this patent is extended or adjusted under 35 U.S.C. 154(b) by 0 days.

(21) Appl. No.: 15/174,578

(22) Filed: Jun. 6, 2016

(65) Prior Publication Data
US 2017/0029899 A1 Feb. 2, 2017

Related U.S. Application Data

(63) Continuation of application No. 14/360,804, filed as application No. PCT/SG2012/000444 on Nov. 26, 2012, now abandoned.

(30) Foreign Application Priority Data

Nov. 25, 2011 (SG) .................................. 201108800

(51) Int. Cl.
| | | |
|---|---|---|
| C12Q 1/68 | (2018.01) | |
| C12Q 1/6886 | (2018.01) | |
| A61K 31/519 | (2006.01) | |
| G01N 33/50 | (2006.01) | |
| G01N 33/574 | (2006.01) | |
| A61K 31/277 | (2006.01) | |
| A61K 31/165 | (2006.01) | |
| A01K 67/027 | (2006.01) | |

(52) U.S. Cl.
CPC ........ *C12Q 1/6886* (2013.01); *A01K 67/0275* (2013.01); *A61K 31/165* (2013.01); *A61K 31/277* (2013.01); *A61K 31/519* (2013.01); *G01N 33/5011* (2013.01); *G01N 33/57407* (2013.01); *G01N 33/57426* (2013.01); *A01K 2267/0331* (2013.01); *C12Q 2600/156* (2013.01); *C12Q 2600/158* (2013.01); *G01N 2333/912* (2013.01); *G01N 2333/91215* (2013.01); *G01N 2800/50* (2013.01)

(58) Field of Classification Search
None
See application file for complete search history.

(56) References Cited

U.S. PATENT DOCUMENTS

2009/0285796 A1* 11/2009 Goss .................... C12N 9/1205
424/130.1

FOREIGN PATENT DOCUMENTS

WO 2001052892 A2 7/2001

OTHER PUBLICATIONS

Bouchekioua et al (Leukemia, 2014, 28: 338-348).*
Loong et al (Leukemia & Lymphoma, 2008, 49(6): 1161-1167).*
Campo et al. (2011) "The 2008 WHO classification of lymphoid neoplasms and beyond: evolving concepts and practical applications," Blood. 117(19):5019-5032.
Coppo et al. (2009) "STAT3 Transcription Factor is Constitutively Activated and is Oncogenic in Nasal-type NIQT-Cell Lymphoma," Leukemia. 23(9):1667-1678.
Cornejo et al. (2009) "Constitutive JAK3 Activation Induces Lymphoproliferative syndromes in Murine Bone Marrow Transplantation Models," Blood. 113(12):2746-2754.
Deutsche Sammlung Von Mikroorganismen Und Zellkulturen—German Collection of Microorganisms and Cell Cultures GmbH. DSMZ No. ACC 392.
Kiyoi et al. (2007) "JAK3 mutations occur in acute megakaryoblastic leukemia both in Down syndrome children and non-Down syndrome adults," Leukemia. 21:574-576.
Koo et al. (Jun. 15, 2012) "Janus kinase 3-activating Mutations Identified in Natural Killerff-cell Lymphoma," Cancer Discovery. 2(7):591-597.
Mella et al. (2001) "Eleven novel JAK3 mutations in patients with severe combined immunodeficiency-including the first patients with mutations in the kinase domain," Human Mutation. 18(4):355-356.
Percy et al. (2005) "The V617F JAK2 mutation and the myeloproliferative disorders," Hematological Oncology. 23(3-4):91-93.
Schumacher et al. (2000) "Complete genomic organization of the human JAK3 gene and mutation analysis in severe combined immunodeficiency by single-strand conformation polymorphism," Human Genetics. 106:73-79.
Tse et al. (2013) "How I treat NK/T-cell lymphomas," Blood. 121(25):4997-5005.
Tsutsui et al. (2009) "Frequent STAT3 Activation is Associated with Mcl-1 Expression in Nasal NK-cell Lymphoma," International Journal of Laboratory Hematology. 32(4):419-426.
Tyner et al. (2008) "RNAi screening of the tyrosine kinome identities therapeutic targets in acute myeloid leukemia," Blood. 111(4):2238-2245.
Wikipedia.org "Diagram showing the development of different blood cells from haematopoietic stem cell to mature cells," Wikimedia Foundation, Inc. Image accessible on the Internet at URL: https://upload.wikimedia.org/wikipedia/commons/f/f0/Hematopoiesis_simple.svg.

(Continued)

*Primary Examiner* — Sean E Aeder
(74) *Attorney, Agent, or Firm* — Lathrop Gage LLP; Brian C. Trinque

(57) ABSTRACT

Natural-KilleifT-Cell Lymphoma (NKTCL) susceptibility prediction, diagnosis and therapy. The invention relates to a method for predicting Natural Killer T-cell Lymphoma (NK-TCL) susceptibility and/or diagnosing NKTCL in a subject comprising testing for JAK mutations. The invention also relates to a method of screening for candidate agents capable of treating NKTCL using a cell line comprising at least one JAK mutation. The invention includes an NKTCL animal model comprising at least one JAK mutation. The invention also includes JAK inhibitors for treating NKTCL.

5 Claims, 5 Drawing Sheets
Specification includes a Sequence Listing.

(56) References Cited

OTHER PUBLICATIONS

International Search Report with Written Opinion corresponding to International Patent Application No. PCT/SG2012/000444, dated Apr. 30, 2013.

* cited by examiner

JAK3 Wild Type
T C A T T C C T G G A A G C A G C G A G C
c.1715 C

JAK3 A572V Heterozygous Mutant
T C A T T C C T G G A A G C A G C G A G C
c.1715 C>T JAK3 A573V Heterozygous Mutant
T C A T T C C T G G A A G C A G C G A G C
c.1718 C>T JAK3 A572V Homozygous Mutant
T C A T T C C T G G A A G T A G C G A G C
c.1715 C>T

*Fig. 2A*
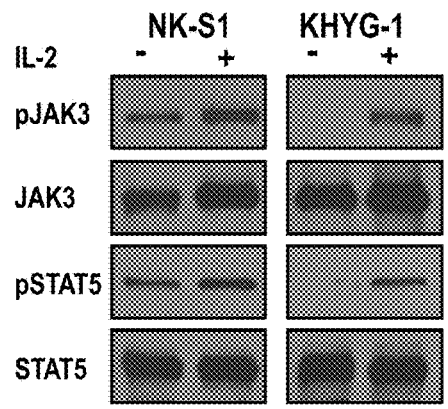
*Fig. 2B*
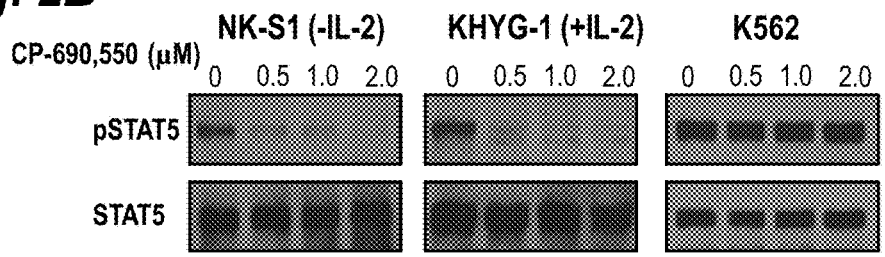
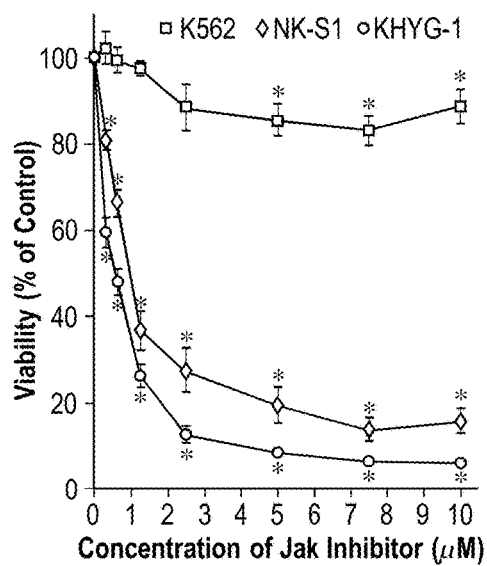
*Fig. 2C*
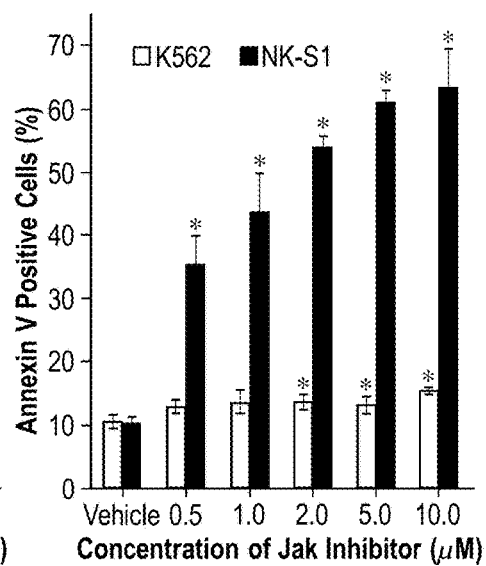
*Fig. 2D*

NATURAL-KILLER/T-CELL LYMPHOMA (NKTCL) SUSCEPTIBILITY PREDICTION, DIAGNOSIS AND THERAPY

RELATED APPLICATIONS

This application is a continuation of U.S. patent application Ser. No. 14/360,804, filed May 27, 2014, which is a 35 U.S.C. § 371 filing of International Application No. PCT/SG2012/000444, filed Nov. 26, 2012, which claims priority to Singapore Patent Application No. 201108800-2, filed Nov. 25, 2011, each of which is incorporated herein by reference in its entirety.

FIELD OF THE INVENTION

The present invention relates to cancer therapy and/or diagnosis. In particular, it relates to Natural-Killer/T-Cell Lymphoma (NKTCL) therapy and/or diagnosis.

BACKGROUND OF THE INVENTION

Natural killer (NK)-cell lymphoma is a type of non-Hodgkin lymphoma (NHL). Most NHLs (90%) are of B-cell origin. NK-cell lymphomas do not arise from B-cells. However, controversy still exists over the normal cell from which NK-cell lymphomas arise. In particular, whether NK-cell lymphoma represents the presence of a true NK cell or merely the presence of a T cell with abnormal cell markers is under debate. In the absence of unequivocal proof of the exact lineage of NK-cell lymphoma, many investigators prefer to use the term NK/T-cell lymphoma (NKTCL) when classifying this condition.

Natural-killer T-cell lymphoma (NKTCL) is particularly prevalent in Asian countries and some parts of Latin America. It accounts for up to half of all mature T cell lymphoma cases in Asia (1). However, compared to the more common B cell lymphomas, very little is known about its molecular characteristics and pathogenesis. There has been little progress in basic science and clinical research in this subtype of lymphoma, which continues to constitute a major challenge in managing these patients as there is currently no accepted standard first-line treatment for NKTCL. Despite multi-agent chemotherapy and involved-field radiotherapy, the 5-year overall survival is approximately 9% for non-nasal NKTCL and 42% for nasal NKTCL (2, 3).

Compared to B cell lymphomas which are relatively more common, very little is known about the molecular characteristics and pathogenesis of NKTCLs. This may be in part due to relative rarity in the West and difficulty in obtaining adequate biopsy. Treatment of NKTCLs with conventional chemotherapy has thus far yielded poor results and the outcome is almost always fatal for patients with stage III or IV disease.

It is desirable to identify novel genetic aberrations and potential treatment targets in NKTCL, as well as potential therapeutic agents for NKTCL.

SUMMARY OF THE INVENTION

The present invention relates to cancer therapy and/or diagnosis, in particular Natural-Killer/T-Cell Lymphoma (NKTCL) therapy and/or diagnosis.

According to a first aspect, the present invention relates to a method for predicting Natural Killer T-Cell Lymphoma (NKTCL) susceptibility and/or diagnosing NKTCL in a subject, comprising testing for the genotype of said subject for at least one JAK gene, wherein the presence of a mutant JAK gene indicates that a subject is at risk of developing and/or has NKTCL.

The invention also relates to a method for predicting Natural Killer T-Cell Lymphoma (NKTCL) susceptibility and/or diagnosing NKTCL in a subject, comprising testing for whether said subject expresses a wildtype or mutant JAK protein, wherein expression of a mutant JAK protein indicates that the subject is at risk of developing and/or has NKTCL.

According to a second aspect, the invention relates to a method for screening for an agent capable of treating NKTCL, comprising:
(i) providing a NKTCL cell line comprising at least one mutant JAK gene;
(ii) contacting the NKTCL cell line with the agent; and
(iii) determining the effect of the agent on the mammalian NKTCL cell line;
wherein the ability of the agent to reduce the viability, growth and/or multiplication and/or increase apoptosis of the NKTCL cell line is indicative of the ability of the agent to treat NKTCL.

According to a third aspect, the invention relates to a method for screening for an agent capable of reducing the activity of at least one of JAK protein, comprising:
(i) providing a NKTCL cell line carrying a mutant JAK gene;
(ii) contacting the NKTCL cell line with the agent; and
(iii) determining the effect of the agent on the NKTCL cell line;
wherein the ability of the agent to reduce the viability, growth and/or multiplication and/or increase apoptosis of is indicative of the ability of the candidate agent to reduce the activity of at least one JAK protein.

According to a fourth aspect, there is provided an NKTCL animal model comprising at least one mutant JAK gene.

According to a fifth aspect, the invention relates to a method of treating Natural Killer T-Cell Lymphoma (NKTCL) comprising administering a JAK inhibitor to a subject.

The invention also includes use of a JAK inhibitor in the preparation of a medicament for the treatment of Natural Killer T-Cell Lymphoma (NKTCL).

The invention further includes a JAK inhibitor for use in treating Natural Killer T-Cell Lymphoma (NKTCL).

BRIEF DESCRIPTION OF THE FIGURES

FIG. 1A shows the location of the A572V and A573V mutation on the JH2 pseudokinase domain of the JAK3 gene. High-resolution melt (HRM) and Sanger sequencing data used to validate JAK3 mutations are shown in FIG. 1B through FIG. 1H. In particular: FIG. 1B shows the percentage of the JAK3 A572V and A573V mutations in the pie chart (n=65). FIG. 1C shows HRM difference plots (in replicates) normalized to the wild-type sample for three genotypes: wild-type JAK3, heterozygous JAK3 (c.1715C>T, p.Ala572Val) and homozygous JAK3 (c.1715C>T, p.Ala572Val). FIG. 1D shows representative HRM difference curves of an Formalin-Fixed Paraffin-Embedded (FFPE) NKTCL sample which was sequenced and confirmed as heterozygous JAK3 (c.1718C>T, p.Ala573Val) mutation. Notably, HRM difference plots for sample with either JAK3 A572V or A573V mutation were similar due to the same C>T conversion.

Figure 1A:
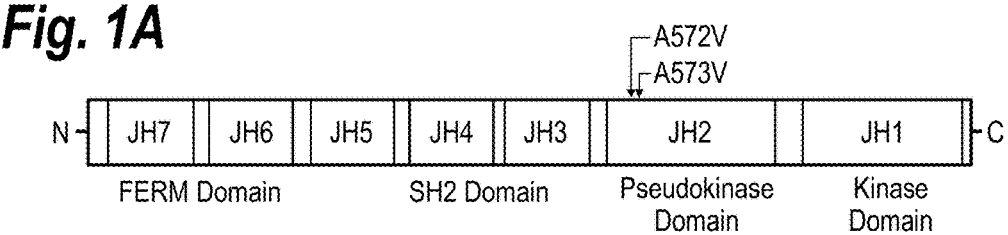
FIGS. 1A-1H show High-resolution melt (HRM) and Sanger sequencing data leading to the identification of JAK3 A572V and A573V mutations in NKTCL samples.
Figure 1B:
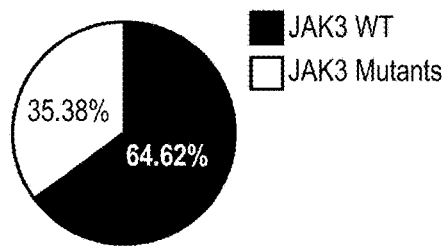
Figure 1C:
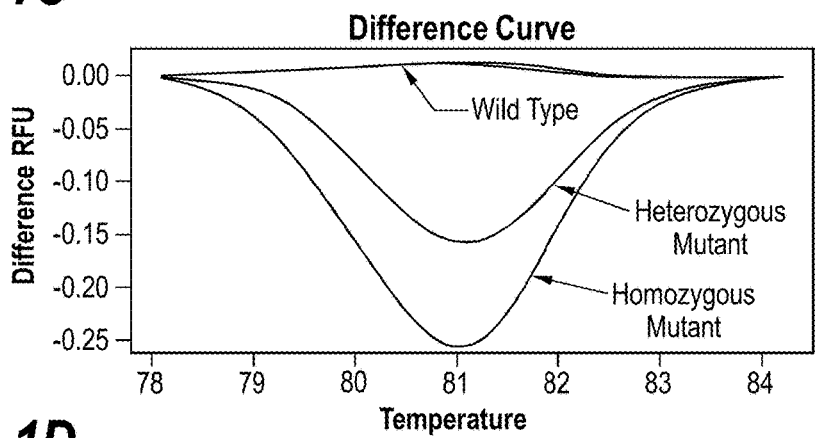
Figure 1D:
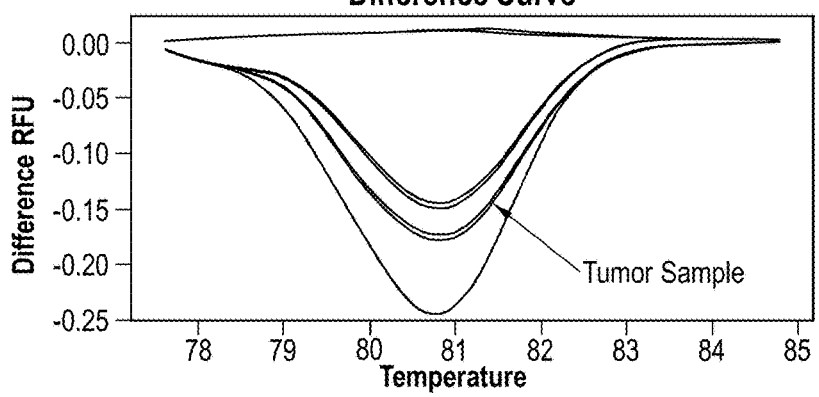
Figure 1E:
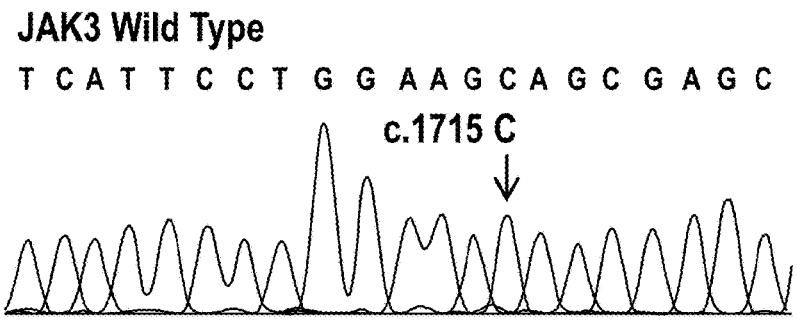
Figure 1F:
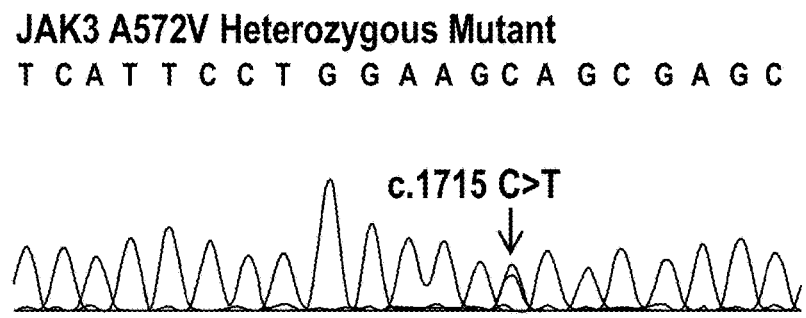
Figure 1G:
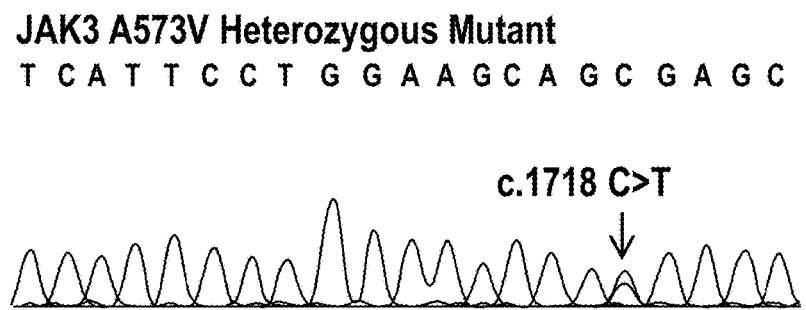
Figure 1H:
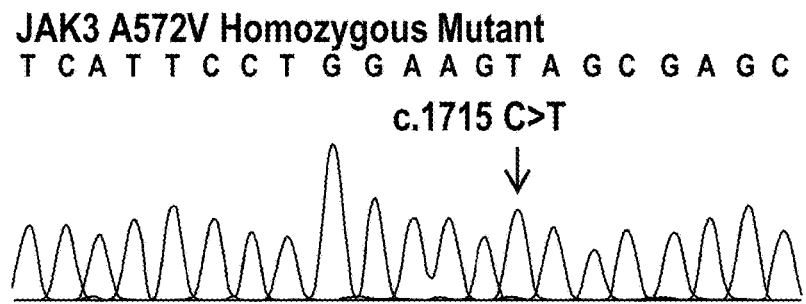

Representative sequencing chromatograms are also shown in FIG. 1E for the JAK3 wild-type allele, FIG. 1F for the A572V heterozygous mutant, FIG. 1G for the A573V heterozygous mutant, and FIG. 1H for the A572V homozygous mutant.

FIGS. 2A-2D show data demonstrating the effect of IL-2 on JAK3 and STAT5 phosphorylation and CP-690,550 treatment on NKTCL cell lines. FIG. 2A shows immunoblotting results for NK-S1 (JAK-mutant) and KHYG-1 (wild-type) cells which were cultured with or without recombinant human IL-2 (200 IU/ml), harvested at 48 h, and assayed for JAK3 and STAT5 phosphorylation by immunoblotting. NK-S1, KHYG-1 and K562 (control) cell lines were treated with the pan-JAK inhibitor CP-690,550 and the results of evaluation are shown in FIG. 2B through FIG. 2D. FIG. 2B shows STAT5 phosphorylation in the samples evaluated by immunoblotting at 48 h. FIG. 2C shows cell viability analyzed by MTS assay at 72 h. FIG. 2D shows drug-induced apoptosis at 72 h evaluated by Annexin V-FITC staining and analyzed by flow cytometry. Experiments were repeated at least three times. Results in FIG. 2O and FIG. 2D represent the average of triplicates±s.e.m. *Indicates p<0.05 by paired Student's t-test.

Figure 3A:
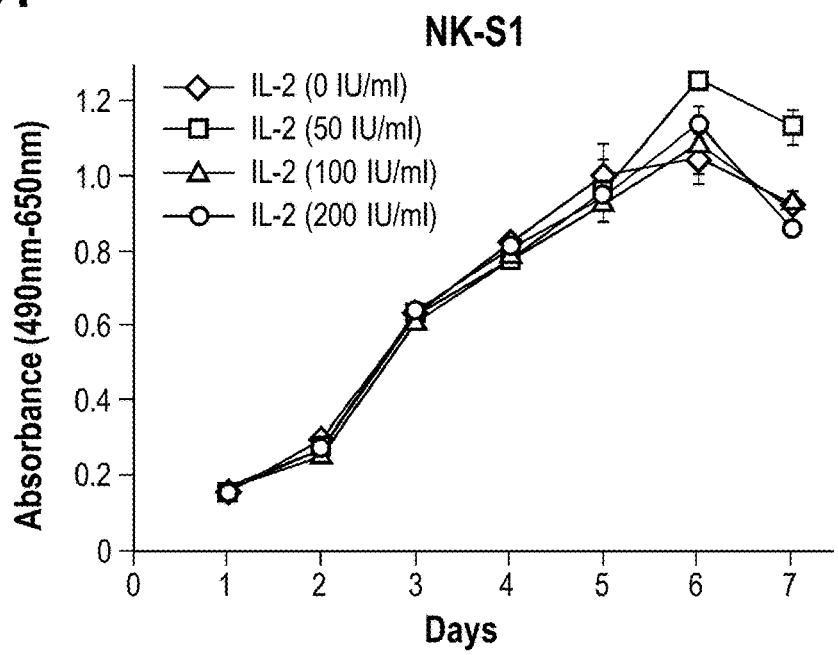
Figure 3B:
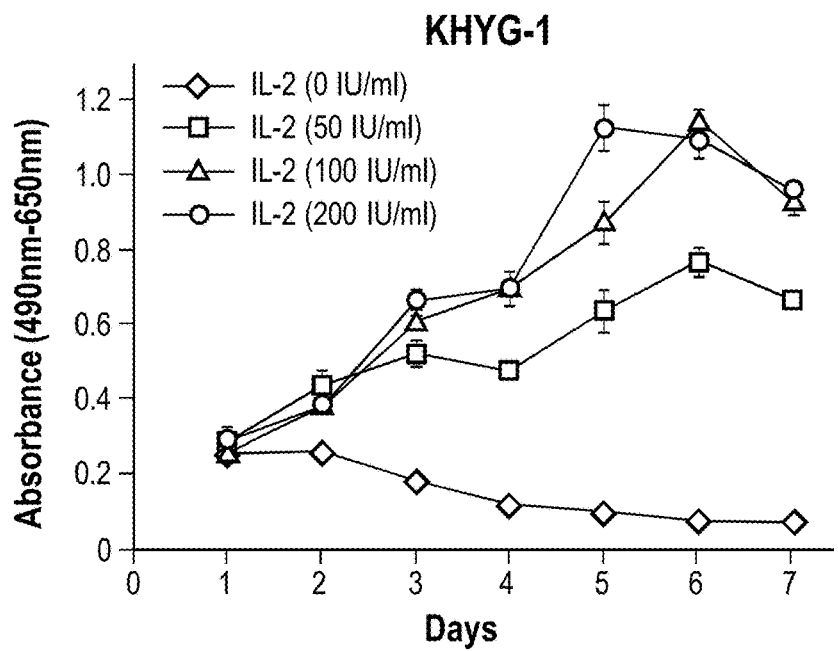

FIGS. 3A-3B provide data showing Cytokine independent growth of the mutant NKTCL cell line, NK-S1. In particular, NK-S1 (JAK3 mutant) and KHYG-1 (JAK3 wild-type) were cultured with or without recombinant human IL-2 (0 to 200 IU/ml). Cell viability data is shown in FIG. 3A for NK-S1 and in FIG. 3B for KHYG-1. Cell viability was monitored daily with MTS assay for seven days and cell growth was expressed as absorbance at 490 nm minus the reference at 650 nm. Results in FIG. 3A and FIG. 3B represent the average of triplicates±s.d.

Figure 4A:
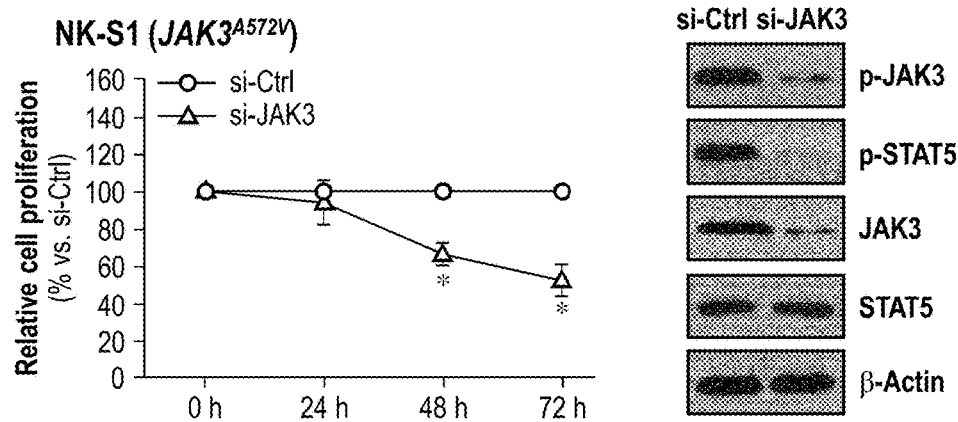
Figure 4B:
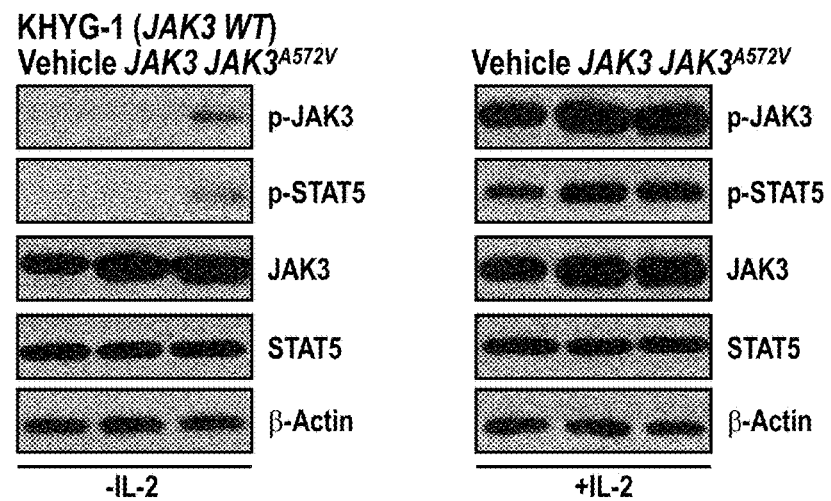
Figure 4B:
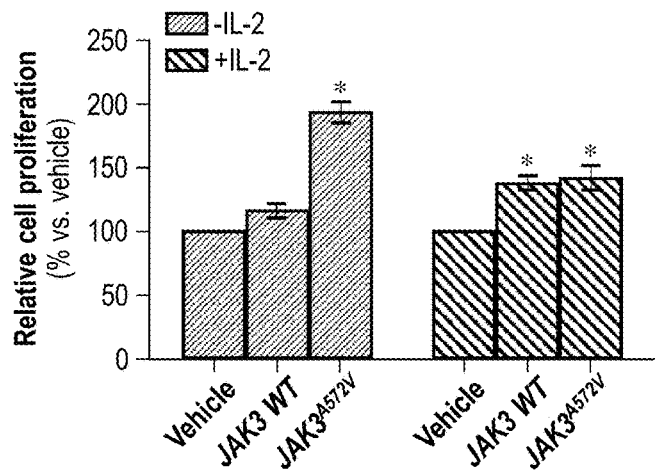

FIGS. 4A-4B show data demonstrating that JAK3 A572V mutation causes constitutive JAK3 activity and IL-2 independent proliferation of NKTCL cells. FIG. 4A shows data for NK-S1 cells which were treated with 100 nM JAK3 siRNA (si-JAK3) or control siRNA (si-Ctrl) for 24 h prior and subjected to proliferation assays up to 72 h (Right panel). In parallel, these cells were harvested and protein extracts were subjected to Western blotting with antibodies against phosphorylated JAK3 (pJAK3), phosphorylated STAT5 (pSTAT5), JAK3, STAT5, or β-actin as a normalization control. FIG. 4B shows data for KHYG-1 cells which were transiently transfected with wild-type JAK3 (JAK3 WT) or mutated JAK3 expression vectors (i.e. JAK3 A572V). The relative pJAK3, pSTAT5, JAK3 and STAT5 levels in these cells were detected by Western blotting (upper panel), and proliferation assays using these cells were performed for 48 h with or without IL-2 (lower panel). All results are expressed as mean SEM of three independent experiments. *, p<0.05 compared with Vehicle control (Vehicle).

DEFINITIONS

As used in the present specification, the term "inhibitor" refers to any substance which is able to reduce the activity of a protein, for example a JAK inhibitor is able to reduce the activity of a JAK protein. In particular, a JAK3 inhibitor is able to reduce the activity of a JAK3 protein. Reducing the activity of a protein may be direct or indirect—for example, by interfering with the expression of the protein or the mechanism by which the protein functions in a biological context. For example, the JAK3 kinase may require binding of a molecule of ATP to an ATP-binding site, so by specifically binding to and blocking the ATP-binding site, the activity of the JAK3 kinase is reduced. The activity of the JAK protein may also require the activity of another protein, such as a cytokine receptor, so interference with the activity of this protein may also reduce the activity of the JAK protein. Alternatively, fewer JAK3 kinase proteins may be expressed by interfering with gene expression at the relevant nucleic acid domain, such as the translation of the corresponding mRNA.

NKTCL refers to NK/T cell lymphoma in accordance with WHO classification (6). The terms "Natural Killer T-Cell Lymphoma," NKTCL and "NK/T-cell lymphoma" are used interchangeably to refer to a type of non-Hodgkin lymphoma (NHL) that is not of B-cell origin. NKTCL has the classic morphology of tumor necrosis, angiocentricity as well as the appropriate immunophenotype, in particular, presence of CD56, cytoplasmic CD3 as well as near universal presence of EBER. NK/T cell lymphoma differs from Adult T cell Leukemia/Lymphoma, which is a disease of the T cell lineage and associated with HTLV-I infection.

The term "treating" includes alleviating, preventing and/or eliminating one or more symptoms associated with a disease, for example Natural killer/T-cell Lymphoma (NKTCL)

DETAILED DESCRIPTION OF THE INVENTION

The present invention relates to cancer therapy and/or diagnosis, in particular Natural-Killer/T-Cell Lymphoma (NKTCL) therapy and/or diagnosis.

According to a first aspect, there is provided a method for predicting Natural Killer T-Cell Lymphoma (NKTCL) susceptibility and/or diagnosing NKTCL in a subject, comprising testing for the genotype of said subject for at least one JAK gene wherein the presence of a mutant JAK gene indicates that a subject is at risk of developing and/or has NKTCL. The presence of either a heterozygous or homozygous mutant JAK gene indicates that the subject is at risk of developing and/or has NKTCL.

Any one or a combination of any of the JAK genes may be tested. The JAK gene tested may be selected from the group consisting of JAK1, JAK2, JAK3 and TYK2. For example, the JAK3 and/or JAK1 genes may be tested. In general, SEQ ID NO: 1 indicates a wildtype JAK3 gene. In one example, the presence of a mutant JAK3 gene comprising a substitution of C with T at nucleotide 15792 and/or a substitution of C with T at nucleotide 15795 of SEQ ID NO: 1 indicates that a subject is at risk of developing and/or has NKTCL.

In general, SEQ ID NO: 3 indicates a wildtype JAK1 gene. In another example, the presence of a mutant JAK1 gene comprises a substitution of T with G at nucleotide 124823 of SEQ ID NO: 3 indicates that a subject is susceptible and/or has NKTCL. The presence of both mutant JAK1 and JAK3 genes also indicate that a subject is at risk of developing and/or has NKTCL.

The method may be performed on an isolated cell sample from the subject. The isolated cell sample may be from a blood and/or tumour sample. Accordingly, the method may further comprise providing an isolated cell sample from the subject for testing. The method may further comprise isolating nucleic acid molecules from the subject, blood sample and/or isolated cell sample for said testing. The isolated nucleic acid molecules may comprise genomic DNA or mRNA. In particular, the testing may be performed on genomic DNA, mRNA and/or cDNA.

Any suitable technique may be employed for testing. For example, testing may be by sequence analysis, restriction fragment length polymorphism analysis, hybridization, polymerase chain reaction (PCR) and/or reverse transcription PCR. In particular, techniques such as Sanger sequencing and High resolution melt may be used for testing.

In another aspect of the invention, there is provided a method for predicting Natural Killer T-Cell Lymphoma (NKTCL) susceptibility and/or diagnosing NKTCL in a subject, comprising testing for whether said subject expresses a wildtype or mutant JAK protein, wherein expression of a mutant JAK protein indicates that the subject is at risk of developing and/or has NKTCL.

Any one or a combination of any of the JAK proteins may be tested. The JAK protein tested may be selected from the group consisting of JAK1, JAK2, JAK3 and TYK2. For example, the JAK3 and/or JAK1 proteins may be tested. In general, SEQ ID NO: 2 indicates a wildtype JAK3 protein. In one example, the presence of a mutant JAK3 gene comprising a substitution of A with V at amino acid 572 and/or a substitution of A with V at amino acid 573 of SEQ ID NO: 2 indicates that a subject is at risk of developing and/or has NKTCL.

In general, SEQ ID NO: 4 indicates a wildtype JAK1 protein. In another example, the presence of a mutant JAK1 protein comprising a substitution of Y with D at amino acid 652 of SEQ ID NO: 4 indicates a subject at risk of developing and/or has NKTCL. The presence of both mutant JAK3 and JAK1 proteins also indicate a subject at risk of developing and/or has NKTCL.

The method may be performed on an isolated blood and/or cell sample from the subject. The isolated cell sample may be from a tumour. Accordingly, the method may further comprise providing an isolated blood and/or cell sample from the subject for testing. The method may further comprise isolating proteins molecules from the subject, blood sample and/or isolated cell sample for said testing.

Any suitable method may be used to detect whether the relevant wildtype and/or mutant JAK protein is expressed. For example, testing may be by protein sequencing and/or antibody detection. In particular, Enzyme-linked immunosorbent assay (ELISA) using at least one antibody with specificity for the relevant wildtype and/or mutant JAK protein may be used.

In a second aspect of the invention, there is provided a method for screening for an agent capable of treating NKTCL, comprising:
  (a) providing a NKTCL cell line comprising at least one mutant JAK gene;
  (b) contacting the NKTCL cell line with the agent; and
  (c) determining the effect of the agent on the NKTCL cell line;
wherein the ability of the agent to reduce the viability, growth and/or multiplication and/or increase apoptosis of the NKTCL cell line may be indicative of the ability of the agent to treat NKTCL.

In a third aspect of the invention, there is provided a method for screening for an agent capable of reducing the activity of at least one JAK protein, comprising:
  (i) providing a NKTCL cell line carrying at least one mutant JAK gene
  (ii) contacting the NKTCL cell line with the agent; and
  (iii) determining the effect of the agent on the NKTCL cell line;
    wherein the ability of the agent to reduce the viability, growth and/or multiplication and/or increase apoptosis of cell line is indicative of the ability of the candidate agent to reduce the activity of at least one JAK protein.

The NKTCL cell line may carry any one or a combination of any of mutant JAK1, JAK2, JAK3 or TYK2 genes. For example, the NKTCL cell line may carry a mutant JAK3 gene and/or a mutant JAK1 gene. In particular, the mammalian NKTCL cell line may carry at least one of the following mutations:
  (i) a substitution of C with T at nucleotide 15792 of SEQ ID NO:1 (in the JAK3 gene);
  (ii) a substitution of C with T at nucleotide 15795 of SEQ ID NO:1 (in the JAK3 gene); and
  (iii) a substitution of T with G at nucleotide 124823 of SEQ ID NO:3 (in the JAK1 gene).

According to a fourth aspect, the invention also relates to an NKTCL animal model comprising at least one mutant JAK gene. For example, the NKTCL animal model may comprise at least one mutation selected from the group consisting of mutant JAK1, JAK2, JAK3 and TYK2 genes. In particular, the NKTCL animal model comprises a mutant JAK3 gene and/or a mutant JAK1 gene. More in particular, the NKTCL animal model comprises at least one of the following mutations:
  (i) a substitution of C with T at nucleotide 15792 of SEQ ID NO: 1;
  (ii) a substitution of C with T at nucleotide 15795 of SEQ ID NO: 1; or
  (iii) a substitution of T with G at nucleotide 124823 of SEQ ID NO: 3.

The NKTCL animal model may also be useful for screening candidate agents capable of treating NKTCL.

According to a fifth aspect, there is provided a method of treating Natural Killer T-Cell Lymphoma (NKTCL) comprising administering at least one JAK inhibitor to a subject. Any suitable JAK inhibitor may be used. In another aspect of the invention, there is provided a use of at least one JAK inhibitor for the preparation of a medicament for the treatment of Natural Killer T-Cell Lymphoma (NKTCL). In another aspect of the invention, there is provided a JAK inhibitor for use in treating Natural Killer T-Cell Lymphoma (NKTCL). The JAK inhibitor may able to reduce the activity of JAK3 protein.

For example, the JAK inhibitor may inhibit at least one of JAK1, JAK2, JAK3 and/or TYK2. Accordingly, the inhibitor may be a pan-JAK inhibitor. In one particular example, the JAK inhibitor may inhibit JAK3 and/or JAK1. More in particular, the JAK inhibitor may inhibit JAK3 or the JAK inhibitor may also inhibit JAK1.

In a first particular example, the JAK inhibitor may comprise 3-[(3R,4R)-4-methyl-3-[methyl(7H-pyrrolo[2,3-d]pyrimidin-4-yl)amino]piperidin-1-yl]-3-oxopropanenitrile (also known as CP-690,550). In a second particular example, may comprise (E)-2-cyano-3-(4-nitrophenyl)-N—((R)-1-phenylethyl)acrylamide (also known as WP-1034).

The subject to whom the JAK inhibitor is administered may comprise a mammal. The subject may comprise a human. The subject may carry a homozygous or heterozygous mutation in at least one of the JAK genes/JAK proteins. For example, the subject may carry a homozygous or heterozygous mutation in JAK1/JAK1, JAK2/JAK2, JAK3/JAK3 and/or TYK2/TYK2. In particular, the subject may carry a homozygous or heterozygous mutation in JAK1/JAK1 and/or JAK3/JAK3. More in particular, the subject may have at least one mutation selected from the group consisting of JAK3-A572V, JAK3-A573V and JAK1-Y652D. However, the subject may also comprise a homozygous wildtype phenotype. The subject may have increased expression of any one of the JAK genes, its transcriptional and/or translational products (proteins), whether it carries a homozygous wildtype, heterozygous or homozygous mutant gene.

CP-690,550 is a JAK inhibitor. It is known as Tofacitinib, Tasocitinib, or by the trade name XELJANZ. Its chemical name is 3-[(3R,4R)-4-methyl-3-[methyl(7H-pyrrolo[2,3-d]pyrimidin-4-yl)amino]piperidin-1-yl]-3-oxopropanenitrile and its structural formula is:

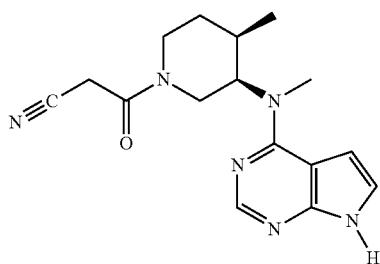 [SMILES: C[C@@H]1CCN(C(=O)CC#N)C[C@@H]1N(C)c1ncnc2[nH]ccc12]

WP-1034 has been described as having proapoptotic and antileukemic activity in Acute Myeloid Leukemia (Faderl et al., Anticancer Research 25: 1841-1850 (2005)) (8). It is a member of the tyrphostin family of tyrosine kinase inhibitors, which has been predominantly studied as an inhibitor of the Jak-Stat pathway. Its chemical structure and name are as follows:

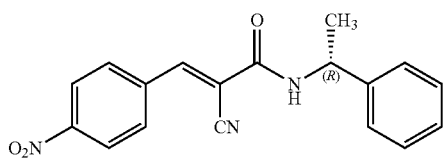

WP1034-(E)-2-cyano-3-(4-nitrophenyl)-N—((R)-1-phenylethyl)acrylamide

Having now generally described the invention, the same will be more readily understood through reference to the following examples which are provided by way of illustration, and are not intended to be limiting of the present invention.

EXAMPLES

The molecular pathogenesis of Natural-killer/T-cell lymphoma (NKTCL) is not well understood. Gene mutations causing NK/T-cell lymphoma have not been fully identified. In this study, Janus kinase 3 (JAK3) somatic activating mutations (A572V and A573V) were identified through whole-exome sequencing in two out of four NKTCL patients. Further validation of the prevalence of JAK3 mutations was determined by Sanger sequencing and High Resolution Melt (HRM) analysis in an additional 61 cases. In total, 23 of 65 (35.4%) cases harbored JAK3 mutations. Mutant NKTCL cell line harbouring JAK3 A572V mutation showed IL-2 independent growth and constitutive JAK3 and STAT5 phosphorylation suggesting its oncogenic role. Functional characterization of the JAK3 mutations support its involvement in cytokine-independent JAK/STAT constitutive activation leading to increased cell growth. These mutations may play a significant role in the pathogenesis of NKTCL. Moreover, treatment of both JAK3-mutant and wild-type NKTCL cell lines with a novel pan-JAK inhibitor, CP-690,550, resulted in dose dependent reduction of phosphorylated STAT5, reduced cell viability and increased apoptosis. CP-690,550 is a pan-JAK inhibitor, having an inhibitory effect on not just JAK3 but also JAK1. This may be important because in their function within the JAK-STAT signalling pathway system, JAK1 and JAK3 cross-talk and there may be some compensatory upregulation of one in response to inhibition of the other. For example, if JAK3 is inhibited, JAK1 may be upregulated so as to compensate for the reduced activity of JAK3, and this may preserve JAK-STAT signalling. The reverse may also apply. To take the example further, treatment of NKTCL using a pan-JAK inhibitor that is able to reduce the activity of not just JAK1 but JAK3 as well may be especially effective at inhibiting JAK-STAT signalling.

Hence, targeting the deregulated JAK/STAT pathway could be a promising therapy for NKTCL patients. These findings have important implications for the management of NKTCL patients.

Materials and Methods

Tissue Samples

Matched fresh-frozen tissue and peripheral blood samples were obtained from four consented patients with NKTCL. The inventors further identified paraffin-embedded tissue blocks from 61 patients with NKTCL for validation. The diagnosis of NKTCL was made according to the 2008 World Health Organization (WHO) classification of tumors of the hematopoietic and lymphoid tissues (6). All samples were centrally reviewed by Singhealth hematopathologists. This study was approved by the SingHealth Centralized Institutional Review Board, Singapore.

DNA Isolation

DNA of frozen tissue and paired blood samples was isolated using a DNeasy Blood and Tissue Mini Kit (Qiagen) and a QIAmp DNA Blood Midi Kit (Qiagen), respectively, according to manufacturer's instruction. For Formalin-Fixed Paraffin-Embedded (FFPE) samples, genomic DNA was extracted from one or two 10-μM slices from each sample, paraffin was removed by xylene, tissues were washed twice with 100% ethanol, followed by overnight proteinase K digestion. DNA was then extracted using a DNeasy Blood and Tissue Mini Kit (Qiagen).

Detection of Somatic Mutations in Janus Kinases

Genomic DNA of extracted from each sample was whole genome amplified with REPLI-g WGA Midi Kit (Qiagen). The coding exonic sequences of JAK1, JAK2, JAK3 and Tyk2 were sequenced by Sanger sequencing to detect mutations. Somatic origin of the mutations were confirmed when the mutations were only detected in the tumor but not in the paired blood sample.

The mutation sequence information is provided below in Table 1 and in the accompanying genomic DNA, protein and cDNA sequence listings (SEQ ID No.:1 to SEQ ID No.:6), with the following sequence identifiers:

SEQ ID NO: 1—JAK3 Wildtype genomic DNA
SEQ ID NO: 2—JAK3 Wildtype amino acid sequence
SEQ ID NO: 3—JAK1 Wildtype genomic DNA
SEQ ID NO: 4—JAK3 Wildtype genomic sequence
SEQ ID NO: 5—JAK3 Wildtype cDNA
SEQ ID NO: 6—JAK1 Wildtype cDNA

TABLE 1

JAK1 and JAK3 Mutation Information

| | Protein | ORF[1] | cDNA | Gene |
|---|---|---|---|---|
| JAK1 | Y652D[6] | T1954G | T2203G[2] | T124823G[4] |
| JAK3 | A572V[7] | C1715T | C1815T[3] | C15792T[5] |
| JAK3 | A573V[7] | C1718T | C1818T[3] | C15795T[5] |

Notes on Table 1:
[1]ORF: Open reading frame, coding region, starts from ATG
[2]NCBI Reference Sequence: NM_002227.2 (SEQ ID NO: 6)
[3]NCBI Reference Sequence: NM_000215.3 (SEQ ID NO: 5)
[4]NCBI Reference Sequence: NG_023402.1 (SEQ ID NO: 3)
[5]NCBI Reference Sequence: NG_007273.1 (SEQ ID NO: 1)
[6]NCBI Reference Sequence: NP_002218.2 (SEQ ID NO: 4)
[7]GenBank: AA050950.1 (SEQ ID NO: 2)

Mutation Validation Using High-Resolution Melt (HRM) and Bi-Directional Sanger Sequence Analysis High-resolution melt (HRM) and Sanger sequencing were used to confirm the JAK1 and JAK3 mutations and validate their prevalence in the NKTCL patient population. Combining both methods will greatly improve the precision of mutation detection in FFPE samples. The JAK2 V617F mutation was also sequenced with both methods. The sequences of primer sets used for validation are listed in Table 2 (see below) and included in the accompanying sequence listings under the corresponding identifiers.

TABLE 2

Validation Primer Sets Used for Sanger Sequencing and HRM Analyses

| Primer Name | Primer Sequence (5' to 3') | Detection Method/Product Size | Sequence Identifier |
|---|---|---|---|
| JAK1_Seq_Exon14F | CTGGCCTGAGACATTCCTATG | Sanger Sequencing/144 bp | SEQ ID NO.: 7 |
| JAK1_Seq_Exon14R | TGAAAGAGAACACACTTACTCTCCAC | | SEQ ID NO.: 8 |
| JAK1_HRM_Exon14F | GCATGATGAGACAGGTCTCCCAC | HRM/83 bp | SEQ ID NO.: 9 |
| JAK1_HRM_Exon14R | GAGAACACACTTACTCTCCACGTC | | SEQ ID NO.: 10 |
| JAK2_Seq_Exon12F | CAGCAAGTATGATGAGCAAGC | Sanger Sequencing/121 bp | SEQ ID NO.: 11 |
| JAK2_Seq_Exon12R | ACAGATGCTCTGAGAAAGGC | | SEQ ID NO.: 12 |
| JAK2_HRM_Exon12F | GCTTTCTCACAAGCATTTGG | HRM/85 bp | SEQ ID NO.: 13 |
| JAK2_HRM_Exon12R | GGCATTAGAAAGCCTGTAGT | | SEQ ID NO.: 14 |
| JAK3_Seq_Exon12F | GCAGGTCTGTGAGCACAAAAT | Sanger Sequencing/167 bp | SEQ ID NO.: 15 |
| JAK3_Seq_Exon12R | ACTGTCTCCAGCCATGCAC | | SEQ ID NO.: 16 |
| JAK3_HRM_Exon12F | CCACCTTCCCCAGTCATTC | HRM/64 bp | SEQ ID NO.: 17 |
| JAK3_HRM_Exon12R | GAGATGCCGGTACGACACTTG | | SEQ ID NO.: 18 |

HRM Curve Analysis was used to discern the presence of the point mutations. SsoFast™EvaGreen Supermix® (Bio Rad, Cat. No. 172-5200) was used for amplification of target DNA fragments encompassing the relevant mutations from genomic DNA samples. HRM primers were used at a final concentration of 600 nM and reactions were performed with BioRad CFX96 Real time PCR Detection System in replicates. The cycling and melting conditions were as follows: one cycle of 98° C. for 2 min; 39 cycles of 98° C. for 5 sec, 58° C. for 10 sec; one cycle of 95° C. for 30 min and a melt from 72° C. to 95° C. rising at 0.2° C./sec. The HRM curves were analyzed with the Biorad Precision Melt Analysis™ software. HRM difference curves deviating from the wild-type curve were considered to be harbouring a mutation.

For Sanger sequencing, PCR was performed with Invitrogen Platinum Taq Polymerase (Cat. No. 10966-083) and cycled at 95° C. for 10 min; 39 cycles of 95° C. for 30 sec; 60° C. for 30 sec, 72° C. for 1 minute and a final extension of 72° C. for 10 min. Sequencing PCR was performed with ABI BigDye Terminator v3.1 (Cat. No. 4337457) and cycled at 96° C. for 1 min; 29 cycles of 96° C. for 10 sec; 50° C. for 5 sec & 60° C. for 4 min. The resulting products were run on ABI 3730 DNA Analyzer.

Cell Lines, Cell Viability and Apoptosis Assays

NK-S1 is a cell line established from a previously described NKTCL xenograft(7). The xenograft was derived from metastatic tumor of the testis from the same patient found to have both JAK1 (Y652D) and JAK3 (A572V) mutations. NK-S1 was cultured for more than 60 passages in DMEM medium supplemented with antibiotics, heat-inactivated FBS (10%) and equine serum (ES) (10%). Phenotypic analysis showed surface CD3−CD56+, and Granzyme B+ by intracellular staining. NK-S1 NKTCL cell line was sequenced and confirmed to carry homozygous mutation for JAK3 A572V, as well as a mutation on JAK1 codon 652. KHYG-1 is an IL-2 dependent aggressive NK leukemia cell line obtained from the Japanese Collection of Research Bioresources, and it was cultured in RPMI medium supplemented with antibiotics, heat-inactivated FBS (10%), ES (10%) and 200 IU/ml of recombinant human IL-2 (Proleukin, Novartis)[7]. KHYG-1 was sequenced and found to be wild-type for JAK3 codon 572 and 573, and JAK1 codon 652 and 658. K562 (CCL-234, ATC) is a chronic myeloid leukemia (CML) cell line positive for the BCR-ABL fusion gene.

To study the sensitivity of NKTCL cell lines to CP-690, 550 (Selleck Chemical, Cat. No. S5001), a pan-JAK inhibitor, cells were seeded at $2 \times 10^4$ cells/100 μL/well in 96-well plates and treated with CP-690,550 at various concentrations or with vehicle control. The viability was evaluated by MTS assay using a CellTiter 96® AQueous Non-Radioactive Cell Proliferation Assay Kit (Promega), absorbance was read at both 490 nm and 650 nm (as reference). The extent of drug-induced apoptosis was evaluated by Annexin V-FITC (BD Biosciences) staining. Acquisition of the data was performed on a FACSCalibur flow cytometer (BD Biosciences).

Immunoblotting

Cells were harvested at indicated time intervals after incubation with or without recombinant human IL-2 (Proleukin, Novartis), or in the presence or absence of CP-690, 550. Cells were washed with ice-cold phosphate buffer saline (PBS) and lysed in 50 μl of ice-cold RIPA buffer [25 mM Tris-HCL, pH 7.6, 150 mM NaCl, 1% Nonidet P-40, 1% sodium deoxycholate, 0.1% SDS, 1× Phosphatase Inhibitor (Cat. No. 78420, Thermo Fisher Scientific), 1× Protease Inhibitor (Cat. No. 12978000, Roche Diagnostics) and 1 mM Sodium Orthovanadate]. Thereafter, cell lysates were sonicated twice on ice for 10 seconds, 20 Amp and agitated on ice for another 15 minutes. After centrifugation at 14,000 g for 15 minutes at 4° C., supernatants were removed and protein concentration was determined using Bio-Rad Protein assay (Cat. No. 500-0006, Bio-Rad Laboratories). Protein samples were separated on a 5% stacking and 8% resolving SDS-polyacrylamide gel using Mini-PROTEAN Tetra Electrophoresis System (Cat. No. 165-8006, Bio-Rad Laboratories) and transferred onto 0.45 μM nitrocellulose membrane (Cat No. 162-0115, Bio-Rad Laboratories) using Mini Trans-blot Electrophoretic Transfer Cell (Cat. No. 170-3930EDU, Bio-Rad Laboratories) at 100V for 120 minutes. Membranes were blocked with 5% Milk in PBST, followed by overnight incubation of rabbit anti-phospho-jak1 (Tyr 1022/1023) (Cat. No. 3331, Cell Signaling), rabbit anti-phospho-JAK3 (Tyr 980/981) (D44E3) (Cat. No. 5031, Cell Signaling), mouse anti-Phospho-5tat5 (Tyr 694) (Cat No. 9356, Cell Signaling) and rabbit anti-phospho-stat3 (Tyr 705) (D3A7) (Cat. No. 9145, Cell Signaling) in 5% BSA and 5 mM sodium orthovanadate in PBST. were visualized using enhanced chemiluminescence (ECL) (Cat. No. 3407, Thermo Fisher Scientific, and Cat. No. RPN 2132, Amersham). Antibody for Jak1 (6G4) (Cat. No. 3344, Cell Signaling), Jak3 (Cat. No. 3775, Cell Signaling), Stat5 (Cat. No. 9363, Cell Signaling) and β-actin (Cat. No. A1978, Sigma) were used to detect unphosphorylated proteins or as a loading control. All antibodies were used at the recommended dilutions.

Results

Sanger sequencing was used to sequence the exonic regions of JAK1, JAK2, JAK3 and Tyk2 in fresh frozen tumor and blood specimens from four patients with Extra nodal NKTCL. Two JAK3 mutations, A572V (p.Ala572Val, c.1715C>T) and A573V (p.Ala573Val, c.1718C>T), and a novel JAK1 mutation, Y652D (p.Tyr652Asp, c.19541>G) were identified. Interestingly, JAK3 A572V and JAK1 Y652D mutations were found on the same sample. Both JAK3 mutations are both located at exon 12 on the JH2 pseudokinase domain (FIG. 1A), which is known to have an auto-inhibitory effect on the JH1 kinase domain. All three missense mutations identified in JAK1 and JAK3 were confirmed to be somatic in origin and predicted by Polyphen to be probably damaging.

Mutations identified were validated in FFPE samples of additional 61 patients with ENKTCL to confirm their prevalence. From this validation study, another 21 patients with JAK3 mutations were identified by Sanger sequencing. In total, out of 65 NKTCL patients 23 patients (35.4%) were found with JAK3 mutations (FIG. 1B). High Resolution Melt (HRM) analysis was performed on 40 FFPE samples and 14 JAK3 mutants were detected (35%). Amongst the 23 patients with JAK3 mutations, there were 17 heterozygous A572V, two homozygous A572V, two heterozygous A573V mutants, one homozygous A573V mutant and one patient had both an A572V and A573V heterozygous mutations (FIG. 1C-FIG. 1H). No additional JAK1 Y652D mutant was found, in addition, no patients were found with the JAK2 V617F (p.Val617Phe or c.1849> T) mutation, which is recently found to be present in a large proportion of patients with classic BCR/ABL-negative chronic myeloproliferative disorders and several patients with other clonal hematological cancers such as myelodysplastic syndrome and acute myeloid leukemia.

Discussion $JAK3^{A572V}$ Activating Mutations Confer Cytokine Independent Growth IL-2 is an essential cytokine required for the proliferation and activation of NK cells (4). JAK1 and JAK3 mediate IL-2 receptor signaling through phosphorylation of STAT transcription factors (5). In line with the functional importance of the activating JAK3 mutations identified, we tested if JAK3 mutations could confer IL-2 independent growth to the NKTCL cell line (NK-S1) that harbors a homozygous $JAK3^{A572V}$ mutation. JAK-mutant (NK-S1) cells showed IL-2 independent growth (FIG. 3A-FIG. 3B) and constitutive phosphorylation of both JAK3 and STAT5 (FIG. 2A). In contrast, JAK3-wild type KHYG-1 cells were clearly IL-2 dependent (FIG. 3A-FIG. 3B and FIG. 2A). Importantly, NK-S1 cells treated with JAK3 siRNAs exhibited a significant reduction in cell proliferation and also decreased autophosphorylation of JAK3 and STAT5, compared with cells treated with control siRNAs (FIG. 4A). Reciprocally, KHYG-1 cells transiently over-expressing a mutated JAK3 ($JAK3^{A572V}$) cDNA demonstrated IL-2 independent proliferation and autophosphorylation of JAK3 and STAT5 (FIG. 4B). These results indicate that the JAK3 activating mutations are gain of function alleles and contribute to the constitutive activity of the JAK/STAT pathway in an IL-2 independent manner.

This study demonstrated that JAK mutations confers cytokine independent growth in a NKTCL cell line established from xenograft derived from patient sample harboring both JAK3 A572V and JAK1 Y652D mutation. NK-S1 showed IL-2 independent growth (FIG. 3A-FIG. 3B), constitutive JAK3 and STAT5 phosphorylation (FIG. 2A) in contrast to the wild-type KHYG-1, which was tested not to carry JAK1 and JAK3 mutations identified (FIG. 2A).

Effects of CP-690,550 on NKTCL Cell Lines

The ability of CP-690,550, a pan-JAK inhibitor, to suppress the JAK-STAT pathway, was evaluated. Because activated JAK proteins directly phosphorylate STAT proteins, the JAK-mutated cell line (NK-S1) and the wild-type NKTCL cell line (KHYG-1) were treated with increasing concentrations of CP-690,550 and analyzed the pSTAT5 by immunoblotting (FIG. 2B). Both the NK-S1 and KHYG-1 cell lines showed a dose-dependent reduction of pSTAT5 (FIG. 2A) and reduced cell viability (FIG. 2B) upon treatment with the inhibitor. CP-690,550 did not inhibit pSTAT5 in the control K562 cell lines since its STAT5 phosphorylation is independent of activated JAK3 (FIG. 2B). The reduced viability of NK-S1 correlated with increased apoptosis as shown by Annexin V staining (FIG. 2C).

In summary, through exonic sequencing of Janus kinases (JAK) of Natural-killer/T-cell lymphoma (NKTCL) JAK3 A572 and A573V and JAK1 Y652D mutations have been identified in NKTCL patients, and the prevalence of JAK3 mutations was validated to be 35.4%. A mutant NKTCL cell line harboring JAK3 A572V mutation showed IL-2 independent growth and constitutive JAK3 and STAT5 phosphorylation suggesting an oncogenic role for mutations in the corresponding nucleic acid domain. In vitro study suggests that pan-Jak inhibitor could be a new therapeutic agent for NKTCL patients. CP-690,550, a pan-JAK-inhibitor, was shown to reduce cell viability and cause apoptosis in both JAK3 wild-type (KHYG-1) and mutant (NK-S1) cell lines. KHYG-1 is an IL-2 dependent NKTCL cell line, thus its sensitivity to pan-JAK inhibitor.

REFERENCES

1. Kwong Y L, Anderson B O, Advani R, Kim W S, Levine A M, Lim S T. Management of T-cell and natural-killer-cell neoplasms in Asia: consensus statement from the Asian Oncology Summit 2009. *The lancet oncology* 2009; 10(11): 1093-1101.
2. Au W Y, Ma S Y, Chim C S, Choy C, Loong F, Lie A K et al. Clinicopathologic features and treatment outcome of mature T-cell and natural killer-cell lymphomas diagnosed according to the World Health Organization classification scheme: a single center experience of 10 years. *Ann Oncol* 2005; 16(2): 206-214.
3. Vose J, Armitage J, Weisenburger D. International peripheral T-cell and natural killer/T-cell lymphoma study: pathology findings and clinical outcomes. *J Clin Oncol* 2008; 26(25): 4124-4130.
4. Suzuki R, Handa K, Itoh K, Kumagai K. Natural killer (NK) cells as a responder to interleukin 2 (IL 2). I. Proliferative response and establishment of cloned cells. *J Immunol* 1983; 130(2): 981-987.
5. Lu L, Zhu J, Zheng Z, Yan M, Xu W, Sun L et al. Jak-STAT pathway is involved in the induction of TNF-beta gene during stimulation by IL-2. *European journal of immunology* 1998; 28(3): 805-810.
6. Campo E, Swerdlow S H, Harris N L, Pileri S, Stein H, Jaffe E S. The 2008 WHO classification of lymphoid neoplasms and beyond: evolving concepts and practical applications. *Blood* 2008; 117(19): 5019-5032.
7. Loong S L, Hwang J S, Lim S T, Yap S P, Tao M, Chong T W et al. An Epstein-Barr virus positive natural killer lymphoma xenograft derived for drug testing. *Leukemia & lymphoma* 2008; 49(6): 1161-1167.
8. Faderl et al., WP-1034, a novel JAK-STAT inhibitor, with proapoptotic and antileukemic activity in acute myeloid leukemia (AML). *Anticancer Research* 25: 1841-1850 (2005).

The invention claimed is:

1. A method for screening for an agent capable of treating NKTCL, and reducing the activity of at least one JAK protein, the method comprising:
(i) providing a mammalian NKTCL cell line comprising a substitution of C with T at nucleotide 15792 of SEQ ID NO: 1; and a substitution of T with G at nucleotide 124823 of SEQ ID NO: 3;
(ii) contacting the mammalian NKTCL cell line with the agent without interleukin 2; and
(iii) determining an effect of the agent on the mammalian NKTCL cell line and JAK protein activity by measuring the viability, growth, apoptosis, and/or multiplication of the mammalian NKTCL cells, and the protein concentration of at least one JAK protein and/or phosphorylation of at least one JAK protein;
wherein the ability of the agent to reduce the viability, growth and/or multiplication and/or increase apoptosis of the mammalian NKTCL cell line and reduce the protein concentration of at least one JAK protein and/or phosphorylation of at least one JAK protein is indicative of the ability of the agent to treat NKTCL, and to reduce the activity of JAK protein.

2. The method according to claim 1, wherein the mammalian NKTCL cell line further carries a substitution of C with T at nucleotide 15795 of SEQ ID NO: 1.

3. The method according to claim 1, wherein the substitution of C with T at nucleotide 15792 of SEQ ID NO: 1 is homozygous.

4. The method according to claim 1, wherein the ability of the agent to reduce phosphorylation of JAK3 in the mammalian NKTCL cell line is indicative of the ability of the agent to treat NKTCL.

5. The method according to claim 4, wherein the further ability of the agent to reduce phosphorylation of STAT5 in the mammalian NKTCL cell line is indicative of the ability of the agent to treat NKTCL.

* * * * *

SEQUENCE LISTING

```
<160> NUMBER OF SEQ ID NOS: 18

<210> SEQ ID NO 1
<211> LENGTH: 28840
<212> TYPE: DNA
<213> ORGANISM: Homo sapiens

<400> SEQUENCE: 1
gtattttatc tttttcagtg ctgctgcaaa ggaaattttt caaaattttt ttatgttcca      60
attgtttgct gctggtgtat aaaaattcaa ttgactttg tattgaattc aacggacttt     120
ttaaacctgg taacttgctg aatttatgta ttaatttcag tagttgtctt atagattccc     180
ttgggttttt gacataaaca atcatatcat cagcaaatag caacagtttt atttaccttt     240 ttttattac ttatttatt ctgttttgct tgttacagaa tcttgctatg ttgcctttaa      300
attcttgggc tcccatttca gcttctccag tagctgaggc tacaagcatg tatcaccatg     360
cccagccaca cctgacttgt ttattttct catatatttt tttgttttaa gacaggatct     420
cgctctgttg cccagactgg agtgtaatgg tgtgatgatg gcttactgca gccttgtcct     480
ccctgactca agcaatcctc agcctcccaa atagctggga caacaggtgt gagctatcac     540
accctgccaa ttttaatt tttttttt tttgagacag agtctccctc tgtcacctag     600
gctggagtgc agtggcgcga tcttggctca ctgcaacctt cacctcccgg gttcaagcga     660
ttctcctgcc tcagcctcct gagtagctgg gattacaggc gcgcatcacc acgcacggct     720
aatttttgta ttttaccat gcctggctaa tttttgtatt tttagtagag atggggtttc     780
accatgttga tcaggctggt cttgaactcc tgaccttgtg attctcccac ctcagcctcc     840
caaagtgctg ggattacagg cgtgagccac catgcccagc ttttcttttc ttctttctt     900
```

```
tttttttttt tttagacgga gtctcactct gtcacccagg ctggagtgca gtggcccgat   960
cttggctcac tgcaagctcc gcctcccctgg ttcacaccat tctcctgcct cagcctgctt  1020
tttcttttct tattacagtg ctaacatca ccagaacaat gttgaataga ggtggtgaaa   1080
atggacatcc ttgtcttgtt tccaatctca ggaggaagtt attcagtctt ttaccatttt   1140
tgttttgtt tttgagatgt agtctcgctc tgtcgcccag gctggagtac agtggcacta   1200
tcttggctcc ctgcaacctc tgcctcctgg actcaagcca tcctcccact tcagtcttcc   1260
aagtagctga gactacaggt gcacaccacc atgcctggct aattttttgta tgttttgtag   1320
agacggatct caccatgttg cccaggctaa tctccaactc ctgagctcaa atgatcctcc   1380
catgttgact tcccaaagtg ctcagattac aggcatgagc caccgtgcct ggccctgcct   1440
cactgtactc ttaattttca tttggcaagt gaagctgagg aaattttct gggtttaaga   1500
gctatttgtc ctccatttc tctgacttct ggattcatat ccacctaact ggttggcatt   1560
ttcttactgc tttctagatg ttacttatat aacgaggata ttttatccat gagttcaatt   1620
ttgtttccag ttacactttg attgtatttt attctttgat tgtatttatg gacttcttgt   1680
cagcagaaaa atctgggtgt tgcatcact gacgtgcccc attttttctcg ggcaagttct   1740
gggttctgtc cccagaactt cctttttttta aaaaaaatta tttatttatt tatttattt   1800
ttgatacgga gtcttgctgt gtcgcccagg ctggagtgca gttgtgcgat ctcggctcac   1860
tgcaacctcc gcctcccagg ttcaagtgat tctcttgcct cagcctcctg agtagctggg   1920
actgcaggcg cccgccacca cacccagctg cgttttgtat ttttagtaga gatggggttt   1980
caccaggttg gcaaggccgg tctcgaactc ctaacctcag gcgatccgcc cgcctcggcc   2040
tcccaaagtg ctgggattat aggcgtgagc caccgcgccc ggccagaact tccttttaga   2100
gccttcacat gcccttctct ggggctgaag gtaccacttt ggtcctcacc ccaatctcct   2160
cttacttatt ctcaaaatat tgcagaaacc atcacactgg aggtagcaga gacccagaaa   2220
ctcactgtac ttccggaaag cagaggcttc agcctcaggc caaggatgag aacataaggt   2280
tgcattcccg tctgctgaag ccacccagga agtgaaagaa aacactacaa ctaagcttct   2340
gcttggcact tcctgccgca ggtcagctgt ggctccacta agctccacta agctgaggac   2400
ataatctata tctctttccc ttgacccacg cggccctacc cacgccatca atgagtctc   2460
agccccccgt gtccctgaca tcctgctctt tcaggaaca ctgtgaattc gtgaagcctc   2520
caggcctttg cctgggctgt tctgcctgcc agaactgccc acactccac attctcaggt   2580
cactctctgg ctagtcccac ttgttgttgg atttcagaat caaagccacc tcctccagga   2640
agccctccca gatccagtca tctctcttag cagaccggtc ccaggggcaa ctgatataat   2700
tattgggcaa tagcttgttt attgccatct cccctgctgg actgtcagct cccctggaca   2760
gggattgggt ctgcattgtc cccgattccc tgcacacagg ctgtgtccaa taagcctctg   2820
gctgattgaa cagttaagat caacaaaata cttaccaaac catttgtgt taagacttgt   2880
gatggtgata cagagatgaa aagtctttt ttttttttt ttgagacggg atctcactcc   2940
cattgcccag gctggagtgc agtggcatga ccacagctaa ctgcagcctc aacttcctgg   3000
gctcaggtga tcctcccacc tcagcctccc ctagtagctg ggactacagg cacatgccac   3060
cacatccagc ttattatttt gttgttgttg tatttttgt agagacaggg tttcaccatg   3120
ttgcccaggc tggtctcgaa cacctgggct caagccatcc tcctgcctga gcctcccaaa   3180
gtgctgagat tacaggtgtg agccactgtt cttggccaca acttcttaaa tctattcctt   3240
tttttttttt tgagacagag tattgctccg tcgcccaggc tggagtgcgg tggcacaatc   3300
```

-continued

```
tcagctcact acaacctccg cctgcctcct gggttccagt gattctcctg cctcagcctc    3360
ccaagtagct gggattacag gcacatgcca ccacgcccag ctaatttta tattttagt     3420 agagatgggg tttcaccatg ttggccaggc tggtctcgaa ctcctaggct caagcaatct    3480
tcccacctgg gccttccaaa gtgctggaat tacagatgtg agccactgta cccggtcacc    3540
acttcgtcag tctattcctg aagctctact tccggggctc tgatcctatt atcctaagaa    3600
cactggccca agtctctgca tttggatgct gcccgggcct tctgcctctt ctatttataa    3660
cagctcctac ttccaactct cctgtggctc cagattatgc tccaggcaaa acccacccctt   3720 ctcccaaaga ccctgatccc cctgtccccc cacgatcttg cccctgttga ccgccctgca    3780
gtccccttcc ccctcatctc acccctgccc ctggcctcct gactgctctt caagctgcta    3840
agatcactgc cctctcaagg tctttgccca tcctgtgccc cctcctgga gcacccttc     3900 cctggccagc tccctgtcct gcctcgggtc caagttccag tctgtgcctg tcctgacacc    3960 ctggcttttct ttgttgtctg cgatgatttg gctccttcat ttgctcattg tctcagcgcc   4020
agatcacaag ttccaagagg ccaggccgga tccacctggt tttttagggc tgggcccagg    4080
gcaccacagg cagaaatggg tcattatctc tccctgagtc ttttcttttt ttttaaacg     4140 aagtcccgct ctgttgccag gctggagtgc agtggcgcca tctcgtctca ctgtaacatc    4200
cgcctcctag attcaagcaa tcctcccacc tcagcctcct gagtagctag gattacaggc    4260
atcaccaggc ctggctaatt ttcctgtttt tagtagagac agggtttcat catgttggcc    4320
aggctggtct caaactcctg acttcaagtg atccgcccgc ctcagcctcc caaagtgctg    4380
cgattacagg ccaccacgcc tggctaattt ttgtatttt agtagagacg agtttcgcc     4440 atgttggcta ggctggtctc aaactcctga cctcaagtaa tcgcccgcct cagtctccca    4500
aagtgctggg atgacaggcg tgagccactg cgcccagcgt ctccctgagt cttaagggag    4560
aaatacctca aagaagaact tgaccttcct ctggggcaac ttccctgctt ccctcctggg    4620
caaatccagc caggtttcct tccctgggtg caaaattagt tccactgggt gcccaactca    4680
cacatgctac agatgggtaa actgaggcaa taagggccgg ccagagccc cacttaacaa     4740 gtgggtctag agtcggctga gcccctggtg tgacccagac ccttctctgt gctatcatca    4800
gttcctttgg cttaggggtc tccagcagcc tgtctgaacg gggcggctga tgcagaggct    4860
tccggaactt tctgccccctc cttgcccgcc tccccgcccc cagctcccgc agggccctga    4920
ctttcggtaa atgacagtgg ctcaggaaac caaggggccc acacaggaag gagccgagtg    4980
ggactttcct ctcgctgcct cccggctctg cccgcccttc gaaagtccag ggtccctgcc    5040
cgctaggtaa gagctggcga tgccgcaggg ctcggcccag acactggggg aggatggtgg    5100
tggcggggga tggctgggct ggggcagggt gctgccaggg caaaggctag ctcgccttcc    5160
aggcctcgga ggaaagctgc gaggcagacg tgagccgaga ctcgcatcct ccgatcgctc    5220
gcttctctgg gcttcggctt tgactaaggc cgggagatgc ctgccttgcg gacctggagg    5280
agtcattgcg catgcgcgac gggggctgcg gggttggggg tggggaggag ggattgggaa    5340
ggagggattg gggggcggag ttcccagccc ctaccctcca ggccttcccg gtccagacac    5400
agggtacccg accataccag gatgcagaac gttgaggatt ataaacaggg gatgccgagg    5460
cgggaggata gcttgaggcc aggagttcaa ggccagcctg gcaacatag ccagacctcc     5520 atttctacaa acattttaa aaaccaaaa aaactatggc gttttctggg accaaacatc      5580
acctctgact tttcattttt tttgttaca gtattacaga ataataatat tctgttaaga    5640
```

-continued

```
tttttttgtt gttttggaga tgggagtctt gctatgttgt tcaggcaggt ctctaacccc    5700
tggcctcaag ctatcctgct gcctcagccc cctgagtagc tgggattgca gtggggcgcc    5760
actgccactg aagccttatt ttaaactcga ctggggctgg gcacagtggc tcatgccttt    5820
aatcccaaca ctttgggagg ctgaggccag cggatcactg aggtcagga gttcgagatc    5880
agcctggtca acatggtgaa acccatctc tactaaaaac acaaaaatta gccaggtttg    5940
gtggcgggtg cctgtaattc cagctactca ggaggctgag gcaggagaat cgcttgaacc    6000
tgggaggtgg agtttgcagt gagccgagat catgccactg cactccagcc tgggagacag    6060
aacaagaatc cgtcctcccc cctacaaaat aaataaataa ataaaaaggc tgggcaatgt    6120
ggctcacgtg tgtaatcaca gcactttggg aggccaaggc aggcgaatca cctgaggcca    6180
ggagtttgag accagcctgg ccaacatggt gaaactccgt ctctactaaa aatacaaaaa    6240
ttagctgggc gctgtggtgc gcgcctgtaa tcccagccac ttgggaagct gaggcatgag    6300
aatcgcttga acccaggagg cagaggctac agtgagccaa gatcgtgcga ctgcactcca    6360
gcctgggtga cagtgcgaga ctccgtctca aaaaaacaaa caaacaaacc aaaaaacttg    6420
attggctgat gttgagggga cgatagagag gctatggtgt gtgattttat ttctataaag    6480
ggcaaaacta gacatcaatc tctctgtggg agagatgggg ctcctccaag gttcccggga    6540
ctaggaatgt gctcattctt ggtctgggca tcggtgacat caaagtgtcc ctttggtaag    6600
gttctttccc ccacaagact tcccttccca cagtaaccac cacaccgctg tgccaattgc    6660
ccttcctgtt tggtttaaca ggcgtttgtt gatcgcttac cggcacatca tcaagaaata    6720
tacaaattaa tgcacattaa ttgagttgac actttaggcc tggattgcgc tcagcagacc    6780
acctcaatga ggatgctggg gagtcagccc atttcacagc tgcgaaagct gagtcctagg    6840
ggtcctagtc ctctgattgt cttaaacctc attaggccag gcgcagtttc tcacgccggt    6900
aatcccagca ctttgggagt ccgaggcagg aggatcactc gaggtcagga gttccagacc    6960
agcctcgcca acatggtgaa accccgtctc taccaaaaat acaaaaatta gccgggcatg    7020
gtggcgtgcc cctgtaatcc cagctacttg ggaggctgag gcaggagaat cacttgaacc    7080
caggatgcag agtaagccga gattgtgcca ctgcactcca gcctggatga cagagctaga    7140
ctctgtctca aaacaaaaac aaaaaaaccc tcattaatgc cgccccaccc cagccacagg    7200
gcattatttt ggatcatagt ttttgtattg tgttttttt ctagagataa ggtcttgctc    7260
tgtcgcccag gctggagtgc agtggtgtga tcatagctca atgcagcctc aacttgcaga    7320
gctgaaggca tcctcctgtc tcagcctccc aagtagctag gactatgggg gtgtgccacc    7380
atgccctgct aattttttag agatgaggtc tcaaaatcct agcctcaagt gatccacctg    7440
cctcggcctg tcaaagtgct gggattacaa ggcttttttt tcttttttgag aggaggtctc    7500
actatattgc ccagtctggt ttcaaactcc tggtctcggc caggcgcggt ggctcacaca    7560
tgtaatccag catttgggga ggctgaggca ggctgatcac ttgaggccag gagtttgaga    7620
tcagtgaaac cccatctcta ctaaaaatac aagaaaatta gctgggcgtg gtggtgccca    7680
cctgtaatcc cagctactgg ggtggctgag gcacgagaat ctcttgaact tgggaggcgg    7740
aggttgcagt gagctgagat tgcgccactg cactccagcc tgggtgacag cgcgagactc    7800
tgtctcaaaa aagcaaaaaa cataaaacaa actcctggtc tcaagctatc cttccttctt    7860
ggcctccgga aatgatggga ttacagacat gagccactgc gccctgctgg aacttaggtt    7920
tttgtttgtt tttcccaaca ctttcttcag atcttcttca ttcaggtcaa tttgagtgac    7980
ctccttttt tccccaattt ttctcagggg actcgaagcc ccaccctgg ccccacccag    8040
```

```
ctgagggccc tgagtgctga ggtttctcag ggcaagtgag cgagcgggtg ggaggtgttg    8100
ggggctggaa gcaggggggcc agtttcctcc tgggcccatc ccagggaggc tttccttctt    8160
tctttctttc tttctttctt tttttttttt ttttgagac agagtctgac tctgttgtcc    8220
aggctggagt gcagtggtac aatcttggct cactgcaacc tctgcctccc aggttcaagt    8280
gattgtcctg cctcagcctc ccgagttgct gggattacag gaacgcacca ccacacccgg    8340
ctaagttttg cactttttag aggcagggtt tcgccatgtt ggccaggcag gtctcaaact    8400
cctgacctca agtgatcctc ccgcctcggc ctcccaaaat gctgtgatta caggcataag    8460
ccaccgcacc cggcctccag cactccttc catgccctcc ctgctcagaa gtccaatccc    8520
ctctgaccag gactgagggg cttttctct ctgtgcccca ggcaagttgc actcatggca    8580
cctccaagtg aagagacgcc cctgatccct cagcgttcat gcagcctctt gtccacggag    8640
gctggtgccc tgcatgtgct gctgcccgct cggggccccg gccccccca gcgcctatct    8700 ttctcctttg ggaccacttt ggctgaggac ctgtgcgtgc aggctgccaa ggccagcggt    8760
gagtgcatcc ctagtggatc gggccagagg aaggatggg gctgtgtggg gccaagattg    8820
gaagctggaa tagttgcctg cagaagtcag catcggagct ggggctttgg gggatgagta    8880
ggagttttgt aatggagaag ggtgtgcagg gttggcttct gaggcagagg gaatggcctg    8940
tgcagacgga gaggtgtgac ggcacatgaa gggaacagct ggtcatacct tgaggtatgg    9000
aaggatctgg acggttgggt atgatgctgg cactcctgaa gggcacagat ggggtgactc    9060
aggagggagc tgatgggacc atcccctgta ggcatcctgc ctgtgtacca ctccctcttt    9120
gctctggcca cggaggacct gtcctgctgg ttcccccga gccacatctt ctccgtggag    9180
gatgccagca cccaagtcct gctgtacagg attcggtagg aagtgccccc cagccccag    9240 ggattgtaca attttatcat ctccttgcat ttcgaggtgc ccacacccct gccccaggga    9300
ggtatggtca ctaccatttt ctcagatgag gaaacagacc agagagggtg ggtcacttgc    9360
ccaaggtcac acagcaagtt aaaggtacaa gctgggctct gtgaggcctc cgcagaatct    9420
gtccctcgcc cccaccataa tgtcactcct actgaggctg ggttgcactt tcatcccagg    9480
gttctctcct ctcctcacag cttttacttc cccaattggt tgggctgga gaagtgccac    9540 cgcttcgggc tacgcaagga tttggccagt gctatccttg acctgccagt cctggagcac    9600 ctctttgcc aggtgggggtt ctgcctgggg tttgacccag ggggttgggg gtccaagggg    9660
caacatgagg actggcatgc aatcaggtgg ggcctcgtct gaccctccct gtggcagtcc    9720
aggggtgggg gtcagcccag gattgggggg gtctgcaggt taacaacagg gcttgaagtt    9780
gggtggcctc agctgatgct ccctgtggcg gccccccagc accgcagtga cctggtgagt    9840
gggcgcctcc ccgtgggcct cagtctcaag gagcagggtg agtgtctcag cctggccgtg    9900
ttggacctgg cccggatggc gcgagagcag gcccagcggc cgggagagct gctgaagact    9960
gtcaggtgag agccaccagg ctgtggggac ggcctctgct tggagtgag caacgtgggc    10020 tccatcgggg cttgccggg ctcccaccat ggagttctcc tgcaagcttt cagggtgttc    10080
ctatgaccca gggcctccca cgaacccagc cctctccacc cccaggctcc agctggacag    10140
acacctgacc tccccagct aaaggcctg tggggtccct gtccgacctg tgggcgccaa    10200
tggccctccc ctactctgag gtccggtcct catacctgac cctgaatgag agtctgtgtg    10260
tgcctggtgc cccaactagg gccgcacccc agccctggg ctaaagcctg gtttgtgtg    10320 tgtccccgcg gggacccctc ccgacgctga gggccggctc cctcccctcc aaccctgca    10380
```

```
gctacaaggc ctgcctaccc ccaagcctgc gcgacctgat ccagggcctg agcttcgtga    10440
cgcggaggcg tattcggagg acggtgcgca gagccctgcg ccgcgtggcc gcctgccagg    10500
cagaccggca ctcgctcatg gccaagtaca tcatggacct ggagcggctg atccagccg    10560 gggccgccga gaccttccac gtgggcctcc ctggggccct tggtggccac gacgggctgg    10620
ggctgctccg cgtggctggt gacggcggca tcgcctggac ccaggagaa caggaggtga    10680 gggcggactc ccccgctggg cggggccaac gtggggcgg ggctcgggga ggggccggag    10740
agtggtaggg gatgtgggc ggagccaaaa cgaaagactt ggggaagtgg gcgaggctta    10800
atgaggggcg gggcttagtg agggaggaga ctgcgggaat gggaggggca aactgagtga    10860
agggttgggc tgagcgaccc gggaatgaaa atggagggg ttgaggagtg ggtgggtggg    10920
cgctggaacg aggcaagact aagaggcaga gtgaggctcc gagagctggg aggctgcgaa    10980
gcggggcagg gatcaagggg cggggtccgg cagagagaag gaggcgggga ttggcagagc    11040
gggtgggaga tgtttgggga tgggtagggg aggtgttgag aggttggagt tgataggagg    11100
gggcgcggct tggaagggtt gaatggcaaa gggatagggga gtggatggtg tggcttgggg    11160
gtgggttcat gggcgtggtt tggcggggtc cagctgggcc cccacttcgg tactcccct    11220 ccttcccagg tcctccagcc cttctgcgac tttccagaaa tcgtagacat tagcatcaag    11280
caggccccgc gcgttggccc ggccggagag caccgcctgg tcactgttac caggacagac    11340
aaccagattt tagtgggtgc aggattcccc tccccttcag ccttacccg agggcggac    11400 cggcaccctc gggtttcact gggctctgac gcttgtccct cgcaggaggc cgagttccca    11460
gggctgcccg aggctctgtc gttcgtggcg ctcgtgacg gctacttccg gctgaccacg    11520
gactcccagc acttcttctg caaggaggtg gcaccgccga ggctgctgga ggaagtggcc    11580
gagcagtgcc acgcccccat cacgtaagga cctgtccccc attcccggcc tctgtggcca    11640
ctcagggccc ctccccttct ctatgcctca gtgtcctcac cttccaggag ccctggacag    11700
gggtcaagtt ttcaaaccac acctgccgca cagtcagcgc tcagtgaagc tgaagtattc    11760
cttctgcttc acagggcgac cactactctc tctctctctg accccagggc catttcctgg    11820
agatggacaa gtcgcccacc ttcacctaca gcctcttgtt taatctccca ggaagggcca    11880
ggcatagtgg ggcacacctg caatcgcagc gctttgaggg gccaaggcag gaggattgtt    11940
tgaactcagg agttggagac aagtctaggc aacaggagag accccatctc tacaaaaaaa    12000
gaaaaaaaaa tagctgggtg tggtggttga cctgtagtcc cagcgactcc ggaggctgag    12060
gcaggaggat cacttgagcc caggagttgg aggctgcagt gagctgagat tgcactccag    12120
cctgggcaac caagcaagac cctgtctcta ttaaaacaaa caaacaaaca aacaatctcc    12180
cagaagaggc caagacttac ggctgatttt cttttttctt ttttttttg agacggagtc    12240 tggctctgtc gcccaggctg gagtgcagtg gcacgatctc ggctcaatgc aacctctgct    12300
tcccagggtc acgccattct cctgcctcag cctcccgagt agctgggact acaggtgctc    12360
gccaccacgc ccggctattt ttttgtattt tcagtagcga cggggtttca cggtgttagc    12420
caggatggtg ttgatctcct gacctcgtga tccacctgcc tcggcctccc aaaatgctgg    12480
gattacaggc gtgagccacg cgcgcctgcc catggctgat tttataaatg gggggagggt    12540
gtcacctggc aaggatccca gggctacaga ggtacctgaa tttgagccca ggtctctctg    12600
tcttcttcta tctctgactc ctccccattc cctctcacct tccccacag tctggactt    12660 gccatcaaca agctcaagac tgggggctca cgtcctggct cctatgttct ccgccgcagc    12720
ccccaggact ttgacagctt cctcctcact gtctgtgtcc aggtcggtct actgctaggg    12780
```

```
tgggtagtgg agggctgcct ggaggaggtg acgtttgaat tgagatttaa aagatcagtc    12840
agcatttggt tcctgaagaa taggagggaa aagacacccc cggtgaacag aacagcatat    12900
tcaaaggtct aaagactgga atgagttcat ggtgctttag gagaaaggac tgaggctggg    12960
cacagtggct tacgcctgta atcccagcac tttgggaggc tgaggtaggc agatcaagag    13020
atcaagagat cgaaaccatc ctggccaaaa tggtgaaacc ctgtctctac taaaaatata    13080
aaacttagct gggcgtggta gtgggcatct gtagtcccag ctactcggga ggctgaggca    13140
ggagaatcgc ttgaacctgg gaggcggagg ttgcagtgag ccaaggtcac gccattgcac    13200
tccagcctgg gtgacagagc cagactccgt ctccaaaaaa aaaaaaaaaa aagaaaaaa    13260 aaggaagaag gactgagaag gagagtgtct gtcgctcagt cccactcagg ggccactctt    13320
ctttgcagaa ccccccttggt cctgattata agggctgcct catccggcgc agccccacag    13380
gaaccttcct tctggttggc ctcagccgac cccacagcag tcttcgagag ctcctggcaa    13440
cctgctggga tggggggctg cacgtagatg gggtggcagt gaccctcact tcctgctgta    13500
tccccagacc caaaggtgag cccccttcctc ccctggaatg agtggctgat ctgggaccct    13560
ggctttctat gtctgtgaca gctcctgtgt gggtggcaag tggcagaaac tgcaggtcaa    13620
ggtgggttag ggaagaaaag gtgatttgtt ggctcaggaa gttagagata tataaccttt    13680
aggtctggct tgatctaggc acagctagat gtgagccatg tcatctgcac ctagtctctc    13740
tccagctctc agctcttcct ctgggtgaat ttcactcctg gacaaacccc tctgatggga    13800
caattctgag atgtgagttc ttctgagtct cccagaatcc ctggtagaac cgatccctgg    13860
ttgtccacag tgccacttgc tcattaaagc cccctgcagg gctccttcct tccttgtcgc    13920
tcatcccaaa tccctatggg ggcttttctgg atctcctttc aaataaacca tgtgccagcc    13980
aggcacagtg gctcacgtct gtaataccag cacttcggga ggctgaggca gatggatcac    14040
ctgaggtcag gagtttgaga ccagcgtggc caacatggtg aaactccatc tctactaaaa    14100
atacaaaaat tagctgggtg tgctggcaca ctcctgtagt cccagctact tgggaggctg    14160
aggcaggaga attacttgaa cccaggaggc agaggttgca gtgagccgag atcacaccac    14220
tgcactccag cctgggtgac agagcgagac tctgtctcaa aaaaaaaaaa aaaaaaaat    14280 tagccgggca cggtggcaca cacctgtagt cccagctatt cgggaggccg aggcaggaaa    14340
atcgcttgaa cctgggaggt ggaggttgca gtgagctgag atcgcaccac tgcccaccca    14400
gcctggatga cagagtgaga ctccgtctca acagcagcag caacaacaaa acaaaaacaa    14460
caacaaaaag ccatgtgccc tgaagtcttc atctcagggt cggcttctag agggtacctc    14520
aaactaaggc atgagttagc taaccttggg ggacttttca cctctgattt ctggtttttc    14580
tccctcatcc tctccccata gaaaagtcca acctgatcgt ggtccagaga ggtcacagcc    14640
cacccacatc atccttggtt cagccccaat cccaatacca gctgagtcag atgacatttc    14700
acaagatccc tgctgacagc ctggagtggg taagaggccc tgggaaatga ggcgatacct    14760
cagtctgggg tccagagact cagatgcgtg gcctcaggca tatgctataa ttttaccttg    14820 cctcggttttt cccatctgta aaatgggggcc agcagctatg tctcgcttgg gctgggatcc    14880
tgcaggaacc ccctcactgg cctcttctgc tgtccctca ccattcagca tgagaacctg    14940
ggccatgggt ccttcaccaa gatttaccgg ggctgtcgcc atgaggtggt ggatggggag    15000
gcccgaaaga cagaggtgct gctgaaggtc atggatgcca agcacaagaa ctgcatggag    15060
gtgagagcaa tgtggaccag acttttggag tcggggctgg ctggagaggg ggtcgtggat    15120
```

```
gcagagaaat ttaaaaacac acagggacct gggcgtggtg gctcatgcct gtcatcccag    15180
cactttggga ggctgaggca ggaggatggt tgaagccag gagttcaaga acagcctagg     15240
caacatagcg agacctcgtc ttgacaaaaa aattttaggc cgggcgcggt ggctcacgcc    15300
tgtaatccca gcactttggg aggctgaggc gggcagatca tctgaggtcg ggagttcgag    15360
accagcctga ccaacatgga gaaaccccgt ctctactaaa aatacaaaat tagccgggcg    15420
tggtggtgca tgcctgtaat cccagctact cgggaggctg aggcaggaga attgcttgaa    15480
tctgggaagc ggaggttgca gtgagtcaag atcgcgccac tgcactccag cctgggtgac    15540
agagggagac tctgtctcaa aaacaaaaca aacaaaaca aaaaccata gatgatagtg       15600 ggaacttctg tcccgtatca gaaaatcatg gtagtgctgt gtgcactaat ggcagactcc    15660
agggccaaag gtgacctgtg gccaggtgtt cccctaaggc aggtctgtga gcacaaaatt    15720
tgggattatt ggagtggaag aaacccacgc atcttctctc ccttcccacc ttccccagtc    15780
attcctggaa gcagcgagct tgatgagcca agtgtcgtac cggcatctcg tgctgctcca    15840
cggcgtgtgc atggctggag acagtgagag ccccccaccc acccacccca ccctgcctc     15900 acccaagtct aggctgttct tcccacctct gttctgagcc gctatatgac agccccagca    15960
acacactggg ccaccctgga tgggagccgt gttcattacc ctttatttat gtctctccat    16020
catcactcct tggaaagcgg ctccaggttc tcacccatat ccagcccag aatgacctga     16080 agtcagacaa acctggcttt ctaatctctg cagctttgta caggtcacgt aacctttctg    16140
agccttggtt tcattggttg ggagtctagg atgggccagg agctgggaca gagcctagaa    16200
tgtgacaggc agggtgtgat gaggtgtgag gagggcagca cggagcactg tggatggtca    16260
gagaggctgc tgggccagcc tgggggttgg gcaatgcttg tgggaagaca gagatgcatt    16320
ctaacctgga aagataagga caagtgtgga ttaggaaagg aagaggggtg ttctaggcag    16380
aggacacaga atatgcaaag ggttagaagt gagatacaga ggctgggcgt ggtggctcat    16440
gcctgtaatt gaaaagccga ggcgagtgga tcacctgaga tcaggagttc aagaccagtc    16500
tggccaacat ggcaagaccc cgtctctact aaaaatacaa aatcagccgg gtgtggtggc    16560
atgcgcctgt agttccagct acttaggagg ctgagacagg agaatcactt gaacccggga    16620
ggcagaggtt gcagtaagcc gagatcgcac cactgcactc cagcctgggc aacagagtaa    16680
gactctgtct caaagaaaa gagaaaaaaa aagtgagat acagatacag acagggctca     16740
acaccttcca ggcattccag gcaaatcatt cagagatgga ggtgggagga gaggtgagta    16800
ctgtatgaac agaggcagca ggggagggaa cagacagaga tgagagtttg agagaccctg    16860
agagccaggg tgttggcaga acctcctcaa cacaagtgca gttcagtctc ccaaccccgc    16920
ctctccctgc tgccaaccag gcaccatggt gcaggaattt gtacacctgg gggccataga    16980
catgtatctg cgaaaacgtg gccacctggt gccagccagc tggaagctgc aggtggtcaa    17040
acagctggcc tacgccctca actatctggt gagtgctcct ctgcctgctc caccctccat    17100
tcccagggaa ggctttctct gggtggaaga ggaattggga gtgggctctg tagtatgcat    17160
aggagtttgg taagggttcg aggggagggc attttaggtt caggttgtga gaacactaga    17220
agagaacaag tcattcttgg atgtcaggc gtgtggtgaa tgacgaggct gggcaggaag     17280
aaaggcttcc tagaagaagg aacattggag atagggcctt aaaagttgag tagaagttca    17340
tcaagagaag aaaggaagga aggaatgtca ggctgaggga acagcctagg caaaggcctg    17400
caggctagat agtgtgttgc atcccctggg gcctatcagg cagttctgtt ggcaggagac    17460
cagggtgcaa gtgtggaagg gaagttcatt ggaagcttga gcaagggcct tgaatgccag    17520
```

```
gctgaggagc tttcactttg tgtcaaaggc actggggagt cacaggatgg ggtggtgttt    17580
gagaagggga gggacatagc caggtcagtg taggggtga actagagggg caagacagga     17640
tgtcaggagt cagggacgat gctggagcat gtctgagcag taccaagtgg gttttgaagg    17700
atgtatagga gtttgccaaa cagactcttc attcatcaaa ccctcccggg cattttcctg    17760
tgtctggccc ccttaggagg acaaaggcct gccccatggc aatgtctctg cccggaaggt    17820
gctcctggct cggagggggg ctgatgggag cccgcccttc atcaagctga gtgaccctgg    17880
ggtcagcccc gctgtgttaa gcctggagag taagttcctg gaggtggagg agggaggggc    17940
tgagcagggc aaggaagtgg atccctgatc ccactttcat tccctcagtg ctcaccgaca    18000
ggatcccctg ggtggccccc gagtgtctcc gggaggcgca gacacttagc ttggaagctg    18060
acaagtgggg cttcggcgcc acggtctggg aagtgtttag tggcgtcacc atgcccatca    18120
gtgccctgga tcctgctaag gtcagagccc ctcacccggc atcggtctcc gaaccccac     18180 tttgacagaa gggcagactg acatccagtc tggggagatt ggggtgggtc tattgggttg    18240
gggattaccg actgctcctc tcaccctcag aaactccaat tttatgagga ccggcagcag    18300
ctgccggccc ccaagtggac agagctggcc ctgctgattc aacagtgcat ggcctatgag    18360
ccggtccaga ggccctcctt ccgagccgtc attcgtgacc tcaatagcct catctcttca    18420
ggtgcccgct gggacgggtt gggtggggag ggctgtgatg tcatattggg cccagtggaa    18480
ggagcgtggt ttgcagcagg ccacgccctg tgtgtctggt gaggttggag gggttggtga    18540
ctgtgacagt cagtgtgagc ttcaacagct actgtaacga acagtcccct cagttcaagg    18600
ttcaacatga tgatattta tttatttatt tattttgag acagagtctt gctctgttgc     18660
ctaggctgga gtgcagtggc acaatttcgg ctcactgcaa cctctacctc cttgaacctc    18720
tagttcaagc gattctcctg cctcagcctc ctgagtagct gggattacag tgtgtgccac    18780
cacgcccagc taattttgt attttggca gatatgggt ttcaccatat ggctaggct       18840 ggtctcgaac tcttgacctc aggtgatccg cccacctcta cctcctaaag tgctgggatt    18900
tcaggtgtga gccaccatgt ctggtctatt tcattctttt aaaaaatgt ttggctgggc     18960 gcagtggctc atgcctatag ttccagctat aggtaggtgg atcgcttgag cccaggagtt    19020
caagaccagc ctgggcaaca tggcaaaact ccatctctac aaacaaacaa acagaaaatt    19080
agccaggcat ggtgatgcat gcctgtatgc attttatt tattttattt tatattttg       19140 agacactatc tccctctgtc acctaggctg gagtgcagtg gcgtgatcct ggctcactgc    19200
aacctctgcc tccctggttc aagcaattct cccgcctcag actcccaagt agctaggatt    19260
acaagggcgt gccaccaaac acggctaaat ttttgtattt tttagtaaag cagggttt      19320 gccatgttgg ccgggctagt cttgaactcc tggtctcaaa gagatccgtc cacctcagcc    19380
acccagtgct gggattacag gcatgagcca ccacaccagg ctgatttt ttttttttt       19440 tttttttc tgtgatgggg ttttgctatg ttccccaggc tggtcttgaa ttactggctc      19500
aagcaatcct cctgccttag tctcccaaat agctgggatt acaggcacac acaaccatgc    19560
ccagtgtgat atttagtctt cattcaatga gggtgtccag gcccacagga acctctcact    19620
tagtggctgc actcacctca ggcgttgggt ccccgttgga tcctctgcag ataaagaga     19680 gagtgtggag ggccccgtat taggtttcca tgggtcagga ctggagggc acccagcata     19740 tcttgtccat cagcctgagc tcagtcatgt ggccacattt catagcagtg gaactgggga    19800
aatgagttct cattatgtcc tccatctttg tagccatgtg gagttgcaca gggtgtgcac    19860
```

```
tgcacgagga ggcttccttt gcctgggaca gagtgggaga ccctttttc cagtctccac      19920 aaggtaccct ttggcttgca atggccctgc cataatgcac agagagggtc aatatgcaga    19980
tggaggttgc acagcaagtc aactcaggag tggggcccag gatgagaggc gctgcttacc    20040
actgcccatg cccccacccc agactatgag ctcctctcag accccacacc tggtgccctg    20100
gcacctcgtg atgggctgtg aatggtgcc cagctctatg cctgccaaga ccccacgatc     20160
ttcgaggaga gacacctcaa gtacatctca cagctgggca aggtaaggtg ggcagggcca    20220
gggtgggttg gagagggcag ggcagcatcc aggtgcctgg acatcagtcc cgctatcccc    20280
cagggcaact ttggcagcgt ggagctgtgc cgctatgacc cgctaggcga caatacaggt    20340
gccctggtgg ccgtgaaaca gctgcagcac agcgggccag accagcagag ggactttcag    20400
cgggagattc agatcctcaa agcactgcac agtgatttca ttgtcaagta tcgtggtgtc    20460
agctatggcc cgggtgagcc agctcccgga tgagtgaacc aagacgtatg ggtgcttttc    20520
aaagtgcaca ttcttaccct cctgccaggc cactttaggt aggctgggaa cgtgattatt    20580
gatccagatt cacatgggtt acaggtttga atcctgactc tacccctacc cagttgtgaa    20640
accttaactt ttctgagcct cagtttctcc agctgaaaaa tgggccattg tgatatttac    20700
tttgttgttg ttgttgtttg tttgttttt tgagacagag tctcgctctg tcacccaggc    20760
tggaggcagt ggctcaatct cggctcactg caacctctgc cttccaagtt caagtgattc    20820
tcctgcctca gcctccagag tagctgggat tacaggagcg tgccaccaca cccggctaat    20880
ttttgtgttt ttagtggaga tgggttttca ccatgttggc caggctggtc ttgaactcct    20940
gacctcaagt gaggcttcca aagtgctggg attacaggcg tgagccactg cacctggccg    21000
tgatatataa acacatcaat gtatgttgta gaaagtactc aagagatatt agcaatgtgt    21060
cattgttgcg gttcccatat tacagtcagc aaaactgagg tcgagaggga cacaaggtcc    21120
cactgtgaaa gggggggaaga atgggggggac gagcagggct gggccctgct gtgacagatc    21180
ctgccttctc caggccgcca gagcctgcgg ctggtcatgg agtacctgcc cagcggctgc    21240
ttgcgcgact tcctgcagcg gcaccgcgcg cgcctcgatg ccagccgcct ccttctctat    21300
tcctcgcaga tctgcaaggt gcgaggggc gccccgggac ttgtggggat tcagctggca    21360
cggcctgggc aggggtctgc ttggaggtcg cggtgaaggc tgaggagtgg tttggggtcc    21420
aggtctcggg agtggtgggg ttggcttagg gctcaggatc agaacttcag tggaggatgg    21480
ctcgggggta gggttatagt tggggtctgg gttggggtgc caggtcacgc ttggggtacc    21540
tgccggatta tcctgggatc ctctctgcac gctcacaccg cccgcccgca gggcatggag    21600
tacctgggct cccgccgctg cgtgcaccgc gacctggccg cccgaaacat cctcgtggag    21660
agcgaggcac acgtcaagat cgctgacttc ggcctagcta agctgctgcc gcttgacaaa    21720
gactactacg tggtccgcga gccaggccag agccccattt tctggtgggg aacccgcgcc    21780
taggctccgc ccctattccc cacggctctg gctccgcccc cagccatgcc ccgccccct    21840 cccgctgctt tgctccccag ccttagcccc gcccttcctc cgctgcagct ttggcccctc    21900
ccactcccca gagccccgcc ccctcaacag cactggctcc tctgtctccc gctgccctgc    21960
tgtcagcggc cccagccctt agcccgccc ttctctcagc tctcgccccg cccaagcttc    22020 agaacccac ccctccaaca cgctggctcc gcccctcagg gctggcccc tcttagttcc      22080 gcccttcccc ccgcccagtt ctggccctc ccctcccac ggctctgcc ccgcccccat       22140 ctccgcccct ccgtgctgcc cccgcctcct ccccacagcc ttagctcttc ccaggcacct    22200
cccagggctg gagaatccac ctatcccaca gccagggaaa ccgagaccct ggagacggga    22260
```

```
ctgacctgct cacagtcccc acctaccctg accagttccc cattccaagg ctgccccct      22320
cttcctgtcc tttctacacc ctcgcatctc aagaccttgt ccctctcca ggtatgcccc      22380
cgaatccctc tcggacaaca tcttctctcg ccagtcagac gtctggagct tcggggtcgt     22440
cctgtacgag ctcttcacct actgcgacaa aagctgcagc cctcggccg tgagtcggct      22500
tcccagagcc cccagccttc ttctccctcc acgccctcg tggccaatct ccaacctgtc      22560
tgcgcctgcg tccctcttta gcatggggtc acctggtccc agcatcatag gcccagtgg     22620
ggaggacgct tcctcacctt tctgaccct tcacggttca ggcagcccct cccgctcca      22680
tcacagatgg cccctacccc caccacgggt ggccctccc cctccaccca cggaggctcc      22740
tcccccacca catgcgctcc tccttggctc caggagttcc tgcggatgat gggatgtgag     22800
cgggatgtcc ccgccctctg ccgcctcttg gaactgctgg aggagggcca gaggctgccg     22860
gcgcctcctg cctgccctgc tgaggtgagc gccgcagggc tagcctcagt ttcccagtct     22920
gtagattggg ccggggtctc gggcaagcca gctggcgcct gagtctctgt actgagaaga     22980
aaggctagag tgtgaggccg atgaggatcc tggcccccac ttggctactc tctcactgtg     23040
tggcaagtca gagcactttc agagcctcag tttacccttt tccaaaatga gaatagtaat     23100
gccttatagg gtgagggaag attagactcc tgaacacctg tgcctatgag ggctcagctc     23160
aaagccgagc acacagtcga tgctccataa atggtggtga cgttcatggt ttttttttt     23220
ctttctttct ttctttttta tagatggggg ctcactctgt tgcccaggct ggggtgcaat     23280
tatagctcac tgcagcctcc aactcctgag ctcaagtgat tccctagtt cagtgtctct      23340
agtagcagga gctacaggtg tacaccacca cacttggcta atttaaaaat aattttttag     23400
agatgggagc tcactatat tgcccaggct ggtcttgaac tcgtgggctc aagcgattct      23460
cctgcctcag cctcccaaag tgctgggact ataggtgtac atcaccatgc ctggctaatt     23520
taaaataat tttggccagg tgtggtggct cacacctgta aacccagcac ttttgaaggc      23580
tgaggcggtc agatcaccgg aggtcaggag ttcgagacta gcctggccaa catggtgaca     23640
ccctgtctct actaaaaata caaaaattac ccatgtgtgg gtgcctgtga tctcagctac     23700
ttgcgaggct gaggcaggag aattgcttga acctgggagg ggaaggtttc agtgagccaa     23760
gatcatgcca ctgcactcca gcctgggcga cagagcaaga ttccatctca aaataaataa     23820
ataaataaat aaacaaacaa ataagataaa ataatttttt ttaagagaca aggtctcgct     23880
atgttgccca ggctggtctt gaactcctgg gctcaagcga tcctcctgcc ttggcctccc     23940
aaagtgctga gatttacagg cataagccac tgtgcctggc taattttaaa aattttttt     24000
aaagagatgg ggtctctctg tgttgcctag gctggtcttg agctcgtggg gtcaagtgat     24060
cctcctgcct cggcctccca aagtgctggg attacagacg tgagccacca catcccaccc     24120
tctcatggtt tataatcata taatcataac ctttgtggaa gtgtctgaca tgcagttggt     24180
cattgataaa ttaatttgct caggccaaaa acatttattg agtgccaact gtgtgccagg     24240
acttgttggg tgctgaagac cctgtcctcc cagtaactag caaaatctga taagaacatt     24300
ctaggctggg cacgatggct catgcctata atcccaacac tttgggaggc tgaggcagaa     24360
ggatcactgg agcccaggag ttcaagacca gcctgggcaa cgtagtgaga ccttgtctct     24420
acaaacaata caagcaatag ccggtgtggt gacatgcacc tgtggtttca gctactaggg     24480
aggctgaggc aggaggatca ctggaaccca ggagttcaag accagcctgg gcaacatagt     24540
gagaccttgt ctctacaaac aatacaagca atagccggtg tggtgacatg cacctgtggt     24600
```

```
ttcagctacc agggaggctg aggcaggagg attgcttgag cccaggaggt taaggctgca    24660
gtgagccatt attgtaccac tgcactccag cctggacaac agagtgacac cctgtctcaa    24720
aacaaaacaa aacaaaacaa aacaaaacaa aacaaaacaa aacaaagaca aaattatggt    24780
agtgataagt gccttgaaag agatgaacag agggaaatgg tggggtgggg gtggtcaaag    24840
agggcctctt acgggccgac gctggaagg aggaggagcc tacccatgag taaagctagg     24900
agaagaaatt tccagtggag gacacggaag ggaaaaaggc cttggggagg taatgagctg    24960
ggtgccttta agcaccagtg cgatggaggc agatgtgact gcccggaaca aatgagggaa    25020
ggagggatgg agatgagcga aggagggcat caggagagg tggtgttttt ttgttgtttt     25080 ttttttttg agacgtggtt ttgctcttgt tggccaggct ggagtgcaat ggcgcaatct     25140
cggctcacca caacttccgc ctcccaggtt caagcaattc tcctgcctta gactcccgag    25200
tagctgggat tacaggcaca cgccacctgt aattttttt ttttttttt ttttttttt      25260 ttttttttt ttttagttaa gatgggtttt ctccatgttg gtcagggtag tctcgaaagg     25320
agaagtgtgt tgtaaaatcc ataagggctg gcgcggtgg ctcacacctg taatcccagc     25380
cctttaggag gccgaggtgg gtggattaca tgaggtcagg agttcaagac cagcctgacc    25440
aacatggtga aaccccgtct ctactaaaaa tacagactta gccaggtgtg gcggtgtgtg    25500
catgtaatcc cagctacttg ggaggctgag gcaggagaat cgcttgaacc caggaggcag    25560
ggtttgcagt gagccgagat cgcaccactg cattccagcc tggcaacaa gagcgaaact     25620 ttatctcaaa taaataaata agtaagatcc atagggagcc atgggagttt tggagcaga    25680 gatgggatgg aatttaatt tgtgttttaaa actgaatgag tgcggtggct catgcctata     25740
atcccagcac tttgggaggc caagacaggt ggatcacctg agatcaggaa tttgagacca    25800
acctggccaa catggtgaaa ccctgtctct actcaaaata caaaattagc caggcgtggt    25860
ggcacgtgcc tataatccca gctactcagg aggctgaggc aggataattg cttgaacccg    25920
ggaggcggag gttgcagtga ccgagatca tgccattgca ctccagcctg acaacagag     25980 ctagactccg tctcaaaaaa acaaaaacaa atacgctgaa tgggagttgt gtcctttgga    26040
ctgctcaggc acgaccccat tatctgtccc ccgcccctca ggttcacgag ctcatgaagc    26100
tgtgctgggc ccctagccca caggaccggc catcattcag cgccctgggc cccagctgg     26160 acatgctgtg gagcggaagc cgggggtgtg agactcatgc cttcactgct cacccagagg    26220
gcaaacacca ctccctgtcc ttttcatagc tcctgcccgc agacctctgg attaggtctc    26280
tgttgactgg ctgtgtgacc ttaggcccgg agctgcccct ctctgggcct cagaggcctt    26340
atgagggtcc tctacttcag gaacaccccc atgacattgc atttgggggg gctcccgtgg    26400
cctgtagaat agcctgtggc cttttgcaatt tgttaaggtt caagacagat gggcatatgt    26460
gtcagtgggg ctctctgagt cctggcccaa agaagcaagg aaccaaattt aagactctcg    26520
catcttccca accccttaag ccctggcccc ctgagtttcc ttttctgtct ctctcttttt    26580
atttttttta tttttattt tatttttgag acagagcctc gctctgttac ccagggtgga    26640
gtgcagtggt gcgatctcgg ctcagtgcaa cctctgcttc ccaggttcaa gcgattctcc    26700
tgcctcagcc tcccgagtag ctgggattac aggtgtgcac caccacccc ggctaatttt    26760 ttttatttt aatagagatg aggtttcacc atgatggcca ggctgatctc gaactcctaa    26820
cctcaagtga tcctcccacc tcagcctccc aaagtgttgg aataataggc atgagccact    26880
gcacccaggc tttttttttt ttaaatttat tattattatt tttaagagac aggatcttgc    26940
tacgttgccc aggctggtct tgaactcctg ggctacagtg atcctcctgc cttatcctcc    27000
```

```
taaatagctg ggactacagc acctagtttt gagtttcctg tcttatttcc aatggggaca   27060
ttcatgtagc tttttttttt tttttttttt tgagacggag tctcgctctg tcgcccaggc   27120
tggagtacag tggcgcaatc taggctcact gcaagctccg cctcctgggt tcacaccatt   27180
ctctcgcctc agcctcccaa gtagctggga ctacaggcgc cgccaccac acccggctaa    27240
tttttttgtat tttagtaga cggggtttt caccttgtta gccaggatgg tttccatctc    27300
ctgacctcgt gatctgcccg tctcggcctc ccaaagtgct gggattacag gcatgagcca   27360
ctgcgcccgg ccctcatgta gctttaaatg tatgatctga cttctgctcc ccgatctctg   27420
tttctctgga ggaagccaag gacaagagca gttgctgtgg ctgggactct gccttttagg   27480
ggagcccgtg tatctctttg ggatcctgaa agggggcagg aaaggctggg gtcccagtcc   27540
accctaatgg tatctgagtg tcctagggct tcagttttcc cacctgtcca atggaccct    27600
ttctgtcctc accctacaag gggcacaaag ggatgacacc aaacctggca ggaacttttc   27660
acgcaatcaa gggaaggaaa ggcattcctg gcagagggaa cagcatgcca agcgtgagaa   27720
ggctcagagt aaggaggtta agagcccaag tattggagcc tacagttttg ccccttccat   27780
gcagtgtgac agtgggcaag ttcctttccc tctctgggtc tcagttctgt cccctgcaaa   27840
atggtcagag cttaccccctt ggctgtgcag ggtcaacttt ctgactggtg agagggattc   27900
tcatgcaggt taagcttctg ctgctcctcc tcacctgcaa agcttttctg ccactttgc    27960
ctccttggaa aactcttatc catctctcaa aactccagct accacatcct tgcagccttc   28020
cctcatatac ccccactact actgtagccc tgtccttccc tccagcccca ctctggccct   28080
ggggctgggg aagtgtctgt gtccagctgt ctccctgac ctcagggttc cttggggct    28140
gggctgaggc ctcagtacag agggggctct ggaaatgttt gttgactgaa taaaggaatt   28200
cagtggaaaa gattttgtgc tggacttggg gcgatgggga gcctcagagg gtgtgtgagc   28260
tgggagggat gcggttagag ctgtgggcca gagacctctc agggagccac tgtgggggcc   28320
ccagggcagg ctggtggagg aggaccactg ggtggggctt ggctggggcc ctcaaggaca   28380
gagccccctc actcccagcc ccagctgctg gccttggctg cagcctgggg gagctgatta   28440
caggctctct gtgggtgggg aaggaacagg atgctctccc ggtggtcaga ggacaaggcc   28500
aggttgggggg agcgaggctg tggggagggg accagcatca ctgggccgg accacctccc    28560
caccgaccgg ccccgtcat gtgcacctca taactgctag aaagatgtgg agagtggcca   28620
ggctcagtgg ctcacgtctg taatcccagc actttaagag gccaaggcag gaggatcact   28680
tgaggtcagg agtatgagat cagcctggcc aacatggcga aaccgtctct attaaaata    28740
caaaaattag cctggtgttc tggcacatgc ctgtaatccc agctactcag gaggctgaga   28800
cagaagaatt gcttgaaact gggatgtgga ggttgcagtg                          28840
```

<210> SEQ ID NO 2
<211> LENGTH: 1124
<212> TYPE: PRT
<213> ORGANISM: Homo sapiens

<400> SEQUENCE: 2

Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
            20                  25                  30

Arg Gly Pro Gly Pro Pro Gln Arg Leu Ser Phe Ser Ser Gly Asp His
        35                  40                  45

```
Leu Ala Glu Asp Leu Cys Val Gln Ala Ala Lys Ala Ser Gly Ile Leu
             50                  55                  60

Pro Val Tyr His Ser Leu Phe Ala Leu Ala Thr Glu Asp Leu Ser Cys
 65                  70                  75                  80

Trp Phe Pro Pro Ser His Ile Phe Ser Val Glu Asp Ala Ser Thr Gln
                     85                  90                  95

Val Leu Leu Tyr Arg Ile Arg Ser Phe Tyr Phe Pro Asn Trp Phe Gly
                100                 105                 110

Leu Glu Lys Cys His Arg Phe Gly Leu Arg Lys Asp Leu Ala Ser Ala
            115                 120                 125

Ile Leu Asp Leu Pro Val Leu Glu His Leu Phe Ala Gln His Arg Ser
        130                 135                 140

Asp Leu Val Ser Gly Arg Leu Pro Val Gly Leu Ser Leu Lys Glu Gln
145                 150                 155                 160

Gly Glu Cys Leu Ser Leu Ala Val Leu Asp Leu Ala Arg Met Ala Arg
                165                 170                 175

Glu Gln Ala Gln Arg Pro Gly Glu Leu Leu Lys Thr Val Ser Tyr Lys
                180                 185                 190

Ala Cys Leu Pro Pro Ser Leu Arg Asp Leu Ile Gln Gly Leu Ser Phe
            195                 200                 205

Val Thr Arg Arg Ala Ile Arg Arg Thr Val Arg Arg Ala Leu Pro Arg
        210                 215                 220

Val Ala Ala Cys Gln Ala Asp Arg His Ser Leu Met Ala Lys Tyr Ile
225                 230                 235                 240

Met Asp Leu Glu Arg Leu Asp Pro Ala Gly Ala Ala Glu Thr Phe His
                245                 250                 255

Val Gly Leu Pro Gly Ala Leu Gly Gly His Asp Gly Leu Gly Leu Phe
                260                 265                 270

Arg Val Ala Gly Asp Gly Gly Ile Ala Trp Thr Gln Gly Glu Gln Val
            275                 280                 285

Leu Gln Pro Phe Cys Asp Phe Pro Glu Ile Val Asp Ile Ser Ile Lys
        290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
                340                 345                 350

Thr Asp Ser Gln His Phe Phe Cys Lys Glu Val Ala Pro Arg Leu
                355                 360                 365

Leu Glu Glu Val Ala Glu Gln Cys His Gly Pro Ile Thr Leu Asp Phe
        370                 375                 380

Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
                405                 410                 415

Val Gln Asn Pro Leu Gly Pro Asp Tyr Lys Gly Cys Leu Ile Arg Arg
                420                 425                 430

Ser Pro Thr Gly Thr Phe Leu Leu Val Gly Leu Ser Arg Pro His Ser
            435                 440                 445

Ser Leu Arg Glu Leu Leu Ala Thr Cys Trp Asp Gly Gly Leu His Val
        450                 455                 460
```

-continued

```
Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Thr
            485                 490                 495

Ser Ser Leu Val Gln Pro Gln Ser Gln Tyr Gln Leu Ser Gln Met Thr
            500                 505                 510

Phe His Lys Ile Pro Ala Asp Ser Leu Glu Trp His Glu Asn Leu Gly
            515                 520                 525

His Gly Ser Phe Thr Lys Ile Tyr Arg Gly Cys Arg His Glu Val Val
            530                 535                 540

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
                565                 570                 575

Ser Gln Val Ser Tyr Arg His Leu Val Leu Leu His Gly Val Cys Met
            580                 585                 590

Ala Gly Asp Ser Thr Met Val Gln Glu Phe Val His Leu Gly Ala Ile
            595                 600                 605

Asp Met Tyr Leu Arg Lys Arg Gly His Leu Val Pro Ala Ser Trp Lys
610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
            660                 665                 670

Gly Val Ser Pro Ala Val Leu Ser Leu Glu Met Leu Thr Asp Arg Ile
            675                 680                 685

Pro Trp Val Ala Pro Glu Cys Leu Arg Glu Ala Gln Thr Leu Ser Leu
            690                 695                 700

Glu Ala Asp Lys Trp Gly Phe Gly Ala Thr Val Trp Glu Val Phe Ser
705                 710                 715                 720

Gly Val Thr Met Pro Ile Ser Ala Leu Asp Pro Ala Lys Lys Leu Gln
            725                 730                 735

Phe Tyr Glu Asp Arg Gln Gln Leu Pro Ala Pro Lys Trp Thr Glu Leu
            740                 745                 750

Ala Leu Leu Ile Gln Gln Cys Met Ala Tyr Glu Pro Val Gln Arg Pro
            755                 760                 765

Ser Phe Arg Ala Val Ile Arg Asp Leu Asn Ser Leu Ile Ser Ser Asp
            770                 775                 780

Tyr Glu Leu Leu Ser Asp Pro Thr Pro Gly Ala Leu Ala Pro Arg Asp
785                 790                 795                 800

Gly Leu Trp Asn Gly Ala Gln Leu Tyr Ala Cys Gln Asp Pro Thr Ile
                805                 810                 815

Phe Glu Glu Arg His Leu Lys Tyr Ile Ser Gln Leu Gly Lys Gly Asn
            820                 825                 830

Phe Gly Ser Val Glu Leu Cys Arg Tyr Asp Pro Leu Gly Asp Asn Thr
            835                 840                 845

Gly Ala Leu Val Ala Val Lys Gln Leu Gln His Ser Gly Pro Asp Gln
            850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Glu Pro
```

|  |  | 885 |  |  | 890 |  |  | 895 |  |
|--|--|--|--|--|--|--|--|--|--|

Glu Leu Arg Leu Val Met Glu Tyr Leu Pro Ser Gly Cys Leu Arg Asp
          900             905             910

Phe Leu Gln Arg His Arg Ala Arg Leu Asp Ala Ser Arg Leu Leu Leu
     915             920             925

Tyr Ser Ser Gln Ile Cys Lys Gly Met Glu Tyr Leu Gly Ser Arg Arg
 930             935             940

Cys Val His Arg Asp Leu Ala Ala Arg Asn Ile Leu Val Glu Ser Glu
945             950             955            960

Ala His Val Lys Ile Ala Asp Phe Gly Leu Ala Lys Leu Leu Pro Leu
        965             970            975

Asp Lys Asp Tyr Tyr Val Val Arg Glu Pro Gly Gln Ser Pro Ile Phe
        980             985            990

Trp Tyr Ala Pro Glu Ser Leu Ser Asp Asn Ile Phe Ser Arg Gln Ser
     995            1000           1005

Asp Val Trp Ser Phe Gly Val Val Leu Tyr Glu Leu Phe Thr Tyr
 1010           1015           1020

Cys Asp Lys Ser Cys Ser Pro Ser Ala Glu Phe Leu Arg Met Met
 1025           1030           1035

Gly Cys Glu Arg Asp Val Pro Ala Leu Cys Arg Leu Leu Glu Leu
 1040           1045           1050

Leu Glu Glu Gly Gln Arg Leu Pro Ala Pro Ala Cys Pro Ala
 1055           1060           1065

Glu Val His Glu Leu Met Lys Leu Cys Trp Ala Pro Ser Pro Gln
 1070           1075           1080

Asp Arg Pro Ser Phe Ser Ala Leu Gly Pro Gln Leu Asp Met Leu
 1085           1090           1095

Trp Ser Gly Ser Arg Gly Cys Glu Thr His Ala Phe Thr Ala His
 1100           1105           1110

Pro Glu Gly Lys His His Ser Leu Ser Phe Ser
 1115           1120

<210> SEQ ID NO 3
<211> LENGTH: 140282
<212> TYPE: DNA
<213> ORGANISM: Homo sapiens

<400> SEQUENCE: 3

```
gtgtgatggc acgcacctgt agtccctgct actcaggagg ctgaggcagg aggatcgatt     60
gaggctggga ggtcaagact gcagtgacct gtgattgtgc cactgcactc caaagcaaga    120
ctctgactca aaaaaaaatt atttgcatga aaaacttcat tcgttatgaa gacttgtata    180
gaaacattga aatacactta tgaattacaa ttaagtttaa ggaacagttt acaaagtgac    240
atgtatgcca tgactatatt tatatgaaaa atatgccccg tggaaaaaga taatgggaag    300
aaaacatata atatggtgac tgatttatat caggtttgca agattacagt caattttttc    360
tccagattcc aattttttgga aacaaatttc atgatttgta caatggggat ttagtttagt    420
ttagtgttgt tgaaaaaaca tcattgtttg catctaacat attttcccat tgttatctaa    480
gcaatagctt ttgcagagga agactgatgg ggacatattc ttttgatgaa gatttatgtg    540
tgaaactgtg tgtatgattg atggttgggt ggttgttatt aattttctaa taagaggctt    600
ctacactgca tttggtttaa ttaaatttag atgtatgtca tggattgcat gttagaagga    660
aatatttgta ttcttttgtt ttacactatt gtgtctctcc tatatatcat atattctact    720
```

-continued

```
gagtggcatt ttttttttttt tttgagacag agtctctctg tcgtctaggc tggagtgcag    780
tggtgtgctc taggctcact gcaacctccg cctcccaggt tcaagcggtt ctcgtgcctc    840
agcctctcga gtagctggga ctacaggtgc atgccaccac gcctggctaa ttttttgtatt   900
tttttgtatt tttagtagag acagttttgc catgttggcc aggcttgtct tgaactcctg    960
acgtcaggtg atccacctgc cttggcctcc caaagtgctg ggattgcagg attacaggca  1020
tgaaccactg cacccggccc ttttttgtttt gttttgtttt tttgagatgg aattttttctc 1080
ttgttgccca ggctggagtg cagtggtgcc atcttggctc actgcagcct ctgccttccg  1140
ggttcaagct attttcctgc ctcagcctcc cgagaagctg gaattacagg tgcccaccac   1200
catgcccaac taatttttttg tattttttagt agagacgggg tttcaccatg ttggccaggc 1260
tggttttgaa ctcctggcct caagcaatcc accccgtctt ggcctcccaa agtgctagga  1320
ttacaggtgt gagccactgt gcccggccgt tttttttttt ttttttttttt gagacagggt  1380
ctcactctgt tcccaggct tcagtgcagt ggcaccatac tagctcactg cagccttgat   1440
ctcctgggct caagtgatcc ttccacctcg actcctgagt agctgggacc acaggcatgt  1500
gccaccacac tcagttattt tttgtattt ttgtagatac agggttttgc catgttgcgc   1560
aagctggtct cattttgaac tcctgaaccc attttgaact cctgaactcc caaaatgctg   1620
ggattacagg tctaagccac cacgcctggc tcagtgactg tttaaaactt tcctcttctc   1680
aaacataaaa ctgaatttct tatcctgttt agtcggtggc atccagtcgg tggcatcctt   1740
ggtcagctta ttaaccaatt cagaaaattt gggagtcatg cgagattcct ctctctgcct   1800
cagtagccac atctaatcag tcaccaagca ctgtccattc tatctcctca ggccttttgc   1860
atcttcctca gtatccttcc ccagtccact gccttagata ggctgtcatc tctcgcagct   1920
tgcagtttta caatgacatg taattaatct ccttgccctc caattcatct tccacattat   1980
ccctagacta gtggttctca gtggggtgtg attttgcacc ccaggggaca tttggcaacg  2040
tctgaagaca tttttggaag tcacagctgg gaaaggagga gggtggggag ttgcgggggg  2100
gtgtgatggg ggaacaagag gacttgctac tagcacctag tagtcagagg tcagagatgc   2160
tgctaaacat cctacaatgc acaggacacc cccactacaa caagaatttt ccagcccaca  2220
atgtcaatag tgctgaggtt gagagccctt gccctagggt gattcttcta aaacaaaaac   2280
cttaaatctc tcaaaaaaaa aaacccacta ttttatttta ggcaaaagtt tttgcatggg   2340
attcaacttt tctcattccc cagtcacaca gcatatactt atttttttttt tttaagagaa   2400
ggggtctcac tctgttgccc aggctaaagt gcagtggtgt gatcctagct cactgcagcc  2460
tcaaactcct gggctcaagt gatcctccag catcagcctc ccaagtagtc ggaaatacag  2520
gcatgtgcca ccatgcccag ctagtttacc ttttttttttt ttttttttttt tttgagaggg   2580
agtctcgctc tgtcgcccag gctggagtgc agtggcacaa tctcagctca ctgcaaactc  2640
tgcctcccgg cttcaagcga ttcttgtgcc tcagtctccc aagtagctga gattacaggt  2700
tcccgccacc acgtccagct aattttttgta ttttttagtag agatgggggtt tcgccatgtt 2760
ggccaggctg gtctcaaaact cctgacctca agtgattggc ccactcggc ctcccaaagt   2820
gctgggatta caggcgtgag ccactgcacc tggcctttgt tgtttgttt gttttttattt   2880
tagagacagg gtcttgctgt gttgcccaag ttggtgtcaa actcctggcc tcaagcagtc   2940
ctcctgcctc agcctcccaa agtgctgaga ttacaggcat gagccgccac acccagccag  3000
catatactat tactgcctga atatgccgct acctcctgac tcctgcctcc tgtcggctac   3060
ttgaagctta ttctgacttc ctcagactcg gctgggtgac tgtcttctgt gatcaccatt   3120
```

```
acaggaccgg gaatcactga attgttactt gcctgtctct ctgactgcat tgagcattca    3180
gaggtcagga acctagtcta ttttttttt ctctgaatct tcatcaccta gcacaatgtc    3240
tgttatagac gaacagatct aaactgaatc caggccctct ccccctgatt ccaccctgtg    3300
aacagccaga ttcgttcgtg ggcacaatgg gttcactgct gccttcctga cttttccttt    3360 tcttt acatc ctcacctgaa atgctgttct ttcacgtctc tgtctccctt catgtcagtc    3420
tcacctgttc tttatggtcc agctcaataa aaaccctac cacttcctga gcccatgcca    3480
tgtgggctat attatcatag ttccacttca gcaaaacccc tttaaggaag cattatccc     3540 tatttaacag gtgaagaaaa tgatgcaaac agccctgagg tgttgttcag agtgtggcag    3600
atgagacaag acttgcacac aaacacccac aatgcaggca acccggttg cctccctgtc     3660 tgctctgatc tccggtcttc tttggtcctc ttttctgtac ttctggaagg cactttggag    3720
atccttttgt ctgctgctcc actgagaatt gagtcaacta agaattgttt agggcaacac    3780
aggtggttac tggtggaggc caaacctcaa attcagtagt ctaattcgga tgcttgactt    3840
tattccacac ccagaatatc ttgctcagtt tcagttgcag taactcaagt gatcaggaac    3900
tgtccagcag ggttagtgaa gtcagcacag gtggggcagc ctctgtccac agccctgaag    3960
ctgcagaatt ctgaccgtgc acggcctcgg aggattttca tccagggatt gtcaggggga    4020
agtcgctgga gtgttttaag catgggagtg tgtggaacag atttgaattt ttaaaagttc    4080
attgtagaga attaattggg ggctggagtg aatggagtga cgatttaaga gatgttcgtg    4140
gtcccttcag gtgagagatg gtggcagctc ggaccgtgtt gccggaacat agacaagtga    4200
actgattgga gagataccta aggaaataaa attgttagga tttgtccgtg gactgcctac    4260
gaagtatgaa tcttggctac agtgtgacct tgattaagac actaaagact taatttgttc    4320
ctcatggata agatgatgct actactttga gaggttatta gtaaaaaatg aaaagcgctg    4380
tacatgcatt aggtatcagt gaatgtagtt ctaattccta ttatgcatat gcttttttt     4440 ttttcgtaaa gagcttttaa aatacggaat gggttggatc tgcagtagct tgtccaagct    4500
gggggctgta ttgttaaatt cttttttagtc tagtgctcca ctagctcctc tcctactgag    4560
ctggggtaag aagcggagcg tatacggagg aggcgggatg catttctgca tcgagcgcac    4620
aaaggtgtgg cggagggggc tccagagctg ggaggggtca atctacgggc gaatcctggc    4680
aattttactc cccgcgatag atgaccctcgc gtcctagatg agtttctaga ttctagaatc    4740
tagaggacgc ggtgaacaga gacgagtggg ggcagcttcg cgagcgaagc cggatggggg    4800
cggggcgggt aggccggagg cgcagagtct ccgccgggac cgcgacccccg ccccgctttc    4860 cggggctgcc gctggtgacg tcgcgagggg gtgggcccgg cggccacggg ggtggggccg    4920
gccgcggggc gggcggggc gggacgggag gcggtgcgtc gctgagcgca ggccgcggcg    4980
gccgcggagt atcctggagc tgcagacagt gcgggcctgc gcccagtccc ggctgtcctc    5040
gccgcgaccc ctcctcagcc ctgggcgcgc gcacgctggg gccccgcggg gctggccgcc    5100
tagcgagcct gccggtcgac cccagccagc gcagcgacgg ggcgctgcct ggcccaggcg    5160
cacacggaag tggtgagtgt caccggggga ggtggaggag ccggggcggc gcgcggtcggc    5220 aggcgagggg cgcgcagccc ggactggccg gaggcgcggc caccgctctt ggtcggtcct    5280
taggctgcgc ggcccggggct gctcctgagc gcagctcagg accccgcggc tcgggcgggg    5340 aaggcggggga tttccagccc cgcggagccg cgggcggcg aggaggtcgc cgggcggggg    5400
cccccggccg ggagaagagc ggttaagcca ggccgccccc tcccccagcg cgcacggcaa    5460
```

-continued

```
gttttcataa acaagcccgg agcgcgctgt ctgacatcct gtttatacca ccccgagata      5520
caggcgcggg ctggagggct gacgtcccta gctccttgta ccgcgaactt gaccgccagc      5580
tcccggccgg ggtggcagcg cagaaaggtt tcttcttcg gccccaggaa ggaggctgag       5640
ggtcttagct ttttttcctt cttgcggtct cagcgaggga agtttctgg gatttggagc       5700
tgggtgttgg gcgtccgcga actcgggaaa cgccccctcc cctcttaggt tctgttagga      5760
accaggcctc agtagccag cgagaagtgg gaaaggagac cctgggcgag aggaccaggg       5820
aagggaaca gtgggagaga actacccggg gaattgcgaa tcccactgga aagggactga       5880
ttaaccgaaa ctggggctgg tctctggctc cctcactcca actccatccg cgatcgtcg       5940
gcgaccggga gcatcggagg actaatagac actcctccaa agtcactccc cagggtccct      6000
gggatgtggg ctccttggat gtgtgtttac cacggaactt ctagataaaa gatgcgatgt      6060
ttgccaggtg tttgtgcaca cgtttttttgg agggtttgca ctccatgatt tcctgtgtgt    6120
tcctggggaa gggaccccg tccttcctgc cactcttctt actacgtggc tgtgagctgc      6180
cttctgcccc tggttgagta catcgctata catgtcattg acacttttcc ccccaagtca    6240
tagggttttt ctctcactgg caggaattta cagtggtata aaattgtcat tacttctttc      6300
agggagtaaa acatgggtag ttaagtgatg agaataatgc agagagagat gtaaatcagg     6360
gcgtgtttgg ttttggctat tttttttattt tttgaagaaa agatttgagt taaatatggg    6420
tataggcaca gtagatttg tttaagatga gcaattcgta ttgattgaat ctttgttctt      6480
ccctttccaa aaccccatta tgtgttgttt cttgattttg cttttggtga ctctgatgtt     6540
ttccaagacc aggggattat tttcattgaa ggatcaatgt gttcttttgt actttgtggt    6600
gaagattaat ggagaccacc agggttccag acatttctgg tacaatatgc tttgtaatgt    6660
ggagaaaatg tctcccctgt atagatccag atcacattta aagatgtgaa gacatcatac    6720
tggaatgact ttggacatta taaataggaa taatcataac ctcttcttaa ttctgtatat    6780
catattaact aagtgctttg actgagtctt agtttctgca aatagataca aaactatgtt    6840
tttttactgc taggattgca gtgtgatact ccacactgaa tacagccagt ttaaatggtt     6900
tcctccattt catactatac taattattta ctaccattgg gaaatgattg tagagaatgc    6960
ataaattaga tataggtaaa ataattcaaa catttcctaa aatataacta catttcagtt    7020
gttgtaattt aggatcttaa catgagcttg gctaaagcca tatacttccg actgaaacaa    7080
gcattgagaa cgtgtaggtt gatactcatt tgtgtagaga gaacaagaga acactaaggt     7140
ataactgcat agcaaagacc atgatctgtg ttttctaatt ctcagattcc tctggtgttt    7200
ttttcccctc aaagacacat cccatttttgt atgtccttat gtcctgataa gataatagca   7260
tgctgttaga agatttattg tctgagatgt gaatattcat acaaataaat ttttcttgtt     7320
cattttcaca tttaaaacca ttatttttaag tggatgggga attggcttat taatggaatc    7380
tcgctgaaga aggaacattg gatgttctgt gattattgtg gctcagtggt atatggaacc    7440
ttgtcattga acaggagtgt tggaaggaac tttcagattt ttttagacta gtaagggtat    7500
gattttgcac ccaatgagat atttgcagtt tctggagaca ttttggttg ttacaacttg     7560
ggggaaggga gcggtgctac tggtaggcat ctagtggtta gaggctaggg atgctactaa     7620
acatcctata acgcacaaga cagcccccca tcccaaacaa agaattatcc atctcagtag     7680
tgcccaggtt aagaagtcct gctttggaat actgagtaag gagcaagaag atctgggctc     7740
ttgtggcaaa tttttttcact tcagggcacc tcttttcttc atttgcaaaa tggagataaa    7800
aatattctcc ctggtcatct cgcagagttt tgggggaag tcaggtaaat aatgcatgga    7860
```

```
aactgtgacg tgctatgcaa atcataacta atatgaagag tattttttcat aagtgaatca   7920
ttagatttac cggtagttga gggaaccagg gttaaggcaa tatgttgagt aaaaagccgc   7980
ctgtggatgg tttgatatta tcgaattctt tgttattcat ttttttggggt aaaggttttt   8040
ttagtatact tagttttctt attgtcagaa catgtacttt ttagctctat aatttcttta   8100
agcaaaggtt attttttccca tcataacaat aaggagaatt cactatagaa aaattagaaa   8160
atataggaaa gtagaaaata gagggaacaa gtcattcatg ctctactcgc ttgtccattt   8220
aagcacactc acatccttgc caatttcttt tctataagag cagttaggat tcagagaatg   8280
atgagagaga gtagctggtg accaaggaag gtgttccttg tttctgtgcc cttcatttct   8340
ttcttttttta ataattacga tgtaaaggta aattacatta tagtaggcat cagagacatc   8400
ggttcattgt ttttattatt atttttattt ttcgagatgg tgtctcactc tgtcgcccag   8460
tctggaatgc agtggcacag tctaggctca ctgcaacctc tgcctcccag gttcaagtga   8520
ttctcgtgcc tcagcctccc gagtagctgg gattacaggc acgttccacc atgcctgggt   8580
aattttttgtg ttgtttttta gtagagatgg gatttcacca tgttggccag gctggtctag   8640
aacttctgat ctcaagtgat ccgcctgcct tggcctccca cagtgctggg attacaggcg   8700
tgagccaccg cgcctggcct ggttcattgt ttttatactt tccttgctgc tccaagcca   8760
tgttctcatt cagcttgttt cctctctgct tcttactctc ccccgtgctc agctaggtgt   8820
gccactgttg cttcctgtct cagaaaccct ctggttacat gggatttcaa acagctgtca   8880
tgttgaaatg actgggtttc agggaccgga aactaattcc tgtgagtatt ctttcctctg   8940
aggtgcacca gccttcttgg cagtttaagg cgacaggaaa gcataaaaca ttaagctcat   9000
ttccgtgata cctccacttc tgagggttta tgatccatga ttctttgtag ttggcagtgg   9060
gcacacattc ttccttggtg ctctgcggat aaactgccca gtcccgaggc aagacctgct   9120
ttagaagcaa aaggataatt tctttttaagt ctactctggc cagaagatag agctggcgtt   9180
tgttgggata ttttttaatct gcagtaactg aatttattta acagtactat tcacactagc   9240
attttataca ttctttttatt catttagcaa atacttgttg agctcttgca gtgaatctca   9300
gagagtgaat agacagacaa caaaacaggt acaaatctgt cctcgtgtgg aatttacagt   9360
ctagtggaag accctgaggg catgttcagt tttacagttg cagactatat gcatgtaaaa   9420
gagtaaatct ttgtgattgt agaatgtttc ctagaaccct tcatggcact cctttgaagt   9480
ttgaggacta ggaagtagct tccccttgtt atctttcttt ttttaatgtt acagattaat   9540
tcattctttg tatgcacaga catctctttg gtacctatta agtgcctggc agaaggataa   9600
gacatagttt atatggaaat aaacttggta tacatggctg taacacattg tgggtgatgc   9660
tgtagtagca gtcagaatta agagctccag gaccctgaag agagctaatt cctgcgtgga   9720
gcccttgtca aatgcttttt tgaagaggct tcatttgagt tgggccttca ggagtgagta   9780
ggagttcctt tgttttaggg tgggaaggaa gtctaggcag agatacagtg tgagcaagga   9840
cataaaagtg ggcatgtacg tggtgtcagt ggcagacttg gaagtggcca ctagattaga   9900
gcaaagactg cttgggaggg agcggaagga ggtagggcag gacatgcagg ttggatccag   9960
attgtgaaga ccgtagctct ttccacaaat ttgtgagcag tgttaggtta gggactgagg  10020
cctctgttga acgaatgagt ggggaagatg agaagccatt tgaagtttcc aagctcaaga  10080
ataacatcgt tagcaaatga agacctgaag cactgagagt tctatgaagg gtgagcttca  10140
tctgaccatt gtgcaactct ctcctccccca tcccagaaaa cgccttttat tatctgccat  10200
```

-continued

```
ttatcaacta tccagaagac tactaggaaa caagaaaggc ttcgagccaa gcaagatgtc    10260
atgaagttca tccatgcttt tcttacagtg gaataaaacc tactttgatt tgcttttaat    10320
ttataaagac ttttttttga cagtttatct aactggtttt taagccatta ggaaattaaa    10380
tacaagaaac ctaagaggca agagttgtta agtggatgaa tacaggaaga catgttctca    10440
gaggcaagca gtgttaattt ttatcttaga agtgaataag gagtttctac tggtttatga    10500
caaggagaac caaaactcaa aagtgaaaca atctggggca tttagtggag ggcaaacacc    10560
attgtcaaca agctagcaat ttgaggttgc attgttaatc acagcacagt atggtgtttg    10620
gtattggtaa tgatcatcaa gccatgaaga agaggtcaag ttgttgagca taatgaagt     10680 gaaagttcac atctctagca gaaaagggca acttcagatg tctcatttag gggttaggag    10740
gtatgtaaga aggtctgagg acaatataag aagctgcttt cagagaattt ctgtagacaa    10800
attcaaagaa gaggttttct tcagggtgaa acaccagtga ggaatctttg ctttaactca    10860
gggaagatta cttaagagtg agctgcgaga gaaggttgac tgtgaaacct aggaagagga    10920
gctgcggccg tctgcataga agatagtaat aacttgaagc cggctgtagg agactaaatc    10980
acatcaattt atggtacctc tgagtagaaa acagactgat tgattgtctt ttagccttgt    11040
tttgtttttt gattctgata gtctgttttt ggaggctctg gatctacact gtatgatttg    11100
atcctagctg tgagtttgca agcaagttac gcctgtttcc ttatccatag aatgacaata    11160
aagacagtac ctacctctga ggttgttttg agggttgaat gactatgctt aagattttga    11220
agtgatgcca gcatgagctg aaaatgtgct agctattttt acatttatt ttatttgag     11280 acaaggtctc gcgctgtcac ccaggctgaa gtgcagtggt gtggtcataa ctcaagtcag    11340
cgttgacctt ctgggctcaa gcaatcctcc ccacctcagc cttccgagta gcaggaacca    11400
cagacatgtg ccacaatacc cagctaattt ttaaattgtt ttgttgagag aggtttcatt    11460
ctgttattca ggctggtctc gaactcctgg gctcaagcaa tcctcctgcc ttggcctccc    11520
aaagttttgg gataataggc atgaaccacc atgcctggct tatttttt taatgattga     11580 taaataggat gtgtatttta aaaaaaaccc tcaaattata ttcagaatgt ttaacatagt    11640
agggaagatg ccaccagtag atacaaaaca aaaactaaca gatatattct atgttagatt    11700
tcagttagca atgagtaaat caaaaaagaa ggcagtttct caaatctaga agggtttatt    11760
acgtagacag tgccaaaggt gctaggtaaa ttaggtttta ctcttatttt taaggaaaaa    11820
tgactaacaa aggtgctttt atttaattta aagtgccatc caaggtatat aatttggtag    11880
gaatgtattt gactttctgg gaaagttaat gtgaagatac tgtgttgacc tcactgattc    11940
agtttactta gcaagttgtg ggctattggc agaggcacca tgtatacctg tttgtaaaac    12000
ggtgtcttca gagttgtgtg gaaattaaat atcttgtaaa tcagataata ctccagggag    12060
ttttgctggt aaggaattat aagagtttaa agggactctc aaatatgtat tcagtttcta    12120
tggaatgccc ttttacagtt tctgtttcca taaacatatt ttgctttcct aaagcaagat    12180
ttacccaaaa tgtaaaagtg tgcaaagagt tggccccttcc tcctaatcat agatgtgtgt   12240
tttaaaatat tttaaatgta tttccttctt ggtgatgtat atgttggact ggtttcttgg    12300
gtctgggcat tatttatact caagaacagt tgttgccacg tgattggaaa agcgctattg    12360
atgtcattct catcccatat gctttgacag caaaggagtt agctgtatct tcccttgtct    12420
tcccactcta gaatgagaaa gacaagaaag ctccctaatt tgatttgtat ggaggggggag   12480 tgggtaggaa agtccacttc agctgaaaag gctgacctgt aggtatttaa aacataaatt    12540
taggtctgtt atttttcacat acacttggta actcagactg gtctgaatat aaagtagaaa   12600
```

```
tagctaagaa ccatttgtaa tgaatgcaac tcttatttgt ttttaatggt gttttaagga     12660
cttaagggta ttagaactga caacagttta ttcagttaag cacaatttta tctggaggct     12720
tgcttgcaca gttaatttga tcaggttgta gtaaggctat ataacagttt ttttcaatta     12780
tgatttaaaa taatgtttat attgtactaa gagaaaagat aacagaaaac aactcaagga     12840
aaaaataatc tgccaaatat gtgtctttcc agataaaaat tttgttatta aactagtttg     12900
gtggatcaca cacagggatg cggacagatg caatatatat tataaagaaa gaagtacaat     12960 ggcttttttgc caggtgtacc tgcaaaccca ttttagcact aattcacata acatagacta     13020
aaaagtaata tgctaatgtc ttaatttaat attctgactg attttgttca gttaaaacca     13080
ttctgtaaaa cttaaggcaa gtccacgaat cacagtatac gggttatctt tttgggaaaa     13140
tcatttgatg tatggtggta actccaagga acctcatgtt tttacttgtg tagaacgacc     13200
attcacttgg gttggttgga agtaggaaga agtcagagga ggtcatattg gcccaaacat     13260
aaattgtaag cccacttgat gtgatttagg aagcaggcca cctaccatct acaagctggc     13320
tgaaatacaa atgctcttag gttttcatgt ttgttccttt attcagcaac tctctgtaga     13380
tctcactgta tgtgagaaca agatgggctt ggctcctgcc cttagaaaag ttccttgcta     13440
gttgaaaaaa caattcagca attatattac tgtttgttac agtgatgctg agtaccggga     13500
gagatgtcag aggtgggttg taagaaaagg gagtctttgc agtacacttt ttttttttt     13560 tgagacggag tctcgctctt tcgcccaggc cgggctgcag tggcgctatc tcggctcact     13620
gcaacctctg cctcccgggt tcacgccatt ctcctgcctc agcctcccaa gtggctggga     13680
ttacaggctc ccgccaccgc gcccggctaa ttttttgtat ttttagtaga cgggggttt     13740 caccatgtta gccaggatgg tctcgatctc ctgacctcgt gatccgcctg cctcggcctc     13800
ccaaagtgct gggattacag gctcccgcca ccacgcccgg ctaatttttt gtatttttag     13860
tagagacggg gtttcaccgt gttagccagg atggtctcga tctcctgacc tcgtgatccg     13920
cctgcctcag cctcccaaag tgctgggatt acaggcatga gccactgcac ccggcctgca     13980
gtacactttt atacatggaa atctgaagtg tgaaagagct gtgccaagag aatgaggagg     14040
atttccagtg agaggcacga atatgtgcca aagacctatg gtgggaccaa cacctgcag     14100 ctggtgcaga gagaacaaag gtggaggctg gtgaggcagg aaggaacctg gtcaagcagg     14160
gccttatgtg ctttattact tttgggcctt ataatgcatt aggggaagtt gaagtttta     14220 agcagggtag taacatgatg agatttgtgt cccatgaaaa aacggaagga tcccatccac     14280
tcactgttgc ccctagagca cctctcctct ctttcctctt tcccttcatt ctgctgccaa     14340
ataccttgaa aaccttcact tcctcccacc cactcattct ttaaccctt gcaaactgac     14400 tgccacctct acactcatga gactgcttcc ttgaggtcac cagtgacctt cttgctgtca     14460
cattttaaca cctttttttct gccctagtta tctaaaacag ttcatgctgc tgaaaacctc     14520
cttcctggca gatgtccctc aaccctactg gtgcctggct tctgagacac agtaaggact     14580 tccttttctct gtatgtctct gttctctttt tgagtatcgt ctctttctct cacttctcct     14640
cctcccccaa tgaggatgtt tctaaaggtt ctgtgaatgg tagatttata tgttgcgaaa     14700
actgtgcaga tgacccactt ttgcctgagc tccagttgtc ccttttatt tattttcctt     14760 cctctctgct ccttacctcc cccaaatact ggttgcacag tttcagacac tattcaaggc     14820 actgggaca ctggggaaca agagaggaaa ggtccctgtc cttaagtagc caacagtcta     14880
agatgttaaa cacattgata aacaagataa tttcaggtgg tgataagtgc aatagagaaa     14940
```

```
gttagcaagg tatgggtagt gaatgcttag gttggggggt tgggagaagg gctcctggtc    15000
tgagaaagtg acatttaaat tcagccctga aggatgagta atgagtagaa gccaggcagt    15060
gcaatgatct gtaagaaaaa tgtactaggc agaggggata gccagtgcca cgccccttca    15120
gtgggatgag ctttccattt cacactgggc tgccttgctg tgtgtccttt gacacctccc    15180
atttaactgc tccaagattg ataccgtctt tctttctgac ccatcatcat aataatggat    15240
gatttctctg ttttggttaa taccgtctct atccaccacc ctgaaaaccc taggccagca    15300
gtctgaaaac tttgtgaggg gaaagacagt aaacattttc agctttgagc acagtacagt    15360
ctgtcacaag tactgaatct gctattgtag caccaatgta gatatagaca gtatgtaaac    15420
caatgagtgt ggctgtgctc aatacaact ttatgtatgg acactgacat ttctattttc    15480
acttgtaaca aaatattttt ctttttttc caaccattta aaaatgcgtc agcttattgg    15540
cgttcaaaat gggcagcggc aggccagatt tggctcacag gccaggatct gctgccccct    15600
gccttagact aaccctgatc tctccctttg cttttgcccc accccacctc ctccctaggc    15660
cctttcaggg ctccctccct ggtattcgta ttcagcacct tgccactcg ctgtccccac    15720 tgctgcagcc ttcctttggc tttctttacc tgggtgatct atcattgcgc actctatgtc    15780
catgtgcaga cattatttag ctcccacttt aagtgagcac atgctgtatt tatctttccg    15840
tgtctgacta ctgatcacaa gcctttagaa gccctattg cctatagaaa acaatccaaa    15900 ctccaccta gtctgatagt aaaggttcct tatgctaaaa cctcagttta actttctagc    15960
atactctcct atttctctcc ttctacactg tcccaaaata gattattcat tattttgctt    16020
tcaatgtttc ccatgctttt ctgtgttctt gttcatttaa tgcactttc ccgtgcttca    16080 tgctttccat ctgtcagaat tccatagctt tcaaggcccc ttcaaatgtc cctggtctct    16140
tcctctgccc ctccctaccc caacaagcgg tgtgtataca catagtcccc tggtggtgtg    16200
tgatcctctg ttccagtacg tcgtgttctg gtctgtgctt ctgttctttt gcagacacac    16260
ctccactatg cagtcacgag gcccttgagg acaggaacca tctctttctt cgtaatgtca    16320
cctttcccag taggcacacg gctgtttatt gaataaacac agatcctgtg tacacttgct    16380
caaattgtac aaaatttgca ggagattcaa agtggaaaca ttttactgaa gggaattcgg    16440
tcaaattaca tccttgattc ttgtataggt ggtacagttt tgtaaaggat catcaagtat    16500
tttggaagac tcattggctc tgccagtggc ttagataaat aaattcgggc aagttattga    16560
tctctctcct cagagaaaaa aattgatgtg ttttctttta tataaagaga aaaagaaaaa    16620
gaaaaaatgt gatctgtaac tcattatgtt tccttgctag aaagctcaaa gatacgttat    16680
ttgcctgttt ttagttgcta tccagttttc ttacaataat ctctctgcct cagtctcctc    16740
atcggattac ttgtcacatg tgttaaatcc ttcttttaat tgatggttct gttgtatata    16800
tcttttatat ttatataggt agcctcaact ctccttttt tggagagtgg taatagaaat    16860
ataaataata aatagttgcc ctttggtttc cccaacctgt ggtgacaaca agataataaa    16920
acagatactt atcctatata aaacaggcaa aaaggctttg ggacaatatg ggaatcatga    16980
tgtgggtttg gtggaaaacg agcaaagcac cttgtaagga tcttgtagtc tgaagattaa    17040
ggtgtgcttg gggtaggtca tgtcctccca gctctgtggg atttgtagca catcatccca    17100
cgtggggagg agagtgggca cgggcatgag actatttatt agcttttact gtgtcagttg    17160
ttgggttatg tattttgcat ttgatattta atttaatctt tgtaatagcc agagacttgg    17220
atcttattgg catcattttc cagatgagca gagctaataa atggcagaac tagaattcaa    17280
atctgaggct ctctggcatt gaaaacaaca acaaaacatg tttctactct tcaaagagac    17340
```

```
tttttctcct ggattgtcac ttgtcctttt ctttctcttt ctctcctgac attggtattt    17400
aaaatgagaa cctaggaaac ttgtttcttc taacctaatg tttttgaagc agttttaggt    17460
ccttggagat gtgccttgat gtgtctatac aatatagtat ttggtattgt tagatataaa    17520
gaagacctga ggccgagtgc ggtcgctcat gcctataatc ccagcacatt gggaggccaa    17580
ggcaggcaga tcacttgagg tcaggagttc aagaccagcc tggccaacac agtgaaaccc    17640
catctcttct aaaatacga aaaaagaaa aaagaaatt agctgggcgt ggcagcacgc    17700
acctgtaatc ccagctactc aggaggctga ggcgggagaa ttgcatgaac ctgggaggca    17760
gaggttgcag tgagctgaga tgatgccact tcactctggc ctgggggaca gagcaagact    17820
ctgtctcaaa aaataaaaa aaattttttt gttttttagg ttttggggca gggcagttgg    17880
gttcatttag ctgtcctaaa gtaagtttgg tatattttg tgaaatattt agtttaaaag    17940
ttgtattgct gttttgaca ttttaagtca gacgagattt actgttgctt tatattacct    18000
gactgttata taacacgtcc tgtgtttacc tgtgtgggtc tgagcgtacc agatgtggtg    18060
ttatgaaaag cgtgctggac ttggaaccag gacgagccga tgtgaggctg tcctctgcca    18120
cttactagct ctgtgacttt gggctcataa ttgagcctta ttttttttctc aattgtaaat    18180 ggactgtgta gacctgtcac agaggaagtt ttgtgaagct taaatgaggt agaacctaca    18240
aaatagcttc agacagtgcc tgggatccag cagcatttaa cgaaagttac ccactgctac    18300
cccaaatact gaatattgcc agaaaatctg taaatgatta cataatgttt acacctttat    18360
aagtggtaac tttgtaggta aatattattc aagttatgaa cctctgatt aggaaacctc    18420 cttatgcaaa tggttggctt cccactacag aaacatcagt aataagatag tggtttagac    18480
tcccaaatct gcgaccagtc tgtatgttt aatcctggct tatgatcagt catagctgag    18540
tgatcgtggg caagttattc aaccgctttg tgcctcagtt tcctcatctg taaaggata    18600 ataggataat aatggctcct accttatggg attgtgaaaa ttaaatgaga atgtgtgttt    18660
atgtatgtgt gtgtttgtct gtatttgtac caatacccta ttggagttta ccactattat    18720
ttactgttcc tcttctcttt tcctcccctgt gtaaacagcc ccataagtta tctggaagtt    18780
ccctagtatc tcttcttat cttctgttac tggaagactc ctttttcttc tgtctttggt    18840
cccgtgttag ttgcttcatt ttaattgagg ctatcttgtt ctagtgtgca atacattctc    18900
attgatccct tccctataca tttcttgcct agacactttg aaaagtgtt tttgttttgg    18960 gtggaaactg aacattttct aataatgact cataaaccca gccaggtgtt aaggatactc    19020
ctatatcaag gaaaatgaaa gctatacagt ctcaagcaaa tgaaaaaact atataaaatg    19080
cctaattgtt tattgaatgt ttatgccaga aattcagatc aataaactga gccttagaat    19140
ggttgatgtt taaaggtacc cggcttttaa gtggaggaac ctagatttga tcaaagccag    19200
accaacctgg cccttggttt cacaatccct aagctcactt gccttaataa ggcctctagg    19260
caccacctca agactccatc tgcacccctt atgaacctac actctgcttt ccctcacact    19320
cctgcttttg agatggcaaa atcacttatg gttcttttg gctgcagtaa tgtttcctgc    19380
tattttggca gggcaaatgt atagcgtttc agatacttta tgtgttaaat tggccttttg    19440
tgtgttggct tggaaactta accacattta ctgcagtgtg tctgggggaa atgtgcgcca    19500
agtttcaaac aaccaactgg gaatgaattc tttaaaaggc agaacttgtg cctggcgcgg    19560
tggctcacgc ctgtaatccc agcactttgg gaggccgagg cgggcggatc acgaggtcag    19620
gattcgagac catcctagct aacacggtga aaccctgtct ctactaaaaa tacaaaaaat    19680
```

```
tagctgggcg tggtggcggg cgcctgtagt cccagctact cgggaggctg aggcaggaga   19740
atggcgtgaa cccgggaggt ggagcttgca gtgagcagag atcgagccac tgcactccag   19800
cctgggcgac agagcgagac tccgtctcaa aaaaaaaaaa aaaaaaaaaa aaaaaggcag   19860
aacttgttta tagctaaggg ctgctggtgt atttatttga gtgtgttacc tgcattggta   19920
tgctttaagg gcttctgtgt catgcctgaa gcgacatatt ctggaatgta tacattattg   19980
cacttccttg gttaattgtc ctcactgttg ctgacctttg tacactgaac cactgccatt   20040
gtgtttggca cgtagtagga accctgtgaa gagacttatt tagtcctctt taaagatcaa   20100
tggttcttta tacttttctg tatgcttgat atatttcaat ttaaaaaaat cagtggagta   20160
aggaaggatc aggcaacatt gaaagaggaa tattgccaca cagttgccaa tctgatgaaa   20220
atactgctta tgctaggtcg aattgagact ctgaaaggta tttgggagcc agacacttat   20280
gagaatacat attgctttga atattggaag aaagcaaagc agtcaaacga atttcttctt   20340
ggcttggagt tttgtttact tttctcaggt tagaattgat agttctaatg gttttaagaa   20400
gtcatgagaa acaggcccac catgaacctg aatatttggt tctgagttta tagccattgt   20460
ctagtaaata ctgtttaagg gttattagca cacaatgatc ataaaatctt gtaatacttt   20520
taagaggtgt aagaaattga agtcacctga gaatacctcc ttctgatttt acagtggaga   20580
aataaaggaa tcagagtgtt taagtgactt gcctaagacc tgtctgggcc accactttag   20640
ggattgtttt ttaatccatc atcatgctgg atttgttact gagcgataaa atggtacaga   20700
aggtagtcac atagagaatt taggaaataa aatactcatt tgttcaaata cttctcagga   20760
ggttgagata tatctatggg tagaagattt agaggttatt taagagaaat taggattgtc   20820
tagggtccac cccttaccgt ggggattctg aagggcagtg tcttatgaga gaagagagat   20880
caagttactt ggtgagtgag atgttctagg tgctcagtcc aagggctggc cggatggcta   20940
gcactgaact tgtgtggatg tttgttcaaa ctaatcagcc tacgattggt ttgttcctaa   21000
gaatgataaa actttgttct agttttttaa attgtaataa taattctgta agcatttaag   21060
aagaatgctt tctttaatgt tgactttttt tttttttga cagagtctt tgctctgtct   21120 cccgggctgg agtgcagtgg catgatctcg gctcactgca acctctgcct ccgggttgaa   21180
gtgattctgc tgcctcagcc tccagagtag ctgggactac aggcgcccgc caccacgcca   21240
ggctaatttt tgtatcttta gtagagacgg ggtttcacca tgttggccag gatggtctcg   21300
atctcctgac cttgtgatcc gcccgccttg gcccgccaaa gtgctgggat tgcaggtgta   21360
agccactgcg cccggcctaa tgttgacatt ttttactcct acacgaagct gttatgtttt   21420
tacttattct tttctagtct ttatcgataa tgtataaata tgtactgtat tatgtaatt   21480 taattgctgg atacatatac ctgtcttctt aaactttttt attctatttt aatagagtct   21540
ttgtaataat cattttgaa tgtagtattt agttgtgtta atttattta ttttctta   21600 gtaatctatg atagaataag ctatttctgt ttttacagaa tattgtaggg aacctttaaa   21660
aacacacaat tagcattttt ctgctgctaa ttgctttatt aggatgaatg catagattta   21720
ctgtgtcaaa ggttataacc aattttatga cctttagtat gtaattctgg aaaattaaac   21780
agaaacttaa gtcacaaatg gccttaaaca tggcaggaa gctgctgatt tcctgactgt   21840
tgtacaggca acccactggc aagtaacatg tcaaatacgg accattataa ttccttatca   21900
taaaggcaga tacagttttc ttcaaaggac atgaaaataa tttatttgct tttgatgcct   21960
tttctcactg ggaaatgata ttctgtaagt gcacaatgtg cacttgaatg tgaagttgta   22020
gtgaggattt ttatttttat ttttgtacaa ctgggttata ataaaggaaa caaactttat   22080
```

```
gtcacttcta ggctgatgaa atacectagt aaatgcagta catttttgca tgactaatag    22140
gagtaggggc ggggctttga cttttacatc agtcaggtta aaatcacctg tttgctggtt    22200
tccctaagac agtgatgtat tgcccttgc ttaactttt gttagttggg aaatgtattc    22260
tactttgatg actggtgttt ttctgcttag tggggatatt ttctgtgaag ccaggataaa    22320
caattctata atgcaaatct gaacacatca ctgccttgct taaaatcttt cactagctgc    22380
cctttgctgt taggattaag tctatccaaa ctccttagca tggtatgaag agcctctcat    22440
ggtcacagcc ttccttcct tccattccct tcttgcagt cagcactcca gcccttctga    22500
ccgtttttgt ttcttaaaata tattgtgatc tctcttactt ctaggacagt aagttctgta    22560
gattccttgg tgaatataca gccttagaga ctgcaagaat tctgagcagt atttctaagg    22620
gttagatttc cctccaagta ccattaacat tctgggctgc cacatttcaa gatttactct    22680
ggagatgtga ggtggaagcc atgttaaatg gctggaagat agtcctgtgg gagagataag    22740
ctttatcatt ttattttac caggtgtgtt gcagtgagtg ttgaaaagcc ttccacaaaa    22800
aatagagtct tcttttttcc cctgttatga ttaaattact ggctgctaat ctttcatgat    22860
gaagagagaa gcccaaaagc aatttcagaa catggatctc atgctgatta gtggttataa    22920
tgatttcaca tggatagtat tccttgtgtt tgaaagttat tttattggtg agatctgcga    22980
aatcaacaag gctagtttat cttgcaaaa acttgtgaca agcttatagc tacactcctt    23040
ggggaacaca gttcacattt aagattttgc ctcaggcacc tctgttcagc tttatgctgt    23100
gtctttcaga ttctagatat gaaactggtt tgacattaat acctagcatg atagcttttt    23160
agatacactc tttgcttgca ttaagtcaga caaaatctgc agagcctagc actatgctca    23220
gtatatgagc tgctttgtct gtgtatcttg gttcatacga gagtcagtat acctaggcag    23280
tcagtaaaca gtcattgatt agatttggat ttaataaatt taagcctggc caataattag    23340
tgggaaccaa accaaggcaa cctatagtaa atggagcatt gcatcgaaga tctcagttct    23400
tcaaataagg cacagataaa ggatctctat gtattacect cctgttcttg gatttaattg    23460
ttcaaatgtt tcacccaaaa cctcaatttc aggctaatat ttaggcattc tcttctatgt    23520
tatacctcag gtaatttgga aacatttgta tttctaaatc tatttctgta taaactttct    23580
atgaattgta tatctctccc tctctatatt atatagtata gatttaaatt gaaaaattca    23640
ttgttccctt cagaggtata agagtattct ggcccagctg gaaatgttat gttaaatttg    23700
aaattctact acctaaattt tggacttgtg tactactgtt ttagtagagc tatatgatac    23760
tgcagataaa gttccaaaac aatctgtggt gaaaaaattc ttgttcaggg acctgttgtt    23820
cagtgaaact gcttttctgt tgggtacctg tattctttt tggttaagtt aaaaaaaaaa    23880
aaggatttat tggcctatgt cttaaggggg ttggggagg acccatggtt catggactcc    23940
aaggatataa aggcattccc cttctcagta agaatcctgc tattctgctt cctgttcatt    24000
ggtcttatgt tctgccacaa tgaggtttta tccacatgat ttgaatagag aacagttggc    24060
tgctccaaga tgatgtctgt ttatcaaatc tccctgaaag acttgtgttt gtgtcaccct    24120
tggtctggaa ggtggacagt gcaggcatgg atggggtca ggtgggacac tgtgatctgt    24180
agtgttaaca gaatcacctg gtatgagaag tttctagaga gataaaaaca gatgtcagct    24240
gtaatatatt gaactggcag ttaaaaaatt tttttaagt tgtggaaaat aaacaacata    24300
aaatttacca tgtgagccat ttttaagctt acagttcagt agtgttaagt acattcacgt    24360
tgttttacat ctaatctcca gaactctttt catcttgcaa aactgaaact ctgtacccag    24420
```

```
tagataataa ctacccattg cttttttcctg ctagctcctg ccaactacca ttctactttt    24480
tctatctatg gatttgacta ctctggctac ttcttataag tggaattgtc cataatgtcc    24540
tttttcacta gcatgtttca cttagcataa tgtcctcaag gtttatccat gttttttgcat   24600 atgatggaat ttccttcctt ttaaaggctg aataatattc cattgtatgt atatacaaca    24660
ttttgtttat ccatctatgt tgttggatgc ttgggtggct tctaccttttt gactgttgtg   24720 aatgatattt ctatgaacat gggttttgcaa atatctcgtt gagaccctgc tttcagttgt   24780
tttgtgaact gccactttttt tggataactc tcatttgaaa ctatgttcat ctttttttcc   24840
ttaaaaactg cccgtaatta actctttttg gtgcccagta agtggaaaat tcagaacagc   24900
aaaatgtttg ctttattcaa caaacacctt ctcaaaatct agaaacaaa gaacattaga     24960 gaacactgtg gaagtaagta tgattgtggg tagctggctg acgtagaaga ttttaatttt    25020
tactatgatg cataaatatg tacctttgca agttttagca gacaagagca tgaggtccga    25080
tcatagacct atgactttgg ggaagttacc taaagccttg ccagccacca tttacttatt    25140
tgcagagagg gggttggtta tacctgctag ggttaattag actattaaat gagataacat    25200
gtgcagaaca catagccagt ggtaggtggt cagtaagtgg tttcctctct cctgtattct    25260
tccaggggaa tagaagacga ccactgtgtg aggatctctg tattgttcag ctctgatgct   25320
cctcctactg tgggtggtag atctccctct taacaaggct ttcttggcaa gcatttttaa   25380
actttacatt ttcttatttt tttattattg ttattgatat tttgtttggc ataggtactg    25440
tattgacatg gttcagaaag caaaccaggg ccgggtgccg tggctcatgc ctgtaatccc   25500
agcacactgg aaggccgagg tgggtggatc acttgaggtc aggagttaaa gaccagctgg    25560
ccaacatggt gaaaccttat ccctactaaa aatacaaaaa ttagctgggc gtggtggcag    25620
gcgcctgtac tcaggagtat cccagctact caggaggctg aggccagagg atggcttgaa    25680
ccctggaggt ggaggttgta gtgagctgag atcacaccac tgcactccag cctgggcgac    25740
agagcaagac tctgtgtcaa agaaaaaaaa aagaaagca aaccagtata acagggtaca     25800
aattgagaag gtttgctccc attttttgttt gtccgtcaac ttcgttccct gtttccttaa   25860
gtgctcttct catctctagg acctattaat gtaagtatat attcgtattc tttttttttat  25920 tgtacataag gtaaatatat actatatact attccaccct ttgcttttttt cattttacca   25980 tatatcctcc tctcttttcct tattagtaca tcaagtattt tctcgtgtga atagaccatg   26040
acttatttaa ccagtcccca tgtaagggac attttgtttg cttctgcact tttgctgtta    26100
taaatagtgc tatttgtgta actttgtatg tagaaggtca gataaattcc cagaagtgga    26160
attgctgggt taaagataa ttgcattaat aattttttatt aatattctca attgctcccc    26220
atggggttag tacctttttc catgccttga aatttacata tttttgtgca ttgcagacac    26280
ctctcacccc ttgctgtata ccttcttttg aactgccatc ttgttaacat ggagagaact    26340
ggcaagtgca ggcgattcct tcttgtgttt cgtaagggct agtggactgt tggagtgctt    26400
tccaagcagg tgccagggtt tgagattgta gtgtgatatg cgactagggg ttctgcccat    26460
cccgatgtgc tcctgttccc gtctcaggac ctgaggatgg aatggctgag tgtgttgtga   26520
gcccaaggtg ccaagtgctt ctcggggggag aatcagttgc tctgtgcatt aaagcagtat   26580
tggctgctgc ctcccttcct tggaagtttt tgttctgttt ttttaatttc ataacttttt   26640
acaaaagtta ttcctatttta ttgaagactt agaatccaga gaaaagacaa aaatcacttg   26700
gactctcaca acctttgtta atattttcac gaatatcctc tcaatcgtgt gtgtatcccc    26760
aacataaatg gtggttatat actgcataat gtttcataac cttttttttcc atttgctagt   26820
```

```
gtatcatgac tattgtaaca tctttcagta gtgatatacc cctgccccca acacatgcac   26880
atgttttgtg tagatttcta ttgggtggct tcaccgtgat tctgtgttcc tggatgaaca   26940
tttatgtttg tcttgttagt caacaaccct acgatgaaaa tccttctggc taaatcttgt   27000
atgttattat tgtttgctta gaatacattt ctagaattag caaacaataa taacatacag   27060
gaattagaac ttctaggtca aaagacatgt acacattgct ctccaaaagt gacatattat   27120
ttatattcct aaatgagagt accactgtca tcatactcaa tttgtggata taataatttt   27180
ttaaaatttt ccaatttatt agtaaaaagt gataaatcta tcttttactc tgtagatatt   27240
taattactgg tacatttaaa ctttttttt ttttttttt tttgagacag agtcttgcac   27300
tgttgcccag gctggagtgc aatggtgcga tctcggctca ctgcaagctc cgcctcctgg   27360
gttcatgcca ttctcctgcc tcagcctccc aagtagctgg gactacaggc acctgccacc   27420
acacccggct aatttttttgt acttttagta gagacgggat ttcactgtgt tagccagcat   27480
ggtcttgatc tcctgacctc gtgatccgcc tacctcggcc tcccaaagtg ctgggattac   27540
aggcgtgagc cactgcgcct ggcctaaact tttttttttc aagtttgaga actcattttt   27600
ttgatgtgga ttgcctagtc aagccctttg ctcattttat tactggcgtg tttgtctttt   27660
ttttttttat ttattaaagc tacatatgtt aaggatatta gttttctgtc acatatggta   27720
caaatatttt tcctcaagtt tacttatata ttaagaacct tttgttatag aagttttata   27780
ttttcatgaa ctcacatcaa tcactcattt ctttataaag gcttctgctt ttggtgtcat   27840
gtttgagaga ccttttgatg cctctaattc tacaaatatt taactcttag acttaatatt   27900
tggtatattt gtcatttgaa atgataggat gtttatttta gtctatgatg taagagggat   27960 tctaattttta ttattttctc tgactatcca gttgtcctac cacaaaaaat catcatctcc   28020
ccactaactt gaaatccatg ttttttacaaa ttgctttttt gttttttaac acattcgaaa   28080
atttacacta aaactctata aaagggcat tagagtcaca aggtcctatc cctggactgt   28140
tttcaggcag ttgatgccag tgagacattg aagaggtggt ctaacctctt cttagacttg   28200
gtttcttctg gggattcaca cctgaccacc aatcagggtg ttatggtcat ctgatgaggt   28260
aataggtatc aattctgaac cattatatgg gaagtaatct ttatagtgct actaattagg   28320
agagcccagg tattcctgag gaactataac catagtcaaa atttgatata ataaagttta   28380
gttattgtct tttggaagaa ttaggaaaac taaagaaata acttctctga cttttgagtt   28440
atttcccatt agccaaatag ggcctaattg taaataataa aaatgggcct gttttaatta   28500
tttatcttga catggattaa atatagtatt taatttcctt aatgattaaa tatagacagc   28560
aaatgtaatg ctgtactttt cacatgacgc aattcatttg gcctttttct tttttaaaa   28620 aaattaagac agttacttta tttagaacag gaaagtggtg taagcaactg agagtgtgcc   28680
ctgtaatatg agaggttctt ccctcgttct acttcccacc ttaaaatata attttaggag   28740
aaaaaagtat cttatatttg gttaattatg ttatctacga ttcacccttt tgctaaggca   28800
ggcatggcat ttgctgatgt ttggcttgaa gtctaagaat attgtccaga tagaacatgc   28860
taaattgtta catttgagtt aatgttgaat acttgaacta acatagggat gccagaccac   28920
tactcttgat ttaattagag atttgtacac attttcagtt ttttccatgt aagatcagtt   28980
ttattgttcc tttaaaaata ttctgatgaa ataatcttgc aaaggaaaga taacctagca   29040
tcaagtctgc gatataaaaa caaaaataaa atgattttct gatcagttat catgtttatt   29100 accttttacaa atagtgtatt agtcctttag agagccccac tatgctgcct gtgccaaaag   29160
```

```
tgtcatgtat tgtccttgag tatcaaagtg gttcataccg gttatctagc aaagggccag    29220
attgtctctg catagtactt ttcatccaga gtgaaatgat gataaattcc cacacgaagt    29280
atatgtatat ctttttctcc ctggcaattc agatccatgt gtcctctata tcttttatgt    29340
caaaatacct acttccatcc aagatatatc gaatttcatc attcaaatgt aaatgtttct    29400
cataagacat catcttttcc tctaatttgg taatttatct ttgcatattg ttattatgtt    29460
catccaggag tagtttctct ctcttttggat ttttatataa ttctggatcg ttcttgtatt    29520
tgtcaggaac aaccaagctg acacagtcgc tccaggccga ctgggctcca gtcggtaggg    29580 cttctctag ggctttctct ggggatctgt agtgtaaacc acacctgcct aatcttccct    29640
gcttctccta gagaacactg gaaagtccca ggggacactg gcctgacctc aggcttttcc    29700
tttggtcttt agattcagac atttccacta aacttagaga gtcaagtacc tggattcatg    29760
ttgaaaatct gatagtagtt gactttgaga cccaggttta gtcatgtcat gtgctgagct    29820
ttggtttctt cattttcaaa atgtaggccg tttgtgggag tttgaatgta acatcacagc    29880
tctgaggttc cctttccatc cccagttttct ctgatagagc agaggactct gaaggaggc    29940 cagtttttt attctaacca tgggaaattt gaaataattg ttgacttctt ttgcttattt    30000
tttttggtcc ctaaaatatt tgattggtca agataaatca tctttgtttt attttcatt    30060 tctgataatt atcagaataa taactggata agtcccagtg aaagccccaa ctgaaagaat    30120
ttgtagtcat gttgtcacat tttatattta aaagtgtttc tctagagtta aggaatgaat    30180 ttttttttc ccagatgtgg atgcaagtta caataaattc ttggcccttt tgaaccatta    30240
gggattaatc attttgggtt aaccatttc tagatggtga gaatttattc ttataataac    30300
cacaaaactt caactacttt atttattt tattattatt attttgagt tggagtccat    30360 agcccaggct ggagtgcagt ggcacgatct ttggctcact gcaacccctg ccttgcatgt    30420
tcaggtgatt ctcctgcctc agccttccaa gtagctggga ttacaggtat gcgccaccac    30480
gcctggctaa ttttgtattt ttagtagaga cagggtttg ccatgttgct caggtgtgtc    30540
ttgaactcct gacctcaggt tgtccaccca tctcagcctc ccaaaatgct gagattacaa    30600
gcgtgagtga ctgactgcgc ctggccaaaa ctttaactac tttaatgaaa aaatccgaaa    30660
atatattttt tctgttcttg aactgaagcg actgaataca gtttattttc tcttattaa    30720 tcatgttcag ctacaaatgt aatttgtgtt gagcactgtg tttatggagc atagcataaa    30780
ttggagtaga aagacctggg tttaaatttc accacctact gactcttgcc tacgaacagt    30840
aaacccgtct taacctcatt ttcttcattt tttaagaaat tgaaattgag ccaggtgcag    30900
tggcttatgc ctgtaacccc agcagtttgg gaggccgagg tgggcagatc acttgagccc    30960
cagaattgga gaccagcctg gccaacatgg tgaaactcca tctctactaa aaatacaaaa    31020
attagccagg tgtggtggca cacacctgta atcccagcta atcgggaggc tgaggcaaaa    31080
gaatcggttg aacctgagag gcagaggttg cagtgagtgg agattgtgcc actgcactcc    31140
agcctgggca acagagtgag actatctcaa aaaaaaaaa aaagaaatt gaaattggta    31200 taagctaggt cttctgtaaa tgatgactct tacaataggg attccctgca ggtctgttga    31260
gttatgtgta tttgcatgca catgtacaca cacggtgtat ttgttccata gtaactagct    31320
ttggacttcc tgttgtgcct tctattgttt ttctgtcaac ttaccggttt tctctccttg    31380
aagctatcag tatgcctgtg tgtagtgcct gctctcatag gatttatagg tttgttgaca    31440
tctagttact tgtatttat acacagctct aagtgagaag gcttggcaat atgtaatgtt    31500
cgtgaatatt tgtatgaaat tcagcagcat ttactttggg gaactcatat tttatgtgtg    31560
```

```
cttcaaaaca atgaaactta gcactattac aacacaggag tatatttgca tcctggtctt    31620
tatttataaa gaaatagtat tgagccaccc agttggggga tacacagtct aagtagttat    31680
tctcttattt tgtttctggt tcccactttt attgacttat atagcacaca tacagtagtg    31740
gcataatacc agctggattt cagagtgcag aatgaaacca tgtggttttc tgtgagattt    31800
tttaggcctt atataggaat tatatgcatg actaggacct tataaattat gtatctacta    31860
tgtgcccagc tcctagtata tacctaattt aatccttgaa caactctttt gtgttacatg    31920
gtattatccc tgtttaaaga tgaagaaacc aatatttgga taaattaaat accttatttt    31980
ataaatgagt aagtcttttc tgacttcaga gttcatgcat tttaccagta agccatgctt    32040
tccgcttact gcaaactagt gactccaaac ttctgcaaac tgtgaaacta ttgtgaactt    32100
gtgtgaatgt atggaagttg gcactgatta gacgtttgaa cttctttcct tgtcctgtgt    32160
tatgcatggt aatctgccat ttgctgttcc tagctgtatg gtcacccttta gaggtatgag    32220 ttgtgcttat atgtatatgt tcatgcctag atctgttgct cacagaatca tctgacatcc    32280
ccatttcgtt gaatctaggc agcagggttg atggcagcca gaaaagtgtg ccctggggc    32340 aagaatgtct ttagggaaaa atatgttatt gtctttcaga tagtagttct ccaaacagtt    32400
gctccaacag ttcctatgaa aagattgctt gagcccagga gttcaaggca gcagtgagcc    32460
atggtcatgc cattgcactc cagcctggac aacaaagtga gacccctgtct caagagaaaa    32520 gaaaagaaaa aaatgctagg tggatcttca gtttagttca gttaattaag tattttaatt    32580
attaactatt aattataaca ttaagaatgc caggggagga tagagacccg tgattctgtt    32640 ttgggggggca ctagaaaaca gttcctgaga cactggtgct gccatctacc tctacccaca    32700
tcatatcctt atgtagacat aaaatattaa gagagacttc atgaggaggc atttctcagt    32760
ttcttttgta atgaactcta cttttagttg agaaacatga aagtgtatgg tttggtgttg    32820
gagaacgagt ttacttacta gtttgattta cagtgaatac tgttcttggg atttataaat    32880
ggttttagta ttgagaagta gaggagataa atagttctgg tgtcaaggga agcggagcaa    32940
taaaatgaag ctgaaacatg accattaagc ccaagccaat cagatcatct gtgtgccttta    33000 atagaaggct gatgatcttg gttcaggtct tcacttagtt catgtaataa catggaatca    33060
agagttcaga caagtataaa tgcttctggg tcttgtttcc taactaggct tagtttatag    33120
gccagaaaga ttctgctact atcctgttat tactgggggca gtcattgaaa agagcctttc    33180
tattatagtg gactgaagac ataaaatcac acagtacatc taaaaggttt catcaaagtt    33240 gttcttacg aaagagtatt ttttatatc tttgtataat tgaactttt tttaaaaaaaa    33300 acttttttt ttcagccatg aaattacatt cttttcttagc cttaaagact ttgacattct    33360
cctttgggag gccgaggtgg gcagatcacg aggtcaggag atcgagacca tcctggctaa    33420
cacagtgaaa ccccgtctct actgaaaaat acaaaaaatt agctgggtgt ggtggcgggc    33480
acctgtagtc atagctactt gggaggctga ggcaggagaa tggcatgaac ccgggaggca    33540
gatgttgcac tgagccgaga tcgcgccact gcactccagc ctgggcgaca gagtgagact    33600
ccctctcaaa aaaaaagaa gattttgaca ttctctgttc aagaaacttt tacagtgaga    33660
gtaatttagt gtatctcaga caatgttgga gtgatcgatg gttgggtttc cttgttccaa    33720
ggtagaatat caaatgttca gttgacttgt tgatggatca gttttgaccctc gctttaagga    33780 tatgtctgaa aaactgaaat aatgaggtca acatttttcca ggtttttttt tgtcattcta    33840
tgatcgacta agtctgcttt ggttttcagt tactaatcag tgttccacta atgcctattt    33900
```

```
agaaacttta ttttgaaata attatagatt gacaagaagt tgtaacagag ggcctgtgtt    33960
gtataattga agtttaacag tgatacgctc ctttctttct agaaaggctt tcaatttatg    34020
gaaaaattag caaaggtaaa agatgctcgg cgttggacct ttgaaacttc tttcggaatt    34080
agtattttga atgactccat acaactagaa taatggctga aatttctatg gtgctggtca    34140
ggactgtgac tgtggcccga gcatgagatg attttcctgg aaaccaaaag tactactaga    34200
aggagaagaa tgctgtggag ctctctgggg gttggagctt atgcctctgg agactttgag    34260
ttttctgtgg gtgtaagttt tgcaaatggt cctggtagcc ctgaagctag agttgtcaaa    34320
gtaacaggtg gtagctggga gccagcttgg cagtggatca gctacccaaa tagccaaagt    34380
tgctcaatct acatgaggtc ctgtagacca aactgggggt ggggaggatt agccccatac    34440
aaatagttga tccttttttt tttttttta aacagtcatt tgaaatattt tctgtaaaag    34500
gcctaagctt taggcattta ggatgattgt aaatgcactg ctttgtattc ttttcacat    34560 atatttgatt tattaatata aaattgccat ttttgtacat aaaaatggtc aaatattggc    34620
agtttcatat ggtacaacct actgttttct gctgtcacat tggaaattct caccaacgtg    34680
ggataccatg tttcaaagaa acgttggctt agcctcttca tttatggaag aaatatagca    34740
cttatggtgt tctaagtaga ttaactaact taatcttttt acaagcaaat gaggtaggta    34800
ggtcctagtg ttttcctgct ttttaggatc acagagctag taagtggtgg agctgggctt    34860
acaccctggc tactggtcac agggctgtgc tgtttctcag ctcttgtgtt tggcctcacc    34920
tctccagtca tacttgtgaa agtcctgggt gtctagacag gtgatgggtg agtgacataa    34980
ggtacctctc tttgtcttca tgggagaaat aactggatt ccccaagaat gaattaattc    35040
ttccacaata caagagtctt agaggtttaa caaggatact tctttcaagg tgcccaccaa    35100
ttcctacctt gcattggagg gtgcactgtg tcaaatttgt atttttatct taaataccaa    35160
atactcttag agtccatcca tgggcctgtg gagttgaggg taaatgtaga ggcttatttg    35220
gcctaataat gaaagtatgg atagttattg ccatggagga ggagggtgaa tgttttgtag    35280
agtccattcc aaccttgaaa tcctgattct ctgataaact tccacctctc ctctgttgct    35340
taatctttga tcttgagcct ggaaggagag gaggcaactc agtcaatgaa ggagttttat    35400
ttagtaattg cacattggcc tcttcctgcc ggatcccata ttgacactgg agtaaggcta    35460
gaggctggga gacaaggccc catgggagct ttgtgaaatg gggagggca agggtgtgtc    35520 cctggaccgt ctgtttgtgg ggcagctgtc ctaggtgttg agacacacac cggtctgttc    35580
taagatgttc ctactggatc ctgtcagttc gccctccagc attcctggat ttattgtgca    35640
ccatttatgg ctccacagtc cactagatga aattgtaaag actcaatatg gtggctctcc    35700
agggactttc ccttttcttc tcccttagca tcagagatga cccgtcagcg ttgcaagcag    35760
ttctgtggta gcacatcaag tattctgtca cagcaggaaa ggctggataa acatcaaggg    35820
actgccaaga ccagacttct cattcagtct gagtaggagg aaagaggaca ggttgttgga    35880
gagttggttt aaagatgaat tatgggctgg gtgcggtggc tcacgcctgt aatctcagca    35940
ctttgggagg ccgaggcagg cagatcacga ggtcaggaga gttcgagacc agcctgacca    36000
acatggcgaa accccatctc tactaaaaaa tacaaaaatt agctgggcgt ggtggcacac    36060
gcctgtaatc ccagctactc aggaggctga ggcaggagaa tcgcttgaac ccgggaggcg    36120
gaggttgcag tgagccctga tcacgccatt gcactctagc ctgggcaaca agagtgaaac    36180
tctgtctcaa acaaacaaaa aaaagagtta tgactggtct ttctcatttc atctgctgat    36240
gggtagagga gggaaagggt cagaaatatt tcttttaata ccctctcagt atgaatgaat    36300
```

```
gattttgacc tagtttaggt tttggtctgg tggatgtgag attggaatat aatttgtttg   36360
gcagggtcat ccccaaggat gtctgatgca tctgcgttct tgttcccatg gctagaatgg   36420
aatcaaggga gaagcttcct cattcctatt tcagagggag cagggagagt agtggtgcat   36480
atccccacag ccagaaatag attggtcctc aagtaaattg gtttgataag ttgattatga   36540
atcttcctga aaactgctgt ggccttagga actctggagg gtcctactag tggaccctca   36600
tcattcatct gatgagcact tactatgttc taggcactga ctgtgagaaa tacaaatgag   36660
taaaatataa tcatagcccc caggatagtc tggtgggtga catttacaat acaatgtaag   36720
ctaaggttgt aattaatgtg tttaacaaag tactgtggca gcacagagaa gagagtgact   36780
acgtttggag tccacaggac ttcaccggaa agatgaggca tctgacctgg actttgagag   36840
gatgaaccag aactctgtag gtccagtaga tggaaggttt tcaaagaatg caggcagaca   36900
gagccttggg aacagtcaag gttgaggggg cactcttgtg ggtccacaac ccgagcttct   36960
cgcccctctc atttcgtaat ggctgccaag ctcttccttc actgttgttt ttctttactg   37020
ctctgtggat tcatcctgat gagtcacgac aacctctgct tgcagtgatg ccacgtctcc   37080
cagttaggaa acgaccctgc tcttcactgc ctggttcctt ggtgtggctg cctccagcct   37140
tcagtctccc cttctcagag ctgtgacaag aggttcttac agccttaaaa ataaaaagca   37200
gcttcatatg ttttgccttt gtgttattta ttgcatcatt tgttgagcaa gtttcccagg   37260
actggagccg gaggtcattt gagagatgtc tcctgggatt ccactgaaac tcttttccac   37320
tgatcccaat tggtgaccag gaacaggagt tgcttttggt cctttacatc tctccatgtt   37380
ttccagcttc ctaagatacc ctgtcccctc ctgcattttg gtcagcactt atctttcctt   37440
ctgctttgtg cttctagtgg ttctgggtca cttttctgtca gctcccaaat tccagaggtg   37500
gacctgggtt aggccattgg ctgtatgtct tttagtgtgt attgcttgag aatgctcata   37560
tttatgtagt atattccgta gtgcctgaaa attctaagga ccacagcgat tttgaatgat   37620
tcaaagttag tcacttcagt atgaaacagt gtgaatttaa aggcaaaccc aggattcttt   37680
gaaagcaaaa actttcttta gagcagcggc gtgcttggtg aggcaaatag attgcatttt   37740
gtggtgccag aaatagacag ttccctttt atacgctaca tctttgtcat gtagtcagag   37800
acatgcagat cctttgaagt gaattctggc accacaattt tgtagagaca gtcagtgtag   37860
tacagcatga gaaggggcata cgatgtgtca tttgaataac ttctgttgaa gagcaggcgt   37920
cagcccatgg cagagattgc tgaggggatg gtgcagacga gaggcaggta gtattgggggc   37980 attgtgaaaa catgcgtgaa aggccttttg gaatcctgct ttttggcagt gttgtgcaag   38040
tccctcagaa attttgtcac ttcccttgga aacatgtaca acagggatac gtcacttagg   38100
cagagactac tcaagggctg aaaaatgcta cactcatgaa aagtttcgct gagctggaga   38160
ttggtcacat ctgatgtctg gatggtggcc attgttgtta aaaatagctt agaagttcaa   38220
aacgggggta ggagccttgt gttctttttt cttccctgga aagggaagtg tttttgagct   38280
gtggaacttc gagtaaaacc taacttcttt gtaccttgtt ttgctcatct gtaaatgggg   38340
ataacagtgg tacccacctt atgggatgtt caggattcaa tgaatataaa acatttggca   38400
tgatgcctgg cacgtatagc taccactggt gtagtgttta attatattta ttatttttc   38460 tcattgttac tgttctttc tatttgagat ttctcggagg ttctgtactt gttttaaaag   38520
tataattctt tccatggctt tacttcccgt tagcagtggc ttaattctaa ctgggagaaa   38580
aaacctttga tttgtggtaa ttttcttaat tcccttgtct tacctttggg atggtggagt   38640
```

```
tgggagggca gtgcagagtc agatgtcagt ggggaacaga gattgtgggc agtcccaggc    38700
agaggcaggt gccagctggg actgtctagt gccctctcaa ttatttgatg gtggaatgga    38760
tgattattgc agtttgtcaa taaaaaaaaa caaaccatag cgttagtgtt aggagtagct    38820
gagtgaaagt atatgggaat tctgtgtact atctttgcag gtcttgagta aatctaaaat    38880
tatttcaaaa tgaaaattaa agccccagca acaaagcagg atgtagcacc atgctgacac    38940
tagtaaatgc ttaataaacg tttgttggat gcaagagtga gtgagtgagt taggtttgaa    39000
cccaacctcg acacttatta gctagattac ctttggttaa ttactgcttt tatgaatctc    39060
agatttctta tttatttatt taattatttt tttgagacag agtctcgctc tgtcgccagg    39120
ctgtagtaca gtggcgcgat ctcggctcac tgcaacatcc gactccctgg ttcaagcgat    39180
tctcctgcct cagcctccca gtagctggga ttacaggca tgtgccacca cacccagcta    39240
atttttgtaa ttttagtaga cagggtttt cgccatgttg gccaggctgg tctcaatctc    39300
ctgaactcgt gatcccccca cctcggcccc caacgttct gggattacag gcgtgagcaa    39360
ccacacctgg cccagatttc ttatttataa agtgccatga tgtctacctc acagtgttgg    39420
tatgagcgtt aaatgagatg taaagaacct gatcagagga tccagttata tggtaagtag    39480
tctaaagtgt aggtattatt attgttaaag atattgtggg cactttgttg attgaatatc    39540
cccccccctc cttttttaga gccaaaatcc atttaaaaaa tacatttagg tttcttgcag    39600
ttttttgctg ttatgaacaa cacttccatt aataggatta atagctgtat agctagatct    39660
ctgtgtgtgt acattatgta ttcttaggat acatttctga gagtcacatg ggttcctatt    39720
ttttggctct ttttattccc ttaccagagt gcctcccgat agtttgtaat tttgtaacaa    39780
tttaccatta aagaacagag ttttgatagg cagagatggg agagtaggag agagggagta    39840
gcctgtacac aaaaggattg cctcctttac cccaaaggtt gaggcctctg aatgctggtc    39900
tgagctccta gggatgatgc ccctggagcg tagtaattgc ctaggataca accactcagc    39960
cttgtgccac catggtagga cacccaccat gctgggtgtc ctactgccat ggttggggag    40020
ggctgaatgt tttcaccctg ttgctggggg aggtgggac ttggatgagt gacacccggc    40080
gtggacagct accacctgcc catggtagat gaaaccttac tttcgatggg aatggccctc    40140
ccttcttatg ggagttgtag tctgcatgga gtgcggttga acaaggatga gcaggtaatc    40200
caggtgtact tagaatttgc ttcctctgaa tattagaacg tgaagaggac tttgagggaa    40260
tccagcatgg tggttttgac tcttgaaaa tcaaggaacc ctatttcata tcaagtccga    40320
tgtggaatct cagtgtacta aagagtttat tttttttatt atacattaag ttctgggata    40380
catgtgcaga acgtgcaggt tgttacata ggtatacacg tgccatggtg gtttgctgca    40440
cccatcaacc tgtcatctac attaggtatt tctcctaatg ccatcccacc ctagtcccc    40500 cacccctga ctggccctgg tgtgtgatgt tcccctccct gcatccatgt gttctcattg    40560
ttcaactccc acttatgagt gagaacatgt ggtgtttggt ttttggttcc tgtgttagtt    40620
tgctgagaat gatgatttcc agcttcatcc atgtccctgc aaaagacatg aactcatcct    40680
tttttatggc tgcatagtat tccatggtgt atatgtgcca cattttctat atccagtcta    40740
tcattgatgg gcatttgggt tggatccaag tatttgctat ggtgaacagt gctgcaataa    40800
acatatatgt gcatgtgtct ttatagtaga atgatttata atcatttggg tatatacccca    40860 gtaatgggat tgctgggtca aatggtattt ctagttctag atccttgagg aattgccaca    40920
ctgtcttcca caatggttga actaatttat actcccacca acagcataaa gtgttcctat    40980
ttctcacatc ctttccagca tctgttgttt cctgactttt taatgatcgc cattctgact    41040
```

```
ggcatgagat ggtatctcat cgtggttttg atttgcgttt ctctaatgaa cagtgatgat   41100 gagcttttt  ccctatgtt  tgttggccac ataaatgtct tcttttgaga aatgtctgtt   41160
catttccttt gcccgctgtt tgatggggtt gttttttcct tataaatttg tttaagtttt   41220
ttgtagattc tggatattag ccctttgtca gatggataga ttgcaaaatt tttctcccat   41280
tctgtagatt gcctcttcac tctgatgata gtttcttttg ccgtgcagaa gctctttagt   41340
ttaattagat cccattgtc  aattttggct tttgttgcca ttgcttttgg tgttataatc   41400
atgaagtctt tgcccatgcc tgtgtcctga ttatggtttt aggtcttaac gtttaagtct   41460
ttaatccgtc ttgagttaat ttttgtataa ggtgtaagga aggtgtccag tttcagtttt   41520
ctgcatatgg ctagccagtt tcccaacac  catttattaa atagggaatc ctttccccat   41580
tgcttgttta ggtcagattc gtcaaagatc agatggttgt agatgtgtgg tgttatttct   41640
gaggcctttg ttctgttcca cttgtctata tgtctgtttt ggtaatagta ccatgccgtt   41700
ttggttactg tagccttgta gtatagtttg aagtcaggta gtgtgatgcc tccagctttg   41760
ttctttttgc aagagattaa tcttataagt tcagacttgt aggtatcata acttataaga   41820
atcatccatt tacttacct  aaataaatgg atttacaaga gattaatttt atatgttcag   41880
acttgtaggt atcataactt acaagaatca tccatttact tatggtaaag tcaagagaac   41940
aatgaagctg ctgtagtgag cactgaattt taacttgggt tctgagtggc agtcccagtc   42000
aaatgccagt ttcattaccc aggttccatc tggatttaat tttgtttgca gtatagaaaa   42060
gtctgatttg catggataag taattgcaga taagaatagt ttgctaatac cttgcaattt   42120
caggatactc tttaattaaa ttgatccaga agcctgaaag atgaataggg ggaactttgg   42180
tctccaagga gaatcacact gtttaacaaa tactttcatt ctttattaca aactgcaaga   42240
cagatgataa tgtatggtca ctctttttat tacaatgcag cctgttatga attcatttgc   42300
ttttgcataa ctgactattc ccctgtgata agagcataag ccagcagatg tgcctgagat   42360
ttacctggca tttaactgaa catactgcag gtgtgctata gcagtatact tgcttgaaca   42420
gttttaaggc accagacaag tacaggcctg aattttttaaa aagataattc cagtttcctt   42480
cagaatcagt gacatattta caagatacta atataagctt agaattggca agagcagctt   42540
tattctgagg tctacaggaa gataatgtga acacatttgt catcatcagt gtgctaaaat   42600
ttccaataaa atttgaatct gtgggagttt attataatct ctaaaatcat taatatatta   42660
ccttaaaaat aaaattgaat acttttttg  cagagttttt ttttttgtt  tttttttttt   42720 ttttttgcag agttttatag cactcagaac cttttggttg ctcagaacat agcttgaaaa   42780
tcctgatctt tcacatattg cagcctcagt ccttttataa atgatgagat tcaggtcttg   42840
ggggtgaagt gactttccaa atgtaattcc agaagttact gggaaagcca agaggaagag   42900
ttcttgggtc tctttatgct cctctaagct atttttctct gctgagcagt taggactcct   42960 ggaggggca  ggaagctgtg tgctcaagtg acatcctttc tttagttttg tgtgtgcata   43020
tttgtgtagg cacatgaatg cactcttgta tacctactag gtgcagtgag agctggcttc   43080
agggagaaag ggaaatgcgt gatttttgggg tccccagcct gagcctactt tttctcgcag   43140
tattctttgt tctggaatct ttctcatcac ctttttattgc atgaaacttt aatctattca   43200
ggtcccaact ttcaggcttc tctgctctga caagtactag aggccaatat gatagactag   43260
tctgagttaa aaggtggcag tgaaggaacc agctacccct ccctgttttt gtattatcat   43320
aagcacctca tggcatagaa tgctttcacc ccaagcggct gtttcagggg cactggcagg   43380
```

-continued

```
tttggagggg cattgtgttt tgaatagtca gtgccttttg tgccattaaa ctcccatggt    43440
agagagaccc agccttaaga aataagactg accctccata gggctgctgc tagtctatat    43500
attgtctttg tgaaaattag aaaacagcat cttgtctgag tggggtagcc ctgcaccaga    43560
gagtgtggcc tggctagtaa aaggcagatt ggatttcagc catcactttc ttacctcagt    43620
tgggcattct tggcagtgcc caacctgccc aaccatatgc tgtagtcctg attctacctg    43680
ctatcttcca gccaaataca ggggctttgt attcttttgc attatacaga tgtgttcatt    43740
gtggctgctt aatagacgtt tgagttgatc gatactcatc gttgaccaaa tagagagaat    43800
ggcactttgc aggatgttta tttcctgctg tccccatagc agcagcaacc atcagcaacc    43860
tgttacctta aggattctat agttcattca tttattaatt caacagctac ttcttaaata    43920
cctataatgt aaaaggagac agggtaccaa gctacaaaga gcaccatctt tggagtcaaa    43980
tctgggtttg aagtttgtct tttctgttga ttgtctgtgt aatatttgac aaattattaa    44040
actttctgag cctcatttat tcgttcattt gcccacttat tcaacagata tttattgagc    44100
atttcccttg gctggatgaa gatggaaaaa aaaggaagac agacgcagtt ctttccctca    44160
tctctagtga ggatgtggac acaaaacaaa tacatggatc aacacataac aattctaggc    44220
tgtcataagt gccctgagga aaagaaacaa ggatgtgcta aaatgaatag gacctgggga    44280 gtgggggag gggacacggg agaccgtgcc agagagacag agctctttct taatagggtc    44340
gtcagggtac gcccatcaga ggtgagcaca taagcagacc caaagaatgg tgaggacctg    44400
gcctgcagag agcagtcagg gctgaagagt cagcttggac aaaggtggga agtagttggt    44460
atatttgagg acataaaaat atggacttgg ggcataatgg aagacaaggt tggaaacagt    44520
gatgatgata acagtagcaa gcacttgttt agttcctgct atgtccagac actgtgctga    44580
gtgccttcac atacattaac tcttctaatg ctgaccaaaa tactacgag catgtgttac    44640 gatcattgtt ttacagatga agaaattgag gcacagatgg gataaataac ttacccagga    44700
tttcccagct ggcacgtggt agagctggga ttcaaacaca cgtgttctgg ttccagactg    44760
tgcttatatc tgctatgctg tagtgccagt gaaggctggg tcatgccaga cctcagtttc    44820
gtcatcagta aaatgaaact aatatgtgga ttaaacaaaa tgtgtataga atggcagcca    44880
catcaagtca taagcattca tcaggtggac tgtatatcta gtggtggtgg tggttgtggt    44940
cagcattgta ggaaaataca ggggtgcatt aggaagtaac cctctaggga agggccgtgt    45000
atactgataa tcgttaatgt aaggaggaca ggggtaaggg ccctgaggaa agtgtgtgca    45060
tgaacagtgc tgcgatggct ctgaagtggg tcagtttgtt ccacctgggc agtgtggagc    45120
cacttggggg tgggggagg ggatcctgct gttgagtctg gaaaaatggg caggagtcac    45180
atatactgga gcaggtagga ggagcatttc ctctgcacca tcaggtgagc aaagatctag    45240
tgtgtactca gagttggaaa gtggggtctg gagacaatag cactggccgt aggagagagg    45300
caggaactgg agtgaagata ggttagagcc agcactcact ggggcttgat gccattgcga    45360
agctttcagt ttatgcatca gggaatgtgt ggtcctgggg tccacagctt ggtttaaaga    45420
tctaatttgg gtatcttctc agctttctgt gactctggct gagcagcaga gaggaatttt    45480
gttttggctt ttatttgata tgctatctgt catctaccta aaggagcctg cccacctcct    45540
gggttcatac agaggagagg taccactata gtgggaagct ttatgacccc actcctccag    45600
acaggtggtt ttataggtga ttgcaaataa ctggcacagg cttggagcta gacagatctg    45660
ggctgtataa tctgggcttt aacagcattt gaccttgggt cttgtgtttg ggcctcattt    45720
agttccctgt aaagtaggga tttataccat gtctcattgt tatataaagg tcaaataagt    45780
```

```
gcatgacact atgtgcctga agaacatggt aagtgctcag atgatgttag tcggaattac    45840
tagattgcat ggtgtggaag gcccagttac ccacaggaag tcagtttgaa ccgactaatt    45900
gtcttctccc atattttga ggtcaggaag cctaatcagt tggcaggact cattggagcc     45960
acattgagat ggattttaaa gtcattccca ggctctgtgg acatcaggc catgatgtat     46020 acacagtttt cttcttcttg ttttattttt ccttaaggct ttattttctt aaagcagttt    46080
taggtttaga gcaaaaattt ttttttttga dacagagttt ccctcttgtc tcccaggctg    46140
gtgtgcaatg gtgcaatctt ggctcacttc ctgggttcaa gcgattcctc tgcctcagac    46200
tcctaagtag ctggcattac aggtgtgcgc caccacaccc tgctaacttt ttgtattttt    46260
tttttttttt agtagagatg gtgtttcact gtgttagtca ggctggtctt gaactcttga    46320
cctcaggtga tccgcccgcc tcagcctccc aaagtgctgg gattacaggc atgagccact    46380
gcgcccagcc tagagcaaaa ttaagaggaa ggtacagatc tcacacttgc ataacctccc    46440
tcataaccaa catttcccac cagaatggta catttgttgc acttgatgaa cctcactga    46500 catcattatc acccaaagtc catagtttag attagggtcc actcttggag ttgtgcattc    46560
tatgggtttg gacaaatgta tgatgacatg tacccatcat tgtatcacac agagtatttt    46620
cactgcccta aaaatcctct gtgctttgcc tgttcagccc ctgctgacca tgtgtatttg    46680
ctgtcctggt tttagatcat cattatgggg ttggaaaaat agcatcctat aaaggtgttt    46740
gtggctttaa gtgaatgtca gcagttctac agtcctgtcc agtagatgcc atctttcaat    46800
ttgctgaaga tactgattct gttttttctgt tacttcagaa caaacagagg aattttagaa    46860
gaactaccac ccacttcctc agacttactg agcacctgct taggagccac acatagttct    46920
aaggttgatg catgacatac aaagacaaga ccctacttgg cctcatagca gagcacagct    46980
ggggcagtgg acccttgttg tttgtctctt tgatgccggg ctgggtacct ttgacattta    47040
ggaggtcatg gctaggaata ctaggaatcc tataatgtgc acagcaatag tcctgtggat    47100
agaagaattt ttctatagcc tgcatgactt tcaaatgtct ccccagacat tcttgcaggg    47160
aaaaagcctg ttcataattt tctgaaccta gaacctgtaa ttccatttta tgtaacggac    47220
tttttgcatt gttttgatat acccttaatt ttctaggaat gccactactt tgtaaattga    47280
tacgatatac tatataagat actacactat tttgtttgta actttgccaa aagctgttta    47340
ccatttttat aaatcacttg ccaatgttgg tgtgcatgta tttgtgtcat caagaataat    47400
atgcaagtat ctgactgcat ttatagttat tgcattcaga gttgttctgt tgttgtatta    47460
gactacttca ttatgtcttc tgatgtactc gtgacagagc aattactatt gaatatata     47520 ttcttacaga tatctttaaa ttctttattt atagttagga cattatatta tgttgaaatt    47580
gtatatagtt tatattattt ttgattttca tttcagggta gtaaagggag agcattatga    47640
cataaatgtt ttaaaaagca gcaggagtcg gggtgggagg cgttgggaac cgttggtctg    47700
atgcactgga accatatcag taagacctgg caaagtgcag agaaatctgt gggggaaaga    47760
gtttaagctt cattttgttt taagtcatgg catgtgtggc cttgattcta aactctgtgt    47820
ttgaataaag ttgttttttgg ctggtggttt cgaagtttta gaaatgggga gtgtatgagt    47880
agatgtgaag tggttacagt ggtttagtca cagcaccctg ggcctgagaa tcttagccag    47940
agggactcta atttgtgaca tagtcaccac agcaaccaat ggaaatgtcc ccatgtgatc    48000
tgaaccaaag tggttttgga gtgttaaaaa atgtgtgttt aataagctaa aattatctgt    48060
taactgttcc aagggtgatt tttgtatttt caagcatgca caattctaat taaatggcat    48120
```

```
tgtgtaatca cttgtggtct cagtgtagtt tataatgagt tagaataatg aagggggtagt    48180 gagactggaa gttagagacg cagagagcct ttctgcttaa ggtatcctta aacagatagg    48240
tgttaggacc agcaaatagt gatcccagaa acacaataca atatttaatg aagtgctaat    48300
tatgttgcgt gtcagtcatt gtaggctgca attgatggag ctaggtggtg gaggaggagg    48360
aggttggatt gggatgggcc ttgaagggta gtaagtagaa tgttaatgga aagaacctgc    48420
aattgtttcc tacccctaact ttccaagtta ttattatcca cagagtcaca ttggcttgta    48480
ttccaaattt actttatagt agctaataag tatctttttt atttagtacc taacgtatga    48540
tttccactgt ggttggtcct tgacaacagt taggtgagag cgaattgata ctagagatgc    48600
agaaatgtaa ggcttagaag ctcaagtgtc caggaccaca cagagctcat aagtggcaga    48660
gccaggattt aaactcaggt ttgactgatg tcaaagccac tccttatggt ctttttgata    48720
tttttgctct agagatggtg ttcatgatta gcttgtttac ttaccaacca ttttctattc    48780
agattataaa gcagatctca tttggccgag acttggagat ttaagttttt gatatgtaat    48840
ctatgattga atttaaatga ggtatggtta gaaagttcca gcccagttag taatttagca    48900
ccttaaagca ttcaacaagc atggttaacc aaaaacctaa atcatactaa atgtttgaag    48960
tggtgaacag gagggaatat ttttatattg ttactagtca gctttaaaaa aaaatgtgtt    49020
tataaactga gaagtctagg tacatgacat ttatactcct gatgtttgac tggctttgga    49080
aattcccacg ttgtgacttc ttgtaagctt ggctgaatga actgacaggg gattccagcc    49140
cttactgtat aattaaaggt aaagatacag aatgcatctc tctacctcca actattgtgt    49200
agttagttgt agctaccaat gaaattatca ggtcaatgca aaaaaccct tgtttttatt    49260 tatacagggt acaggatgg tctgattagt tgttctcaag taactaactg gggggtgggg    49320
ggcatttagt agtgttgttg ttgtggtttt tttttttccat aagaacaatc aaatgaggaa    49380
actaatagca ctgtgggctg cttagggaat ttttgtcact gaaagaactg ctgcaagccc    49440
tgtgtctcag gaagggtgat ggaatgtcta aatgtccatc tgtcgggaga agattgaagt    49500
ccctatgccg atctactctg cttgtgcaac tttgtgattt gcagccagtt acttaatctc    49560
tctttactgt tgttgactga agtcatgcta tagctggtat ttcatattac aaggacagag    49620
ttcaagaatt atcttcttgg ttggaaatgg aaaggaggta tatctggagt caagtccaaa    49680
tgggtaagcc atctcactct agaaactcac tgtacaaagg gactaagaag ggaatagaga    49740
agctgccttg tttataaaag gttgatccac tcccaatagt ataatcacaa caatttctaa    49800
gaggttttat ttcaaccact tatttttctta tccctaggtt acacatcagt ttggtgagaa    49860
gagctcagtt tttggttta gatgagctga gtgcttgtct cagttcagcc acttgctagc    49920
tgcatagcct tatgcaaggc acttaaattc tctgaatctc tgtttcttta tctgtaaaat    49980
gatttccagt gacctactat atactctagt aggtcactgg aaatcagtta agttaataga    50040
tgtgaaagtg ctttgtacac ttcaaagggc tgtctaaatg tctgtatgag cctgaaggat    50100
agttgttatg ctttcagtta tcagtagtct aggtggctgt gcagaaaggg agaggcgagg    50160
gagtcatatt tttgacaact aacttggggt cctatgatcg aaagcccaga atcctcact    50220 tagattttt ccctaatgca gcagtcttgt gctggatttt ggagtgtggt agaaacatat    50280
gctacactta ttaaagggt ttggcactct gtaatgtggg attactggca tagaagatga    50340
aatgataaag gaacatctca tcatattcag atgtgtgagt catgcacgct tatgagttac    50400
tctgaaaaat ggaattataa tagaaatggg catgagttca acttacatta ttttccttgg    50460
ctttagcagt tttcaggtta aaagtcactg gatacattta actgtcttaa agcatagcat    50520
```

```
ttataaaaag cttttagaac ttagactgta caaaagcacc tgaattggaa actgtgtctc    50580 ttatttttc tatcagtagg atattaggga cagttttgca ctggacctgt tcctgtgtac    50640
tgccttgata cttaactcag tcagtgaatc agtaagcagg aatatatgga ctcctataac    50700
cctattggcc ttcagggagc ttcatggtca tttattctgc ctgcctgttt tacagtgggg    50760
aaaactgagg gccagaaggg ttccttgaat tatccaaggc ccaaggttag gttctggcag    50820
aggcagggtt agaactcatt cagtccacac catgctgtct ccagtgtata tgtgctggat    50880
gagaaatttt ccactgccag cattaattta atttaattta attttagttt ggtctagtgt    50940
agtctagtct tggattagtt taagacagag tcttgctgtg tcgcccaggc aggagtgcag    51000
tggcatgatc tcgactcttt ccaatctctg cttcctaggc ttaagcaatt ctcgtgtagt    51060
tctcagcctc ccaagtagct gggactacag gtatgtgcca ccacacccag ctaattttta    51120
tgttttatgt agagatgagg tctcgccatg ttgcccaggc tggtcttgaa ttcctgggct    51180
caagtgatcc acctgccttg gcctcccaaa gtgctaggat gacacatgtg ccaccacact    51240
tgtcctgttt attccattta aattacagtt cattttgtgt aagccacttt tccctgtttc    51300
cgtcaatttc agatttggaa atacttttca aggattatcc ttaatactac atctcctctt    51360
tatgcttaaa aattttgttt gattctttaa ccagaaatga tcatagtgat ttttaacttt    51420
caatagggag ctacttttc attaattact tgggtcatat ttgtcacttg attcttagca    51480
cttttttctt ttgatgtcgt ttattattta ttgagaaaca tttgagttct tactctgtgc    51540
caggccctgt gcttagcagg tgctggaggt gagaaggcac taagtgatgg aaggacctca    51600
tccaagaacc cgactctgtc ctgagaggat ctagggtgtc cgtcaggccc caccccattt    51660
gacttaggac cattattgtt tttatagtag ctacttgaaa gactcattag gaaaagtcat    51720
gcttttgttc atttctgttt tcaacctagc taaggagaca tatattacaa gtaaataatg    51780
gcacaaattg gcaaatgatg aaagtccagg ggattattgc ctaggtagaa ttttagaaag    51840
atgatgtgga gaaataggaa cacttttaca ctgttggtga gactaaacta gttcaaccat    51900
tgtggaagac agtgtggcga ttcctcaggg atctagaact agaaatatca tttgacccag    51960
ccatcccatt actgggtata tacccaaagg aatataaatc atgctgctat aaagacacat    52020
gcacacgtat gtttatagcg gcactattca caatagcaaa gacttggaac caacccaaat    52080
gtccatcaat gatagactgg attaagaaac tgtggcacat atacaccatg gaatactatg    52140
caaccataaa aaacgatgag ttcatgtcct ttgtagggac atggatgaag ctggaaaccg    52200
tcactctcag caaactgtcg caaggacaaa aaaccaaaca ccgcatgttc tgactcatag    52260
gtgggaattg aacaatgaga acacttggac acaggaagag caacatcaca caccagggcc    52320
tgttgtgggg tggggaagt ggggagggat agcgttagga gatatactta atgtaaatga    52380
caagttaaca ggtgcagcac accaacatgg cacatatata cctatgtaac aaacctgcac    52440
gttgtgcaca tgtaccctag aacttaaagt ataataataa aaaaaaaggt aaaaggagcc    52500
aggtgaaatt aatatcctat ttcaacatgt aatcaatatg agaattgttt atgagatact    52560
tataaatttt tcttcttcga aaaaaagtt gctgccattc aagatggtct ttaaagaagc    52620
gtagtatttg attactggag aggataaggt aattgatttt tttttcaagtt tcagttattt    52680 gttaatgtaa tctccaacac attatatcaa catgatttca tgtatctaaa ggagaaatat    52740
ttcctagtta agtggaaaat agtgcagcta gcttctggaa gatcttcatt ctaagcagct    52800
ttatagtgaa acatttcatt tagaaatctg gaccatcttt cttcagttta ctgtaatcca    52860
```

```
cattcactga gtagaacttg tattgctcat tggaacccag tttattccag ggccctgggt    52920
cattctttct ggcccaacta acatctggat tgaaatgcca gatgcaagac atacagtgct    52980
gctctggtac ctctagctcc attaaataca aagagggga tcaaactcag ttccttggcc     53040
tgaccaagga cctggtggag catgttttca gcaagggcat ctgatttaaa aggagagaac    53100
tagcttagct gccaggccct tgactaagta gtatctcaga ataaagtaat tgaaaattaa    53160
tgagtatcta cttagggtct ctaaatatat ttaattttct atggagggaa cttttttaaat   53220 tgaaaaatgt atcaacatag agaagactat gtaaacagta tgtgtatagt tagagaaaaa    53280
tacctatgta tccaccattc aggttaagaa agagaacatt actggtatct tagaaatcac    53340
ctggtagtcc cctccactgc acttccctca gaggtaacag tcaccccac tttggtatta     53400 atcatgccct ttctaccagt gtatatgtcc ccagagcaag cataaaccta ggtgtataag    53460
gaaagggcag tgatgccatc tctagatgaa ggctcccagg agaagagctt catggtctct    53520
ggttgaattc attaccctg tgtctgaaca gaaactctgg gtcaagtctg gatccagagt     53580
tgagaggttg cagggaccct tttgggaaag tcagtggaaa agatcatgaa tgagttgtgg    53640
gaaacagggc ttctcatagt tggaggtacc tagaagactg cagtgggccc agctgttggg    53700
agcctgggag gagtggagtc aagaggaatg tgctgctcca ccctggctta tgtccagctc    53760
tcaggaatag gccaaatgga atacttctgc ggggtgaaat agtcttctgc tgattcaggc    53820
agcaggacac agcaggggaa caggaatttc atcagtgcat gattaagaaa aaccaaattc    53880
cattaggaat ttggtccagg ctcacccagg cattctaccc tcaatgcagt ctacggggat    53940 cttgcagtg actgccctca acataagtat ccctcaagtt gccctgctca catggggatt     54000
ggtcatcctc tgaggctggc cacagctttt gtgttgagac cgctctgttc tgtgctcctg    54060
ggagttccct tcacttcctc tttgtttaat ctttatttcc tgtgttggag cctgtctcct    54120
gttattttca gaaggatgca tagcagtttg ttttttgaga tctttgatgt ctaactgtat    54180
cttgattctt ccttcatact tcgttgataa tttggctggt tatagacttc tgggttggaa    54240
gttgtttccc ttcagaattt tgcaggcatt gggtgcctgt ctctttcctt ggtgcagctg    54300
ttaaaaagcc tgagaatatt ctcaattttt gatcttttga atgtagcctg ttttattctc    54360
ttttggaagc tttatagacc cttgtttcca atgttatgaa atttcccagg aatgcccaa     54420 acaggtcttt ttctccattg ttttgatggg cctttccaac ctggcaactg gtagcctttg    54480
gttctgggaa atctttctca aatggttttg ctgatgattt tctcccctcc actttctttg    54540
tcttttcttt aggaattcag acatgtgact gtctggattg cccccttaa ttttcttatc     54600 tcttttctcc tattttcaaa ctgttctttt ctaacctatt tcctaaactt tttttttttt    54660
ttttgagaaa gggtctcact ctgtcaccca ggctggatgg agttcagcgg cagaatctcg    54720
gctcactgca acctctgcct cccggttcaa gcgattctcc cacctcagcc tcctcagtag    54780
ctgggactac agatgcatgc caccacacct ggctaatttt tgtattttta gcagagacag    54840
ggtttcacta tgttggtcag ggtgatcttg aactccagac ctcaagagat cccctgcct    54900 cagcctccca aaatgctggg attatagtca tgagccactg cgcctggcct tttcctaaac    54960
attatcttcc aacctttta gcttttgaaa attaagatat tatttaccta cagcaaagct    55020
tatcaatgct aagtgttcct ttggctgttt tgacaatcat ataggcttgt gcagttacca    55080
ccctaaacaa aatatagaac atttctatca acctagaagt tccgtagggc cctttcccag    55140
ctgtgttttc atttctgtta ttatcttttt aatattcgag agctccttt ttctctgaaa     55200 tgttacttta aaaagaaac attttattct tgattcacaa ataaaaggta ttcttttatc    55260
```

```
tttctgaaga cattaatttt taaagttttc tctctgtgta atgttttctc tgagttgctt    55320
ttttctatct ccatgtctgc attagaggct ttcctcagac atatgtttac cttggctgtt    55380
tgtttatgat taaacttgga ggaaggctga gcatgtgcct cgggcttgtg aactttgaac    55440
gtcactaaga gtgagccatt cattgggggaa ctcccagcct ctgtgtcttt aggtcagtcc    55500
tggtgagatg gtcacattcc tcagaagaca gtattccagt ctctcacctg gagggctagg    55560
gactggctgc cagcatttct ggagctgcag ggaagagggt gaaggctgta gcatcctggc    55620
ccccagcact cagcatgtgt gcagatgccg tctttctgcg tgcccagagg ttcccatgct    55680
tcacctgaca tctctagtta caggacccett tgtcttatcc tttccagaaa ctaaacctct    55740
agatatgtgt ttccttataa taaaatagtc actagccaca tggtagccac ttaaatttaa    55800
attaacattt aataaaatta agaaatcggt ttctcagtta cagtagccat cttttaaatg    55860
cctggtagcc acatgtgact ggctgccgta ctggacacag cacagataca aaacgtttcc    55920
attattgtgg accattttac tggacagtgc tggtctagac ttttgctggg gcagaggagt    55980
ggccaacggg attctttttc tcaaacacct ttctctggcc ctctttcttc accccagtta    56040
ctggtgcttc cttccagttc ctgtgactttt ggagacttct gtggtatacg ttaatttggt    56100
tatcagcttt tgccattgtc agcttgggat tcagtatttg tggattatcg aagtcaattt    56160 ttttttttaca tatccaacta cttttccagtt tccaaagttg tagttttctc ctcttcttt    56220 cccccttacat atttgtgaat ttggtcttaa acagaaaagc catgctgtat ttattatact    56280
actttatata ttttaaaaat atgtactata tttttagtgga gtttcagaag ggagtgaaat    56340
tgggtatttc tgttcaatct gccattttag ctgggaatcc tgcctcattt accttcacaa    56400
tcctataagg tatatatgtg gttattctca tttatagtg aagagaggca ggtaaaataa    56460
ttgactcaag gtcacatagc tagtaagtgg gatttgaagt tggatcagac ttaaaaaatc    56520
agagagcttt ttttattaaa tagtgttgtg cctatcttg tattgaggaa agacccaccc    56580
atcacacgtt ccccaagttg caatactata gttatagttg tgttttaaat accatgtgtt    56640
tggctgggca cagtggctca tgcctgtaat cctagcactt tgggaggcag agatgggtgg    56700
atcacttgag gtcaggagtt caagaccagc ctggccaaca tggtgaaacc ccatctctac    56760
taaaaataca aaaattagcc gggcatggtg gtgcacacct gtaatcccag ctactcagga    56820
gactgaggca ggagaatcac ttgaaccca gaggcagagg ttgcagtgag ctgagatcac    56880
gccactgcgc tccagcctgg gtgacagatg agactctgtc tcaaaaaaac aaaacaaaac    56940
catgtatttg cccagatact tcccagttat ccttacaacc acttaataaa agaggtcagc    57000
cttggatagt tctgtctcag aaaggttctt ttctcctcag ctgttatttt cgttgttttg    57060
ggactttaca acctctaaac tttgtgttag ctttttcttt agcagttctc aaagtgttta    57120
gagtcagaag cattccattg tttaacttaa acctttatt tgaagcatct atggtcattc    57180
tcttatatta aaattgttcc ctcttcattt aacctcactt tccataaggc agcgagtaga    57240
tcgtgtttat ttttgaatcc ctagtgcctg gccccttgtc tgaggtaggg gattcatagt    57300
gtttggttca acatcatctt ttatttggac cattgcagtt gcttccaaac tgctggtctc    57360
tgccttctgt cagctgctct caaaatgacc tgacattggt ctttctcaaa atcaacaatc    57420
actggcctcc tctaacctgc attgtagagt cttggctact cagcatggtc tagagggttg    57480
accacgcctg cctctgtcca ctgctgtagc cccatgtctg gccactcacc ccccaacgca    57540
ccctccagtg caccaatgtg cactttgtga aaggaccact acatgctctc aaacttgtgc    57600
```

```
tcttatttct gccagaaatg tgctatctcc agtcccacct atttctgtta tttaatatct    57660
attttctgc  aaatcccagc cccaggacat tctctgtgaa acctcgtctg atccaccctt    57720
atatggagtt agaagattat ttttgctccc acacacttcc tttcaattcc tccctccctc    57780
cctccctccc tccctcccctt cttttccttcc ttccttcctt ccttccttcc ttccttcctt    57840
ccttccttct ttccttcctt cctcccttcc tccctccctc cctcccaaat ggaatcttgc    57900
catatgtatt attctgcagt ttgatttttc tccttaatac gaagcttatc atgttgtaac    57960
tattgaatga ttagtcagtt ctattagtgt ctggttcata ggaattatta tcattgtatg    58020
accaatttct agcacagagg ctggcacatt gtaggcacac aaaaattatt tattgagtga    58080
aattgagcca tggtgttgag tgagtccatg gcagttcact tgccatttat tgtctttgaa    58140
ttctgctgtc agtagggtgg tcatatgttc cagtatatgc ctattcctat tttcccagca    58200
tagttatgaa tagttcctga tgtttttaata tctcctagtt ggtacagtaa attatatgga    58260
cacccccagcc tgggcaataa ggcgagaccc tgtctctaca aaaaaataga aaaattagcc    58320
aggcgtgatg gtgtgcacgc ctgtagtctc ggctattctg gacgttgagg tgggaggatt    58380
cagcattgag cctgggaggc caagattgca gtgagccaag attgtgccac tgcactccag    58440
cttgggtgac agagtgagac ctgtctcaaa aaaacttata tataatttttt atatgtatat    58500
ggccacccta ccaattaaac agatctaagt ggaagctcat tttaccttat ccagtggaac    58560
agctagagag taataaatat ttggggtatg aggttgcatt tgaaacattg aatccagttt    58620
ctttccagcc agccaatcag caaagcccca aatcacacac tggaaaaaat tacctttgat    58680
gcatcttcaa agcctaaatg tttcatgttc cagaaggact gctgattcct tttagaagta    58740
cttttacaag aagtggttta ccttcagaaa atggaccttt ttttgttgtt ctgccgcttc    58800
ccagcagtat gaccttggca aagttctccc ggaatgtaaa atggggatga gagtagtcct    58860
gctttacagg gttaatgtgg caattgagat cattcatgta gagtgattag cattgttagt    58920
ggcatagtaa gtgcttagca aatatcagct tttattattg gtgttatgat cgtgaccatt    58980
actatctttt gacatagact agtttagaag acgttggtta tggtcttgaa aggagtgact    59040
aggatctgcc ccacagcttt ctgattgcaa tgtgtatgcc cttaactgcc tgtcaatgca    59100
ggatgctact gcactgtaga ggatggaaaa agaaaatcag taagaagaaa tcatgtgtgg    59160
gttgcaaagg agagagtaga atgacataac tgtggttgct agtgagtcag gggctagctg    59220
tgtctacctt ggaaatcttg ggtgggtcag atttggattg acattagaac agatgggcct    59280
cagaatcacc tggagagttc aaaaaattgt ctactctggg ttccagcctc ggagaccctg    59340
atggatgtag ggtaaggatt ggaattcata tattttttaaa aagctcccag gtaattctga    59400
tacacagctg ggttttgagaa ttactcgatg gagtgaccat ttattaccta ataattctgt    59460
aaagcatttc ctgatcattt gctatttaat gtaaggcaga tgatgacata ggggtcagaa    59520
aacagaggaa gattattgga gagcctgaat taatggaatt aaattttatg agagttttga    59580
atttaagcct gtcatgaatc tgtgttgttg ttgtctagga tccttgccta tatttagatc    59640
atttgaaatg aaataacaga aaattgtgaa atcaggaaca aagtcctgtt agaaatgtaa    59700
aataatcaaa atatgaacct agctatgctt ggatttaaaa ctgaaaggta gatattttct    59760
cctgacattt gaaaatgttt tcaacttttta ttgctcttac tggaaaggag aaagaactta    59820
gctaggtgca tatcatggat acttgactgg gtccaggtca ttacttagat gatttaatgg    59880
aagggcattg ggttaggagt cagtagacct gcgtggagtc tcagctcaga tacttctctt    59940
tgcaaaacct gagttagtta cttcagtcat ctttttggca tgtatttaca tatctgtaaa    60000
```

```
acggagacaa tgttattggc ctctatccgg catgatattg ttgggggtgt aatgaggaca    60060
tgtatgtgat aggaatgtaa agctgtgatg aacacagaga gtgaccatat gtctctgttt    60120
gcctggggca gccccagttt acacctgttg ttgggtataa ttattgatag cacactcttt    60180
aactctcagg tatcccagtt tggctgataa attatatggt caccctgtat tcataacacc    60240
catctattgt ttactattaa tctttcgaag taggaaggtt ttctggcctc attcctgtgg    60300
ccccaaatcc ctcaccaaat aagtatttct tagatgcttt ctggtagttt tcttcaattt    60360
tatgtgaatt tcatctctcc aactacattg gtcagtagat aataattgtt ttttttttc    60420
actcctgaat aattttcttg tttatcatgg tattagcatt ttaaacattc taattgccca    60480
ttttggttgg tgcatcttaa gaaagtaaat ttgaagtgca ggcagaggac agaggaaccc    60540
cagcgggaaa tggctttgtg gaagtacact aaaaatgaag agtacagttt gtttgctgat    60600
gttctgactt ggtgttttgg aatctaaatg ccctatgttg attttttttt tttttttttt    60660
tgagacagag tcttgctttg tcatccaggc tggagtgcag tggcgcaatc tcgactcagt    60720
gcaacctctg cctcccaggt tcaaactatt ctcctgcgtc agtctcctac tgtaatctca    60780
gtagctggga ctacaggcgc tcgccaccat gcctggctaa tttttgtatt ttcagtagag    60840
acaaggtttc gccatgttgg ccaggctggt cacgaactcc tgacctcaag tgatcagccc    60900
gccttagcct cccaaagtgc tgggattcca ggcgtgagcc accacacctg gccatatgtt    60960
gatatttcta agtacagcgt taactcttca aagtaattgg gaagaccaca aaagctctag    61020
atgaaatttc aaatctccct cttccccggg agaaatttaa gaactaccat cagaaaaact    61080
tttcattcct caaataacat tttctttttcc cttttttgac aacgagagca atgcatttga    61140
tcatgtttct cccctgcttt ttttttgacc cctaggaaac tcaaagccaa attcgtagcc    61200
catccttaat gtctatgtgg aaagcagtag actacaaata actttccact agccttgact    61260
ttttgtcccg tattacaatc tccttagtcc tggattttaa aaatacgtat ttctgtttta    61320
ttcaatgtgt tcttataaac tgccttggaa tcttgtgggt taagttaaag attaaataaa    61380
taacgaatat aaagatggta tcatagtttc aacattattt tcatgaaatt gtttgaaatt    61440
tagaaggcac aagcttttgt ggtacagaga cctatactgc ctgagagtca ataaagaata    61500
tactctggtc taccatccca ctgaggaggt cacctcccac cagaacaggg ctaaagagag    61560
caaattacct ccatatgttg cctattaacc tcttggacaa atgattggta acacttagtg    61620
tatgcaggtg ggaataagag caagcgcctg tcttattttt ttgagaccct gtcttatttt    61680
tttgtgtgat ggtctcactg ttgtccaggc tggagtgcag aggtgctgtc acagctcatt    61740
gcagcctcga cctcccaggc tcaggtgatc ctcccacttc agcctcccaa gtagctggga    61800
ctacaggcat gtgccaccac acctggctaa attttttttt tttttttgga gagaggggt    61860
ttcactatgt tgcctaggct ggtcttgaac tcctggcctc aagagatcct cttgcctcat    61920
ccttccaaag tgctgggatt acaagcggga gccactgtgc ctggcctaga agatctgttt    61980
tcttttctct gaataattct tgtgacactg tctctccctc catctctttc tgtttctttg    62040
tcattttttcc cagctatcct ttttttcctt g tcttgtcctc ttctcccctc catcctaaaa    62100
cctttgatca caagctagtt tccttttccac atcatctgct cccctctact aaacgctatt    62160
tcgcccccac ctgctttcag ctgtgcttgc ctctgagccc ctctttcacc acggcccaga    62220
tggggtgcac gtgccagctt ccctgtcagc agctcttgtg agcagcaact gctgctaaca    62280
agcttcccga aaactaggaa aagagataca ccattaaata ccaagcagta atttggagac    62340
```

```
aaaagaaaac atcacatctg attggaatgc cttacgttgc atccagatag tttggtagga    62400
aggagaaata aaaatgtggc ggatagctag cataatgcta gatagcagta gcagtagaat    62460
ctcagttctt ctgtctttt gtaattagct cgttcgttcg ttcattcatt cattcattct    62520
ttcactcagc aaccacttat ctgtgtctgt tatattgcca gtagtgtttt cttgggtctg    62580 ggcttttga tgatagagct ttctgagacc tgggacctgg cctgggaatt tagtattcgc    62640 ttgcttctg ggctggagaa agactgcctc taattataca gtttctccta tgcatagagg    62700
ttatattcat aaatacagtg tacactgaat ctttatttta acaaggggtg tgtgtgtgtg    62760
tgtgtatgtt tgccatgaac atacacacag tatattctaa aaattgtggg catatgcttc    62820
cattttaaca agcttgaaat acagcaattt gaatatctga ttaagattat tcaaatacta    62880
ttttactagt aaaaggaata aaaacctgaa gactaggcaa gatagaagac ttaaccatct    62940
gcttctgctc tggggttttt gggaccttct cccaaaagca ctaatttaag taaaacataa    63000
ttaatatata tattttcaa tctacgtagt aaaactttta ctaattggaa caaatgagaa    63060
ggaagacttg cctgaacata ttgaaagctg cacagtagaa tatgtaaaaa ggaatggcac    63120
aagtggaaat ggtggctcag tagagagccc catatcatgt tgagatgaat aaggatagag    63180
ctgaatagat gcatcatttt gagagggtca ctgccgtgag agtaagtacc agaaaaacta    63240
gccttataag ccttatatat ggcttaatag aggtttaatg tttaagaatt tgataagaat    63300
tacttgtgat tagtgcatta aagttctaac ctgagcagta ctgacttgac ttctctttat    63360
attaccaata ctatttagag ataaatgggt attcctaaag tgtctgaaat gttctgtctg    63420
ttaaggaggt cagtagtcta ctttgtcact ttttttctt taccagtttc atttttggac    63480
agatggtaca atgctctata cacttgtgag catgtctcaa gttccatatt cgaaaaatat    63540
gatttaaaag tgtttaggct agtgagaata acagagttaa gagtcataat tgtatttcaa    63600
ttaatgaata cagttttggt gtgagctggg tctactttgc tttttagtag tccatattac    63660
ttgatagtaa agagacatgt gcgtttcagt agtatgtgtt ttattacact tggaggtaac    63720
ttctgtgtcc tttcaggggc tccacctata aaattaggga gatcctggca tgtcagggct    63780
gagggtacac tcataacaca tcttgttttt tttaacttta agttcagggg tacatgtgca    63840
ggtttgttat ataggtaaac ttgtgccatg catgtttgtt gtacatatta tttcatcacc    63900
caggtattaa gcctagcacc cattagttat ttttcctgat cctctccctc ctcccaccct    63960
tcaccctcca attggcccca gtgtgtgatg ttccccgctg tgtgtccaaa catatcttat    64020
ttgtatgtct tattgaacct gggctcaggg aggtgaaagg atttattatg gcagagcctt    64080
taacgggtcc agcacttttt ctaaattcta ctttgctgta ggtctgagaa aagcccagaa    64140
gtttattgtg ctagaacaat gttattctct ctttcagaat caaaaccttt cagaacccag    64200
ccttttcatt ttctaatagc tattcctccc taaaggatgc caggaggaat atgtaagtat    64260
atttagatag aacgtatgca tacatctcca tgtcttagaa acacctccac ttccaacccc    64320
atgtactgtt attttcattt cagaactgga attaggctgt ggaagcatct gaattgttcc    64380
cctccctatc atcttttctc tttttacaaa tacagtttta ccaaaacaaa cccagttata    64440
aaggcattac tggaaagttt actgtacttt ggatccataa atattctttt tttttttttt    64500
gtgcttctcc tcactgttaa gagaagtctg ctggacaagg agttttgagt atgtgcattt    64560
agtgggtaga tagtggtaaa aggaaaaaga aaaacatgca ctggcatgaa aggtagtagt    64620
atacactcct ccgttttcc tttaaagctt taagaggtag tgtggaatag cagaaacagt    64680
ccttccctat atttctaaag atctggggttc aagacctggc ttttgccatt tacttgctct    64740
```

```
atgagtcata tcacctctct gtgtcaatat ttatgtattc actcaccact tattgagctt   64800
tgtctgtcat acactgcaga tacaacaaaa ctgtcacagc cctgccttct tgatgcttat   64860
gttaagacaa tgatagtgac tgagaatggc gtagtagcag tgtaggtggc gagaaatcgt   64920
gggatatggg acatattttg aagctaaagc tgatagaatt ggtgatggtt tagatgtggg   64980
atgtgagaga aagatgtgtc aagactgact gctgggggt tttgcttcta caacatggtg   65040
aatactggca tttactgaga gagtgaatgc tggggaggag ggaggaggtg tgtgttgatg   65100
gtgtgggaat tccaggttgc ttttatata gatgatggtt tggatgcctg ttaacttcca   65160
agtagagatg ctgaagaggt agttgggatt tttttttttt tttcttttt gagatggagt   65220 tttgcttttg ttgcccaggc tggagagcaa tggtgtagtc ttggcttact gcagctcccg   65280
cctcccaggt tcaaacaatt ctgctgcctc agcctcccaa gtaactggga ttacaggcat   65340
gcaccaccac gcccagctaa ttttgtattt ttagtagaga tggggtttca ctgtgttggt   65400
caggctgatc ttgaactcct gacctcaagt gatccactca ccttggcctc ccaaggtagt   65460
tggatatttg agatcggagt tctgagatag aaatttggac attgttggca tgcatgtggc   65520
atttgaacca tgcaacaggg tgagatcact tcagtagata gagaaaaagt gaagattgag   65580
gcctgagtcc ttgggccacc gacatttgga gactgagaag tgggggagct ccctctggcc   65640
tctgagaatg agaatgctgg aacctgacct ttttcctca tttaggttgt ttgtagggat   65700
catgtgagat aggtacacat aaacacacat caaaaacaac ttagtgctta attgcatgac   65760
taaatatagg agtaagggag gttacatgga taaatcactt tttcacttga ttttcttct   65820 gaaagtctat tttatgggat tgggtgaggt gcgtgcaaat ttgttatatg gcagaggttc   65880
ccaatgtgta gatgtgtaaa tgtgggattt aagggagtga agacagggag ggtatttggg   65940
aaattttaca gggggcctac tgtacaatat ctgctttcaa tacgattatt tctttcttta   66000
ttagtccaga aatatatata gcagtaggat ccatgagcta ttacctttaa caggattctc   66060
atactaaaaa aatttaacac tgatatttga catatgtaga gctatgtaca tttataaaaa   66120
catgtatgca ttctaaatgt gaatcggata cagttgacgt tgtctgcttt tgtggacaga   66180
tatctgcttg gattcccagg ttttcgtaag ctgtttgaac ttgtttcatc tcagtctgct   66240
ctgccccttc tctgtcaccg tcctcgcact ggagatgagg cagggtttcc tgaactgtgg   66300
gctctgttct gggaagaccc tgtagccagc tcctagagaa gacttgcaga aagatgtggg   66360
atgagaacag gaagatcaag tgggttgaag gggaaaaaac aagaaggccg aggcaaataa   66420
aggcagagga tcatttggga gggagttgag gaaaggggcc tccactgttc cctaggtgac   66480
catattttct ctccctcttt gggttatttt ctttgtgcct acctgttta tcagaattgc   66540 aaggatttt cccaggtgtt tgggttgttg agtagtaggt aaatataact ttttccgggc   66600
attaccttct ggaatatctg cttgaaggta aaattgcaaa aatggctcat tctcccctac   66660
ttttatgaac actgttttag tctaatctta ttatattgaa atcttagatt ttatcccatg   66720
cttgtgttta tccaatttta tagggtgtgt gtgtgtgtat atatgtgtgt ggggaatgtg   66780
aatatatgtg aatgaatgcc ttttctagag aatctggtat attaagtcat ctacccaaga   66840
agaaaagtct tctgagattg atgctgtcag ataaatctat agaatttgag aaatgaaaga   66900
gagcatagag aacatctgat ccggactttt ccaaatgtat attccattaa aaagaagtg   66960 ccttggtctg atgatttttt tgggagttgg agactcactg catttattaa ctatgaaagg   67020
cttaagagct cttgctgtta aaatatattat ttaactatgt ttaaccagtg tttctccaat   67080
```

```
tttttcacta tggaccctca ttttccttct ctctcttttt agaaggatat gtacatagaa    67140
cagttactat cattgcacag aagtacaaga ttccagaaaa cataatttgg gaatgctaat    67200
ttaattctta ccttcaaatt gaatgcgata cttcatttct gttggtttgt gttcccatat    67260
gtagtatgag caggttgaat gaattaatca attactgtgt cactcctgac tgtgacattt    67320
tctggttctg attcgttaaa tcaatattta aaaattatat ctgtttctat attaaagaac    67380
cttgtctttt ttgttcctta ctagaaccat agtgtctaat acagtgcctg acacatagta    67440
gtgtctcagt aaatgttact gaacaaatat atacctgtta gattcagagc actgaactag    67500
ctatgtcttg aggctgcaga gagaatgatc ttgttttttgc tctcaaggaa cttgtagtca    67560
agtcattaac tttcctaaga gcatggaatg tgccatggag aggtcccaaa ttagagcttg    67620
attgtgataa tctataggac aaagatagat tggacattat ttctgaccct gtgtcagatg    67680
tgtggattac aacacagctg ggttatgtta acataacttt catgacaaga agtgtctttc    67740
agtaatagtc actgcagcag ccacatagtc gttttatccc tggcaaagac tttatgatgc    67800
tatcagcact aagagattgg agctagtatt attcccattt tagtagataa aagagctaag    67860
gctcagagat ttagagacat gtctaagttg acatacctcc tgactgaaaa gccagaatta    67920
ggacccaggt atgtgattct aaaccttgtg cacttatcca ctaggcttcc tgtcctctca    67980
ccaatactag tatctttcat tgtctcattt gtattagaag ctcaccttga acaggctcag    68040
agaattacac atttccagtc ttcattgtgt ccctgctctg ctccctctgt ccccatgcca    68100
tgagggctgc tttctttaca gctgatgtgc tagctagggt gagttttgga gcaggtaata    68160
aaaagtttac agactttggg ccagatgcgg tggcttacac ctgtagtccc agcactttgg    68220
gaggccgagg ccggtggatc acctgaggtc aggagttcga ccagcatgg gccaacatgg    68280
tgaaaccccg tctctactaa aaatgcaaaa attaaccagg cgtggtggtg catgcctgta    68340
atcccagcta ctcggaaggc tgaggcagga gaatcgcttg aacctgggag gtggaggttg    68400
cagtgagctg agatcatgcc attgcactcc agcctgggtg acaagagcaa aactctgtct    68460
ctttgtcctt accaaccatg ttggcagcat ccatattcta ggctgcagat aggagaagga    68520
attaagaaaa cggggcaaag accttacagt ggtctccagg gtagaagctg ccacacagta    68580
cttttgcttt tatcctgttg gccaaactta ctcacatggt catatcttgc cgcaaaggaa    68640
gctggcaatt gtagtcacta ttgtgagcat tcttgtgcac agctaaaaat tactgttgaa    68700
gaagaggaag gacaatggca tacaatcagc tgtctcttcc accactgcgt attggggtct    68760
ggtgcccatt cactccccctc ttctgacttt tggctagtag ctaatccttt tccctgtcct    68820
tacctttatc ctttaactcc cttcttccta ttatttaaat gttctcaagt ctcttccatc    68880
ttaacatgcc ataacacaca cacacacaca cacacacaca ctctctctct ctctctctct    68940
ctctctctct ctcacaaatt catgagtaaa ggcaccatgt ccccagtgct catgttatat    69000
actcagatcc ttgtgcaggg catagtacat aggggttttt caacaactct tgttgagag    69060
agcaagtggg tgagtgaagg gttgaaacat ttccctctat cctttatcct cggattgaca    69120
gagagatgct gctgtctgtc ttaacatcta tggcacaaat gacaggactg atgattttac    69180
tccctttagt gctgaggagg ctgtttggga ccatgaagta gttctagaaa tgtatcgtgc    69240
tgagaagagc actaaaggga gtaaaataca catcagttct ggttttgttg cttactagct    69300
acaatgacat ttggcaaatt atgtaatgtc tttgagcctc agtttcctca tttgaggaag    69360
tgaagactcc attgacctca caatgattaa attagaaaac tgtgataaag aatacacccc    69420
tgataatatt attttggctt cttatggtga ttttaagat taaggagtat catcatccct    69480
```

```
attttatttc tctaaaataa tatttaaaaa aacgtaaatg ccctatacaa tagagtatta    69540
tttggtcaca aaaagaatga agcactggtg catgctacag catggatccc ctgaggacat    69600
tgtgtaggtg aaagaagcca gacacacaca ttatatgatt caatttctat gaaatgtcta    69660
gactaggcta atagaccagt ggttgctagg ggatgcgata ggggagaatg gagagtgaca    69720
tggggtttct ttttggggtg gtgaaatgtt ctggaagtag atagtgatga tggttgcact    69780
cttttgagat tacactaaga accactgaat tgtgcaccta aaaataagt taaaattta     69840 aatgtcatta tagggcatta taattataag taagagaata cttttaaaac tgtgtctaag    69900
ttttggttca cagtttgtca atgattcttc tgtaacagaa accaacatct ggttggtttt    69960
ttgagttttt tcacctgctg gctgacctta cttgacatac tgtattagac tttctttatc    70020
tttccaggcc tacgcaactc tcagcacact gggaaatctc agggcatggt gttccattag    70080
aaagaagagt aagcatgtgg gcttcttcgt gggtaccatg atgggagaga atagaaaata    70140
agaagttaaa taattcctcg caattctgtt aggcatataa actacacatt taatattata    70200
aaacagtttt ataaatgcac ttggtctatg gtgtctgcat ggattaggtg agtacttctg    70260
gaaggaggtg gggatagtca gagaaggcat gctggggaag gaaatgttta aacatttgct    70320
tcttacacag acatttattg aatatctggc atgccttagg cattgttatt tggtgttgta    70380
tgtacccaga taacagctgc agtccctgcc ctcagggtgc tcaaagacag cgaagacaga    70440
tgattctaca gacagttagg gagcaggatg taagtgctac tccaaaggta agcacaggac    70500
tctctgaacg cctcacttgg gaaatgggag aagtcaggga aaccttgatg gagatgattc    70560
ctgagctagg aactgaagga tgagtgggga cagcaaaggc ttggaggaca aagtcatgct    70620
ggattacagg aactgcaggt aactcagtac gtttggagtt cagggcacaa atggggatga    70680
gccatgagaa gttgattaca agtagccttg taagccatgt cacctaagag agtaagaaat    70740
aaaagagttt tagagcatga tacttccaga ttagcagtct agaaataaga ctggctgcat    70800
tgtagagact tggaatagaa gcggacgaga atgaaggcag aaactttcag gagattgttg    70860
cagtaatttg ggagataagt gggtagagac aacagagtta gaacagagac aacagagtta    70920
gaacgattag ggcttgctcc ccaagtggat atggtcgcag ttcctaggac tccaagatct    70980
ctgtccactt cgctgtctca cttcatgtca gtctgacccc agcctgcctt ctaagtcttg    71040
ttttcttctc ttcatgaaat gcttaagtct tgtgcttact gtcccagaa ctcgcttggt      71100 gatttaatgt ctgttacctt tgattacacc tttatcttca cctagaatgg agctcatctg    71160 ttcccttta cttcttagat ctctgactta tgaatccttt ggaataattc catgctagaa     71220
tgatctcttt gtcctctgaa gtcatagcac ttaatatctc tatcagtcaa tgacaaataa    71280
ttatgttttg ccttgtcaca tctcttaatt gctttgaatt gctagtcaat cttgagccat    71340
tgcagcaggt agagaggtga attggctctc ctgaattcct actcccagcc ctaatttcct    71400
gtataaccca gggggaatga cttttctccc ctcattagtg tagtaacaca tatttgatgc    71460
agaacactta gaaaatctct aaaagtgtgc aaaatgaagt aactactatc acaaacacct    71520
tggaatactc acaggtaatt attccttgtaa tgtcctcccc atccattttg tcaccgtttc    71580
tttaggatta catgtgtgcg tctatgcatc atagctagga tcatcctata catgctgttt    71640
ttcaatttga ttttttcatt accatattgt aagattcttg tgtcaaaaca taggagaatc    71700
ttcaagtcca aattgaaagt ggagctaaat tgttctcagg gagagttgta cagatgagta    71760 tccctatct gaaatgcttg agaccagaca attttcagat ttcagatttt tgggatttta     71820
```

```
taatattagc actatgctta cccattgagc atcccaaatc tgaaaattca aaatcctcca    71880
atgagcattt ccttcaagaa atgtggtagt caaaaagtca tattttggag catttcagac    71940
ttcagatttt ttgatttggg ttgctcagcc ttaccaaaaa ctgaatagtg actatctctg    72000
ggaggaggga ggggaacttt ggcttttcag tgatatcttt ctataatgtt gaatgtgtgc    72060
atttatgatg agtctaaatg attttagag ttgtcaccca tagtttatag gtgacagtaa    72120
tttatacttc tacctaatcc aggcttatat ttacatttaa aaagaagtat aacaccaact    72180
ttactgacta gatagataaa caattttaat ttactgaaat ttcacctttt caccatgatt    72240
ataggtcctt tttccattag ttgtttccat ttcctttgct gtctaatgac ttagatttga    72300
gtcctaggta ataaatacat gtgatctttc acaagtcact tagtgtttct aagctttagt    72360
ttgcttatga gtagaataag aggaatgata cttcaaatta ttgtgaggat tgagatcaag    72420
tattgaaagt gctttgtaaa ttgtaaaaag tatataatta ttgatttttt attgattttt    72480
atattagtca atggtcatga gcagttaagc caactttgct tttttaaaaa ttcatttgga    72540
gaaagactaa aaaggcagag gtgccttcat taatatttat tttggtgcaa tgtgggatcc    72600
atgagatttg ggtttgtgcc acatttctgc tgctaattat tagctatata tacagctgaa    72660
atgcactgaa caagcacagt tttggccagg cccagaaatg ttcagggagc acctggctgg    72720
acatacatca gagagcttgg tgacctgata aagcattcat gcaagctcct ggagactgtt    72780
taactggatg acagtagaag gaaactattt atgcaaattt tgctaactga agttctccca    72840 caccttgag tccacatttc acaggcttgt gagatggaaa tgggtcaaaa tcaggttcta    72900
ataatctctt tgtcatctgc agtcatgcct gagaaggtct gatatggtct tctgaatcat    72960
caagggaagg tagaatttca tccaacatga cttttgtgca tttgctgtat tcagctccct    73020
ggaaacatag gtgccttaat tttatcagtt atccagaaca ctgaattctg gataatagag    73080
gaacagggct gtgtaaacaa ctctgctgag taatagatgg cctcctggcc tctggtttct    73140
gactctgtat tccctttat ccaaggacaa gatgttacaa aaataattca gagtgactcc    73200
caagggcagc cccgtgaact tgctggtccc tccgactgtg ctagcagagg aggatgagtc    73260
accagcagca gaatgttgac tctcccagtg ctattagtgg atgtcccagc cagacgcgac    73320
aaccaggaag acaagctttg ggaaagttct ttctgactca ttaacatcat gatttacaca    73380
agaaaacctc tagcttctca ttttattta tttttaaag aagtttcctt tttgtatgtg    73440
tgtatagcga ggtggggcaa aggtatggat ccctcaaatg aatattcaaa ttagctctta    73500
cccatagcag tatttgaact gtttgctcag ttaaatttta ttgtcctttc tcaatgtaca    73560
gtgcctatat atccatcaaa gagtagcaga ttcattaaga atctttaaaa agaaggacat    73620
tatttttaca cagttgaatt tcaggtgtcc tatgcccatg cctttcccat catttcctat    73680
gtgtgagaac ccccaccca cgtagcacac cttcacatac tggggacttt ccacttgagg    73740
aattcacatg aatctgggga tctgcattct ccttgggtag tatcccctca gaagaaaatc    73800
cagactcctt agggggcatt tgtagcctgg gcccagtttt cctccttacc tcatctttt    73860 tggttctaca caaacctgtt tagtcttcag tcaagtgcct taccctccgg ctttcctcct    73920
cctcctcctc ctcctcctcc tcctcctcct cctcctcctc ctcctcctcc tcctccctcc    73980
ccctccccct ccccctcccc cctcctcctc cccctcccc cctccccccc tcctcctccc    74040
tcgtcctcct gctcctcttc tttttttttc tcttttctt ttgggatgca gtcttgctct    74100
gttgcccagg ctggagtgca gtggcacagc tcactgcaac ctccaccttc tggtttaagc    74160
gattctcctg cctcagcctc ccaagtagct gggactacag gtgctcacca ccacacctgg    74220
```

```
ctaattttg tatttttagt agggacaggg tttcaccatg ttggccaggc tggtctcaaa    74280
gtcctgacct caagtgatcc acccgcctcg gccttccaaa gggctgagat tgcaggcgtg    74340
agccatcgtg cccaacccca ctttccttct tttgctattt cttcatgttt cccttatttg    74400
gaatgttgtc ctcactcagc tcctgttttc atcctgtttg tatcccacct tcttcgtagt    74460
gatagtagta gtattgcatg cctgctgtga gccagttttc ctactgtgtt tatgtatata    74520
tttttccaag agtttaaaat aagcctgtaa aataattatg attatcctta tttgcaaatg    74580
agaaaacagt catagaaagt taaaaattat tcaaagccag ctactaagtg gcagggctga    74640
ggttttcctg agcctgaaca ttcaaccccca ccatgctggt tttccctgcc gtcctctgga    74700
tccgatcaaa ctcactacac cagccccact cttagacctt ctccagacgt gctcttttcg    74760
cttggtcggg tgtgtcctgt gtttggcaat cagtcatgta ttattacctt gctatgtgct    74820
tgggttgcta attcttcttt ggcgatatat cttttgttgt tttcttttct tcttactgag    74880
ctgtgcatcg caggctttac acaatgcgtt tttgttgatt ttacttaatt aatgatgtcc    74940
tggaacaagt gagttatttc tcctagttat atttagccca attagttatt tacatcctac    75000
cataatattt gcctccacta attgctaagt agtcttgcaa attatccttc agtcttcttt    75060
ttctatgctt ttattcctgg gaaggaaaga caaaagaagc tccgtggctg gagtctgtag    75120
tgtatcccat cccctgcaaa gaaaccaaca gaaaaattaa gtggaatgac caggcattgc    75180
cactaaatag tttgatactt tgaaatggat gccagtttgg ctaaattcaa gtgttgtctg    75240
ttagacaagg gctattcgta aaagaattgt gaatgtaagc atgctctgga ctgtgcttca    75300
aggatgcaaa aaagtgtcat tgagactgcc ttcctatgtg cagagtggga aaaggagcat    75360
ttatcttgag aaagaataac tgcatctgat caccgttttc aattcattga tagggaaata    75420
caattaaaga ttcctaacct atttcaggat acccatctac catctaaatc tccaagactt    75480
ggatagcttc cccgttcccg agtagttccc cattgacagg catgcactga actcttcatt    75540
tacgataacc gttgtttcca tgaaatacac tgaaaatttt gcacagttgc aaggtacaca    75600
gaatggattt tgaattcttt tggttgtacg aagcatccct agatgtgatc atgaagttag    75660
acacctggga ctgtgagaaa ataagtcatg tgtaagaaga gtggtttggc agaattttaa    75720
aaatagacct tccatgcttt gtgggtatag tttctacata ttctagatct ttgtggtacc    75780
attatatggc tgtaggaggt aaccaactga agagctttct ggaggagaa gcttattgtg    75840 aaatgaagac tgtgcatatg cgttgtatgg gtctcagtcc agctgtttgt attgaaacat    75900
cataggctat acattgtgag aaaagagaag taatcttgtg gtaaccaaag aagtttgagg    75960
tgaaatatgt ctcactgttt catattcagc tggggaatgt ctcactgttt tatattcact    76020
ttcttatatt tgctgaaata aaaacaaaaa taaggtaaat ttgattagta gtaaccttgt    76080
tgggtccttt aaaacagtgt ttttcaaact gtagtctgtt aatctttact gggctgtgaa    76140
atctgttttg tgggtcttgt ttagcattta aaaatgtatt aaatataaga aaatgtagaa    76200
tagaaggtag agggaatggc acatagtaag gatcaatatc ttttgtgaa acttgtatgt     76260 catatacaca catgtgtact acaaaatata tttttacgg tggatcatgg tcaaaaaga    76320 ctgcaaagct gttttaagca tggctgtcag cataggttcc taggatatca gacaatgatg    76380
tgtaacccta gctggattct tggctgaatg ctaggggaaa ctgggcaga ctggggagga    76440 gtgagaggtg gcacagtggc tccagaggcg ctgtggtgac ctgccgatcc tgctctgccc    76500
tgatgctgct gccgccttgg tgaagactaa gtgcattact cattatatgg atagggttcg    76560
```

```
ctgagagctc tgccagcagt ttaagattgg agtctttgtt ggcagggcag tttcaaagct    76620
gaacataaaa actggttaca gttttttggt tgagggggcc aagtgtaggg gggccatgta    76680
gagaaagatt tttcttgaga tttcctggtt tttttttgtt tgtttttttga gacgtagtct   76740 tgctctgaca cctaggctag agtgcagcag catgatcttt gctctctgca ccctctgcct    76800
cccgggttca agcgattctc ctgcctcagc ctcctgagta gctgggatta caggcaccca    76860
ccaccacgcc cggctaacct ttttttgtttt ttgttttttg tttttttttag tagagacggg   76920 gtttcaccat attggccagg ctggtttcga actcctgacc tcaagtgatc cgcccacctt    76980
ggcgtcccaa agtgctggga ttacaggcgt gagccattgt gccccgcctc gttttgtttt    77040
gttttctctc ctaacttaca ttttgaggca atagctgagt acctttggtg catagactga    77100
aatggacatt tgccatttgg ggggttgtct agcattggaa cccccttttgt ttctagagtg    77160 gtctcccatt gttgctgtgg aagctgaagg aggtgcagac acataactga gggcaaacta    77220
ggttcaacct cttcgattcc tcctcgtcag gactttgaat ctggagggag tggtgcaaac    77280
atacagaggt ggcttgagat cattcatgga agcagcagag ttgggagtcc agtcctggtg    77340
atggctggtg accggtggag gctgtgcgag cagtggtgtc cttatcaggc tgttcctctg    77400
tccttctgtc tttcccttaa actcatttta cccttaggta agcagagctg gtttctgttg    77460
attgtaccca agaacactga gtggatatag aagcatgtt agatttgtgt ctgccctaaa     77520
tgaacttagt atgtgacagg tgagaagaag taggtgaatg cttggtagac acaaatagta    77580
aaatttagca aggggtggaa ggattcaggg ttgttttcct ttgtattcct ttaaattatg    77640
ggtaccttca agctttgtca gatgacttat cagcaggaga ttctatgtct ttacattgtg    77700
acattttgga aatacatgtt aataaaaaat gagctatgtt aggtgcagta caaaatggtt    77760
tcaaactttt ataagttagg gtttgtttta tttgtttctt ttttcagttt taagcttttt    77820
aaaagccttg cgcatactca cagaaaactg atttcctaat gggtgtgagc attttatttt    77880
agcattaaga gatttaggga aatcttgaat catcatcaca acaaccctgt aaagtagata    77940
cttctattat tctgaggaaa caaactcaac agaggttaag aaactggcct aaggtctcag    78000
acagtgggtg ttagagctgg gatctggacc caggttaggg tgactccaag agcaggcttt    78060
taactgcttc tataaggaac tttggagggc atccaatact ttttcattat gcagggtttg    78120
agctcagaga ggttaagagg cttgctcaac accaggcagg tcctagtgga tctgggctgg    78180
aacatgggcc tctttctgac tggtgggaag aagctctcgc acaagctctg ttcctcttgc    78240
accctcccct cctttccttg ctgtctgcct ttttcctgca agattcttcc tgtctgcata    78300
ctctttcctg cacaattgtg cttgtgattt tccttcttcc tggcctttat ttttattttt    78360
tttaagaaac agctgtacct ttcctctctc tttttcagtc ttctccatttt ctgaaaactg    78420 agagcagatt cctctctcct taatccctc tcagcccaaa gcatggccct tgtgtcctct     78480 gttttttgact cccatggttc tcagtgtctg tctctcagca tgccctcaca gcctcttccc    78540
tggggttccc gtgtatatgt tagtcttgcc agctgtcagt agattgtaag attttttggca   78600 tgctcagatg tatttgtgtt acttctttgg attccctga agtcccacac cttgcccaag     78660
gcagagtggt aaatgaaaag gggagtgagg ctacagctga gaaatgtgtt tgagacctat    78720
ctcacctctc actggccagt tgactgtggg aacgccttag ccgagtcttc ccatctgaag    78780
gggctgtgaa actcgaatgt ggtttagatg tgaaagccct ttttaagcca taaagtgcta    78840
tataaatgca aggttttatt gtgatggcac aagtgcttca gaagtatttt tgggataaat    78900
gattaaaaag cacatattgt gcctgggtga gttggttcat gcctgtaacc ttaacaattt    78960
```

```
gggaggctga gatgggagga ttgcttgagc ccaggagtat gagaccacct tgggcaccat   79020
agtgagaccc ctttcccaaa acaacaaca acaaaaatta actgaatgtg gtagtgtgca   79080
cctgttatcc caccttcttg ggaggctgag gcaggaggtt cacttgaacc caggaggtca   79140
aggctgcagt gagccatgat tgtgccacta tattccagcg tgggtgacag agcgagattc   79200
catccccctc catccccccc aaaaaagcac atactatgaa acaagccat tctcccacc    79260 ccgccatgtt ttgagtgtcc atttgtgcca ccaagtcttt gaccctgggg taaggatatg   79320
gatggcttca ctaaatctta tattcattgc tctttaataa gattatggat gtgttagtgg   79380
taattagttt aaaagaagaa aaagtttttt agaaaaggaa aagtaacaaa gtctcttggt   79440
acaatgtggc ttttagaaag acacttactg actttaagca aagtactgta tttacttta    79500 tcaaaaactg tctctcactg aatgcaggct ccttgggagc agtgcgaagc accgaaccat   79560
tgagctggca ttgattattt aatcatccct agtttattgt aaatgaagca gcacttacgg   79620
ttctggggta ttcctggaat tgctgctata gttagaagtg agttattctg tgtggcagga   79680
gtggcatata gaaaagccat agttctgact tcctgacagg aaaaatagca gattttgtat   79740
ttatatgatg tcgtcctttt ggctggaatc catcagcttt acagtatctt gtgatgcttt   79800
catcagaact gttattccac gtctcagcat agcagtgggg tcccagtagc aatagataca   79860
agtcattttc ggtggctcta tgggtgtgaa gccactggca gtttccctgg cttgttgtgt   79920
aggttaggct gttaggaggc ttcctgttca catgttgcta ggactttcct ctcacactgt   79980
ggcagtggtg ccagggcaga gcattagtag tgggcaggaa cacagggaag gctgggggcca  80040 tgcagtgatt ttttaaatga cagtcctttc agtctacaga aggaagagtg ttggagtaag   80100
atcagtctcc tgggtggttg ttagactatg aaaagtacta aaaaaccaga gaagacagtg   80160
gtgttgctga tggggacagt ttagagcagt tcttccccac tgtggaacga gcagggtcct   80220
tagaatcagt agtcacgtgt ttgactcctg gcactctcgc tgattagcgt aaaacctctc   80280
atgcttttta tgagaattaa gtgcgagtgc ctaactccag gctcaagata ttgaaatgct   80340
tagtagatat tgtttttttt ttccttgact ggaactgtat atttcatcaa gctgtaatca   80400
gtttaacaaa ttatggtcaa aatatgagtg cttactgcat gctaaactct gttgggcatt   80460
ttacatgcat tgactgactt aactcttaat agcccagtga gataaatgct attttttatct  80520 ccccacttac accaagaaca ttgaaggtta gggatattaa ctaacttgcc taagattaca   80580
atagctagtc ggtggagacg ccagaattca aacccaggtt gcaatgactc cagcccgtgc   80640
tcttaactgc tttgctgtgt catctgagct ttatgaaatg gggttttgat ttgtatctag   80700
gcttttgctc agaatcccta tttagacttt gctcttcgaa gcagattcat agcccacttt   80760
agtcctgtgc cataaagact attttatatt gcgtcaatac cttttttgtac acttacacat  80820 ctatagcctc ttgcaaaaag ggcattgtag gtacttgatg aagagttttt gaaagttgtt   80880 tgttttttaaa aagagacaac atcttgccat attgcccagg ctggactcaa actcctgggg  80940
cttaagcagt tctcctgcct caacttctca ctgaaagata tttttaatcc ttgtaccaac   81000
cctctaggca ggatgtttcc tcttaggtta atgggtaggg aaactggctt agatgaaaat   81060
gacttgctca tggtcacact tgctagtata gagttagtgg gaacctacac accttggatt   81120
actgtgcttt ttttcattgc ataatgttgc ttactttgta ccttcatctt tcatttacag   81180
ctgttaccga acatacttct tgatcaccta atttgtgctg aggataaagc actaaataca   81240
agacaaaaaa aaaaaatcct gatcttcctg tagttttcat tgttgtgtta ggtttcctta   81300
```

```
ccaacgttaa gactgctgcc tgctgaaata gttgattaag gcttaagatt tttagtctta   81360
aaatttctta agatattaag aagctgattt cagggcattt tctaaattac atatttttct   81420
ttcagttttt ctgagttcat accttaattc ataaacattt tagttgtatt ttctacttca   81480
gaaatcaaaa ggtttgattc ctttaaggca aacacaaagt aattcattgt aggtgtgatg   81540
gtttctttta tatccatagt attttaattc ttgtcattga gtttcactgt caaccagtct   81600
gttttttaacg gtaaaaatct ggcagtggcc cttggccaaa gtggtctcat tctgatgatc   81660
atatttatga acattaaaat agtctatttt tatttccttg tccactatcc aaaatgtgtg   81720
ttcttccctt gcgcagatac cagtctttca aaagatgccc ttgaaaattt aagagagttc   81780
cagttttttc agatagattt ctggaatttt gcatcttgga aaaatttctg acattttatc   81840
tattgcagtg aggctttgtt ccaacccaca gaattgtgtc ttgtttcttt tatttttcc    81900
cttgttgaga aagtgtcaga tatacttgtc ttttttataa gactgtggta aactgaagca   81960
atttgagtaa cccacaaaat ttccctgatt ttttttttcat gtaaaacagc acctacaaaa   82020
ttgagctaca aaagtaatcc tctgtcacca aaagaaaggt attttctttc aaatccttga   82080
caattttata aataaattcg ggtggaagaa ttcactgcta tcaccaaaaa ccttctgatt   82140
actcttcctg gtccttcctg ttttctaagt gtctttatat tcatttgagt tgggaattga   82200
acccagtgaa tcatgttctt tttaaagggt attttgtgat tgctcctggt gaatcttctt   82260
agcattgatg attttttcctt ttgtatattg cagcaagaaa cttgaattta ttcttggaa    82320
ttatccaaag tgtttattaa tataaactga tcttgctcct tttctacttg ctctaaaaat   82380
aatcagctag atcacattgt ctggtttatt ttagaagaaa tattatttgg atgaagccat   82440
tacacaaatg ctgtagcaca cacacaaaaa aaccgcttgt catcctgaat gaggacagtt   82500
gtcatttcat ataaagtgga tcagcagcct taggtttaaa gtgcttagaa cagtgcctcc   82560
catgtcttct aagtgctatg tgggtgtttt ctatttttat catcagaatg gcaattccct   82620
gagagtagag attttgttgt tattgaatcg gcattcaaaa gcatcacagt taatgcatat   82680
tgtcttgaaa ttctgttgct gttcttgttt tctcgaagag tttaatctct aggctaagca   82740
tcacaaatct ataccatttt actgttgtgt tcaataatac tggaggtcag tttgaagatt   82800
aggtataatg tgattgcaat gtagtattgc ttgcagaaga gacagaatga ttggaaaacc   82860
aaactcccct tgattactgg tttttgtaga attctagttc taaaagaatc ttagtgattt   82920
tagtcagatc cttgaatctt acatgaggct aagagaagtt ccatgactcc taagttgaag   82980
taacacatgg tctgatagtg catattaaaa aacttttttaa gttctggcca ggtgtggtgg   83040
ctcacgcctg taatcccagc actttgggag gctgaggcgg gcggatcacg aggtcaagag   83100
atcgagacca tcctggccaa catggtgaaa ccctgtctct actaaaaata caaaaaatag   83160
ctggacgtag tggcgcatgc ctgtagtccc agctactcgg gaggctgagg catgagaatc   83220
acttgaatct gggaggcaga ggttgcagtg agctgagatc atgccactgc actccagcct   83280
ggcgacagag tgagacttag gctcaaacaa aacaaaacaa aacaacaaca gaaaaacacc   83340
tttgtaagtt ctaaaaaggt ttatatggta gcccttctga atggagcctg ggcctggtgg   83400
aacttacagt tctcttcctg tcctaaaagg ctgagttgtg acccttttccg ggtttgaggc   83460
atgcttttca gtactcccct ctggtcagtt ttcactgatc cttggcagct ggtaacggta   83520
tgctgtgagg aaacctgggg tagacaggct ccagacatgc agttagcaag cactgcctat   83580
ggactggcta gtgctgttgg gtgcccaagt gtaaaaagga gtattgtgag gttttcctgt   83640
tcaagcaacg ggagagacaa gcctagctcc tttctgctat aggacctttt tccccacaca   83700
```

```
tgctgatcct tttgctgaga ctgctatctc cgttttggct tcatgcccca cctccatgga   83760
catccattgc atcttaactc aatgtccctt ccctcctgag ccccagacca gatcacattc   83820
cctctatttt atgttctcta cttttccttc atagcatttt agctctttgt aatgacctct   83880
ttctgtacat cttagtttga ttccattctt cccattgact gtaagctcca cgtaggcagg   83940
gaccgtattg cccttgtcct ttgaattagc ttagtttctg cagagctgtt tgaaaatact   84000
tgttgaaaga gtgaatctct tcaacaagta tagcatctga agtcctgctt atgagcagaa   84060
gcaaggcatt agcatgtagc tagtttctaa gtgctgttct gaggcagggc agggtgttta   84120
ttcacataat taaaacaatt gattatatta attttttaaaa aacttttgtg cagtgatttt   84180
aatcttgtta aaattggcca taccaaaata gccaaatcaa agtcatcaca atcaaattca   84240
tacttgtctc ccctgccggg cttccatca ttacttttac ttaagtctta cccactgcag    84300
aaagccttcc caagccagcc cttgccagtg tcagtcacca gagctaacaa catcctgacg   84360
cactcacact attgattta ggttgctttt gtgtttccat ttgtgctgtc tccaaccttc     84420
tattgtaagg ccctgtgggg atgctggcct cgtggcctca gaggtaaccc atctccctct   84480
cccccttcgc tgctgccctg taatgcctgg gactatgctc ttcctaaaac tggattctga   84540
taaaatgtgt tgagtggcca gacagaaaac tgaggtgata atcactgtta atttgagaac   84600
caattttgaa tcaccaaggt tggtagctta ttatttgcaa aaataattgg attctactgt   84660
taagaatttt gtgagaagca acaaggaaag ctgttaaaat aatacaaagc tctgtgtgtg   84720
tgtgtgtgtg tgtgtgtgtg tgtgtgtgtg tgtagacaag gttggggcgg ggtaattcta   84780
gaaggaatga gaaattaaag tgcgcgtttt tgggtgtctt aaactattgt tcacacaatc   84840
aggagagggg ctgttgatgg aaaaagcaca caatcttcat ttacattgga caggacactc   84900
catatcggga agcaaaaatc cctggcttcc tttcttgatg cggtgaagtt agtatcctct   84960
ttgatgtttg caccctaaga tgtctctctg tcctctcgat gtcctaggcc attttttgt    85020 tttgttttgt ttttttcctt cttcctctca aatgctttt cttgcctgct tatggtttgg    85080
gctgcttcct taatgaaaat gccctcttat tttcagatgc aattacctct gccactgatt   85140
tatttattta tttttgtctt tagcgcttct ctgaagtagc tttggaaagt agagaagaaa   85200
atccagtttg cttcttggag aacactggac agctgaataa atgcaggtat gtagatttgc   85260
atatttttaa aaaaggaaaa tatctggctt taaaaaaatt gatgaaaccg tgttcttgag   85320
gctgtagggc tattggtgct attgccttta atttttgaa attgatgtat ttattcattc    85380
ccaatgttga gtatgctggt taaaaaaaac ctcaaataca aaagtatagg aggtacagag   85440
taaaagttaa acttcccttg taatctctcc tagatgttca ccactattaa gaatttattg   85500
tacgttcttc tagattttaa tatgcatgtg cataatcata ttatacatgt tgtgcatatg   85560
catgatcata ctatccatat tatgcttttt tcattttgca gaatgtcctg tgcatctttc   85620
tgtgttgatt catatgcagc tttatgttat cctttttgac agccacatag tagtcctgcc   85680
tgttttgttt agtgagtcct ctcctactgg acattgtcag ttggattttt tcttatttc    85740 tttttttttt ttgagtcgga ctcttgctct gtcaccaggc tggagtgcag tggtgtgatc   85800
tcggctcgcg gcaacctccg ctttcccagg ttcaagcaat tctcctgtct cagcctcccg   85860
agtaggtggg attacaggcg catgccacca cgcccagcta attttctat ttttagtgga    85920 gacaggggtt tcaccatgtt ggtcaggctg gtctcaatct cgtgacctcg tgatccgccc   85980
gccttggcct cccaaagtgc tgggattaca ggcatgagcc accacaccca gccgattttt   86040
```

```
tcatatttca aacaatgtga catcctgtaa atatataatt acatgcattt gcctgtttat    86100
ttccttagag ttagagggtg caacactgtc tttggattct tcccctgtca cgtctataaa    86160
gactctcaag gacaaaggtt tatcttacat tatgaagcag gcttttagct actctgtttt    86220
ccatcacagt ttttcaatgt gggatggggt taggggttca gtgctgggtt ttcaagtggt    86280
cttgcttgtt gatctgaatt tcaaggttaa ttatgaacta actgtttcag gctggtttcc    86340
agaagattct ggtcttcaga tttatttgga aattaaacag ttaaaattga atacctctca    86400
gtttgtagca ttgaggcata tctggttaat gtccctcttt tcagaatctc tcctcaccag    86460
gggagctaat agaccaagca aatgaatttg tgaagagaa ctgtgactgc tgtctgccct     86520
gtatgacttt tcttgtttgg gggagcctcc ttgggtcatt ctgcaagcac ccattatgtg    86580
taagcctctg tgcttcttac ggatatagag aaaaatgact cagttcttat ctcaaggaac    86640
tcacagcatg tgcataagat gcttaaattt cctgtggcta gtgcagtggg ataagtttag    86700
gagcaagaag cgagggcctt agggaatggg atggaggttc agatggct tcctgcagga     86760
ggcgatatct gagctgaatt ctaaagaaag ttgaagtttg ccatgcaagg gataaggtag    86820
aaagatattc ctatagagga atcagtgtga gtgaaggcag gagggtgaga agtagcattg    86880
ggtaggggag gatacagtaa cactgacagc cttgtgggtt tcaagcatga agcaagagc    86940
tcagagtgat agaagataag gtgaggaagg ctggccggcc agatgatgga gcagggctct    87000
gtttcagagt ctcagaattg ctctgtagat taatgggaag cccttggagg atctggtatg    87060
tgttatggag aaattacttt agggtttaa gtgaaggttg gcttggcaga caggaagaaa     87120
gtagtaggag tgtggggtca gcgaattagt ttgtagccca ttggtattgg gcaagaagaa    87180
gaaagaatgt gtagggcttt ccctcatttc tttcctcctt tctggccttg cccaaggcta    87240
agttgctgag gttggttctt tggccctagg tgctctccct ttggagggtg cttatgtgaa    87300
ttacttactt acgcactttt caccagggtt ttctaactgt tccaaagtaa ggcctcctcc    87360
tgccctcctg gtgctgcgtc aaagtcctgc cgctcctcct ggggtggtag gaaccaggct    87420
ccattcatta attgttatgg cccttccatg tgacttatga acatgaattg gtcatcattt    87480
tgtgtgcagt gtctcaggtg gggatgtgaa gagagataag atacggttca tgccctcacc    87540
atgcttgctt tttagtggga gatggacatg aaattaaaat gctgattctt gccataagtc    87600
tgttcaaagc ttatgtgatt ccagtagaaa cagcagcaga atttgtaact aataatcagt    87660
cctttaacat tgttggttcc agaatgggct acattttca attacaactt gggtgcaaat     87720
ggagaaaata aattcaggcc atgtctaaaa ttattctgat ttttgaaaat atggtctgac    87780
catattttca aaatacata attaataaat tacaattcat taattagtat gcataattat     87840
tttccatgtt ttcatctctt atgagatctg acatgtttgg tttccaggaa gggaaggggc    87900
aggggagagg tacgtatcca ataccaacac caaatgtttc tgctttttta ccttcagaac    87960
actccctttt gccataagaa ctttagcac atagagtgac cacatagtct tgtttcctt     88020
ccacaacagt atctaaatat aaaagaggac tgcaatgcca tggctttctg tgctaaaatg    88080
aggagctcca agaagactga ggtgaacctg gaggcccctg agccaggggt ggaagtgatc    88140
ttctatctgt cggacaggga gccctccgg ctggcagtg gagagtacac agcagaggaa      88200
ctgtgcatca gggctgcaca ggcatgccgt gagtactggc agctgccag gctgggggt      88260
ttcaccaaca cactagttca gaagatctgg ggtctctgc ccttgtagc gctgctgggc      88320
agaaagagtt gtggactctg gagtcaggtt cctccctgcc tctgccactg ccacttgcac    88380
gtgaccttag gccagtgatt ctaattctga gggtttcgct tttcactttc ttcatctgca    88440
```

```
gagtggcttc tttctgctcc gtcactaatg aactataaga taccagggga tgacgcttga   88500
cttctgtgga tccaggctca gttctcattt ccccacatct gtacaattgg aataatatca   88560
gcactagatg aggtgctacg taaaacacct gggactaagt ccctgctcag caagtagcgt   88620
atctcaatat cttaataatt attcgaaact tctcctaaaa agtttgaccc ctccttctgc   88680
tgccgtgact gccctcccat gcatggtgct gagttgaagt gagaagctga gtgttgcttt   88740
gtggcttagt caagttccca agttgtgaaa aggacgaggc tctcaacaac acaagctttt   88800
ttttctcctt tcaagtgaga gttgtcttaa agttagcctg ttgccctcag aaggtgggaa   88860
accaaagtcc ctttcatcct ttgaacttga ggacattggc agtttttgct tgcctgattt   88920
taaatgacaa gttaaatcat agaaattaag ttaaatcaca gatctaatcc acttggattg   88980
tgatgatggt tgtacaactg agtaaataca ctagaatctg ttgaattgta cacttaaaaa   89040
ttggtgaatt ttataatatg taaattatat ctcaaagctg ttttaaaaag gttctatcaa   89100
ctcgttttat gatgatgaag tagccattta tgatgccgta cagcctgatc cctactttac   89160
ttatcccacc tttaaccctc agaacaactc tgaggggata ggttggttat tttaagaatt   89220
gcttatcttg ttagtagtac agcttgttta gaaaacctac cttctttctg atatttgtct   89280
ttctgcctaa aatcttcaca caccagagtt tcaggaaaag gggagaggct tatggtatgg   89340
ggaagagcgt gtaggctct tactgactaa acctgacaca gaataaaatg gctgaggtg   89400 tatagattat tagtgggaaa aatccagtaa tattgtcaag ttattttgac taggccgcaa   89460
tgtgtacaaa taaccatctt tagacagcag ctttaagtgt gtttgtaatt atcagaacac   89520
ctagatgtaa atcagtggtt ctaaagtttt ttttaaggct ttgttttttt gttttctccc   89580
tttccccttg agatttggtt tatattgttt attctcttcg ccaagcttct tgccatcagc   89640
acagcaggta taaacctcac tcagtttgta agcaaaggtc attgttgcag agtcattggg   89700
ctgctgttaa tgagggacca aggagctgct gggaaagaga tgagaggaga gagcctgtga   89760
gtctgaggat ggacacagtc gctggacctc ctataactct gggcttaggg tcagccagtt   89820
tggggtgtcg gtttctagcc taccttatag aaaatgagtg gtgtctcttc tgtaactggc   89880
tcaacagaat attgcagaaa ctcatcaatt tcagaaatac atactgaatg ccacaggttc   89940
ttgtagctct cactgttact acagaaagtg atgtttgagg gcagtattgt tttctttcct   90000 gttttttcacc tctgtggggt aaagttttgt ttagttctca ttgattcacc ccctcagtag   90060
ctgtgtcttg gtttgattct cagctctgca ttttactaga tgagtaacct tgaatcatac   90120
taaatctcag gagaccacag attctttgtc tgcaagatgg tcaaaatagt atttacctca   90180
ttagatatta ggaggattaa agggtaatac ttttttttaa atttaaaatt ttaatatttt   90240
ttagagatgg ggtcttgctc tgtcccctag actggagtgc agtggttcca tcatagctca   90300
ctataactgt gacctcctgg gctcaaaagg tcctccagtc ttagcctccc aagtaactat   90360
gactacaggc atgtgccacc atgcctggct cattttttatt atttatggag gtcttgtatat   90420 gttgcccagg ctggtgtcga actcttgacc tcaagtgatc ctcctgcttt agcctcctga   90480
agttttggga ttacaggtgt gagccaccaa actcagccaa aaaattattt atttatttat   90540
ttatttgttt gtttgtttgt ttgagacaga gtctttctct gtcacctagg agtgcagtgg   90600
catgatcttg gctcactact acctccacct cccaggttca agcgattctc ctgccttagc   90660
ctcccgaata gctgggatta caggtgcaca ccaccacgcc tggctgtggg gtttcaccat   90720
gttggccagg ctggtcttga actcctgact tcaagcgatc tgcctgcctg ggcctcccac   90780
```

```
agtgctgaga atattatagg cctgagccac tttgcccggc caagataata aatttagagt   90840
ctgtttgcct gatgcctgac acttagccct cagtaaatgt tagtattatt gttttactac   90900
tcagtacttt tatataaaga gatatgtctt tgatctttct gtttatgggt agtaatactg   90960
ttagaatcag acctgtgtta gaattacaga cagttccatg gttaaaataa gttacacttc   91020
agatatgtaa gtgttggtgc acattcaaat gtggatatgc ataaagaaag gctgggtttc   91080
cagcccagtc cacaaaagcc actttatgaa tgaaaatcta tagcatattt gaattatttg   91140
tcctaataat actgaatcca aaagccattt gcctatgttc ccaggaaaaa cttccctta    91200
cagtttaact ccatattctc ggtttataag aaagactata acttctgaag ggtaactgtt   91260
catattgctt gagaagcatg gattgaggtg ttcaggagag cactagatag ctgccaaggt   91320
atctgtagct tcttaactca gtgtctgcgt tggagagagt ccccgcctgg gtgtgctggg   91380
ccagggaggg ggccctgtca gtgtcagtct cactgcagat gtccgatttg ggaaacaagt   91440
gcctattacc tcatattctc ccaggttttt tgtcatttaa gtttacctca tcttagtttg   91500
aggcctggct gcttatgaaa atatcagtaa tagctgatta ttggcagtca ttctccccccc  91560
aacctgccta tgtttcaggt tcataaaatt ttaatcatgg gcgtagaagt gagtgacttc   91620
ataatctccc tggtctttcc catcattctc ttattgacgg aggcaactgg tggagtggag   91680
aggcagggga gcactgttgg gccagctttg tgaagccata tatcttcttg ctagttggtt   91740
actaaataaa aaatatttgt gataatcata cagagtactt aagaagtata tttattatta   91800
atggtaatag attttaatca ctgacaaaaa tcactttggt tattatttat tctaatatgc   91860
attttgcata ctactgccag gaatttgttt gcatgtctga tgtataatca cgagcgtgtt   91920
agaattgttt aagtgctttc tgtaggaaac agatggaaga tttccccaac tcccagagtg   91980
tttccgatta gcaaagtgca catcaggcag gatctgtgaa cctctcagat agggttttt    92040
ttgaagctgg atttgataag gctctgtgac ggatacctgt aatgagaaat atcatcagag   92100
tttattttt aaatgatcta aatttggttt gccaggagct acagtgcata tttctgggga   92160
gtcatagttc ttgatgatta tgatcaaaac agcctgaccg aacctggtcg gaagtctgtt   92220
tgccctaaga ggatatgagt gacccagatt ctttgtggat gagagagttc cttatctttg   92280
catatattgg gtttagaaac agatggccaa atgtatccgc cttgattttc tgatgtgttt   92340
ttttactttt cctcaggtat ctctcctctt tgtcacaacc tctttgccct gtatgacgag   92400
aacaccaagc tctggtatgc tccaaatcgc accatcaccg ttgatgacaa gatgtccctc   92460
cggctccact accggatgag gtatgggaag tactgacctg gtacctgcct ggctccctct   92520
gcactgaggg acagtggtca gcctggagcc ctgagtcact taccaagaag tattgtagtc   92580
attttttgtaa tttgtaactt ttgtatttgc ttgatgtgag aaaggacttc ttcagtattt   92640
ggaatacaat tcaagatgag tttgatcacc ttcctctgcc acattttaga aagaaatct    92700
tgataaggca gaggatattt tgaatagaat tagtgtccta cagcagagtt tttcaaatgg   92760
gtaatcatag ttatgaattt aatttagtgg attcacagtt atgaattcaa tttaatttag   92820
tgaatttaag aaaaagaaac aggagacgat actatcagca tatatacata acctaagtat   92880
attttttaaa cttttgagat atatatatat atatatatat atatatatat atatatatat   92940
atacacacta tatatataaa ggtcatgata taaaatattt ttcttactaa aagttgcaac   93000
taaaaagctc gagaaacatt gcctgaagtg ttaactagaa attctaggtt ggccttgctc   93060
tctgggagtg gatgttttga ctactccttg aggattttg gctgtggagc tgtaattttt    93120
cttctgatgg gcacctgcct tttctcccat attgcagact ttgagaaatg tcacaggtga   93180
```

```
cacagacagt cagtacttca atagctgcag tctcctgagt ttgtaaacat atttgttcag   93240
taactagaat ggaaaatatg ttagttacat acttgctaag cagaagttaa tgtgtgttta   93300
gcagtggaga ttataaatag ggtggatcct ttttgaaaag caggttaact tacagaggta   93360
ttaaaacagt agataagctc agatgctaat agaatgcagg gatttgctag aaaagccctc   93420
tgaaatctcg gagacttcac agtatcatag ctactatttt tgggagaatt tggtggagtt   93480
gtcaccatta cacaatgact gggatgtttt tctcagtgga cactgaacca gatctaactt   93540
tctttgataa tcatcctagg gctgactttt tcctcttctt tctatgctta accaaagtct   93600
cacctggaga ggaaagctgt gtgccgtgga gatttcaggt cccagctgag ccttctggct   93660
attggctttg ttttccaca tgtaatcttg cttttgtgg cctggggatt ggctgtgtga      93720
tcagcattga aatgggttgt tgcagtttga agtctggaag gggtatgtcc ctgggttcta   93780
attctttccc tctaggtttc tgtactcagc tcagagtcta aatggtagc ttttaggatt    93840 ggaaaagacc aaagttacct aattcaactc tttcattttt ttttcagtgg aaaaactaat   93900
acccagaaaa gggaagagag ttaacccaaa aattacatct agtgaattgt ctgattagct   93960
ttacaattga ggcattgtag agctctttga ggcattagtc ttggttgtct gagtgcctgg   94020
ctattaaagg ctgtctttgc ctgttccctc tttctgttag ctgcctggaa gtgcagggtt   94080
gcttcacttt tagcaccttg actctgtacc tgacatggtg cttcaacagg atattgcttt   94140
gttaccacag gcccttgaa cttggaaaaa aaaaatacca ccctaagcta aacatttgc     94200 ctgatgacaa actacaaaga ttttgaaacc tcataatctc accactaaag gaggcgtaaa   94260
tgaaaataaa tgttggtgat gatttcagtg gagtaccagt tttactttgg gaaatattct   94320
tgtatttcaa ttatcgtttt ctgttttttag ataatgcttt tgatagttgt tgggtaatca   94380
tagttatcct caggtatctc tcctctttgt cacaacctct ttgccccgta tgatgagaac   94440
accaagctct tatatatata tcttagcata agacaaccat attctgtatt cctttttcaaa 94500 aaatatttc ttgcttttt aaacaattga atttcacagt ccattaaaac attttataga    94560
agcctaaaga gagtttgttg tgtataatat ctgcatataa acttaaaata tgcagttatc   94620
tgtacataat tttctcaaaa acttgcagtg cgtagctctg attgatgtct atttgtcttt   94680
tttttctttc tccttcttc ctgctttgtt cctccacgtc atttttgaaaa ggaatatagg   94740 caggtatcat tctacattta ttgatgtcat ttttaatttt ttttccattg gcatgctata   94800
gtatctggaa ttttttgtgta ccaggtttga tgagcacctt tataattaat tttaaaaagg  94860
tgtgtggaat gtctgtcttc agtgtgtctt caagcttggt cttatgggtg ataggagggg   94920
tactgattct ggtagtcatg gatttaaaat tttgttaata ttttttgacat cttattaagg  94980 agaaagctgc cggccttatt ttaggctccc tcatcttctg tttacccttta gcctttgttc   95040 cagtggagaa gctacacatt atgtttggtc tcctcagcct gatgctgtct gagtatctga   95100
cctaaaggct tccaagacaa agatggtccc acagggctct cagcagcctg gaagaatatc   95160
gttgttcaga ccagattgaa gattgtgttc tgcccagagg gagtttgttg ggccctcatc   95220
tctaccagat ccaaggactg tttctcacag agactcagta ggatgtggaa gaagaaggcc   95280
gtggctccgt tggctcaggg aacatctgcc ttttcccctc ctgccacctc ccctggcagt   95340
ggagggtgac ctgtctctct ccttggcacc tcatcagaga ttcttctctc ttggacaaca   95400
ccctccatcc tcggaaccct tttctttcct tatctcggga aaccttccat attgtaccta   95460
cttctcattc tcttattact gccttcctcc gccatcaaac agcatttacc cctcctgttg   95520
```

```
gccattctgt cagaacccct cttttgaacct ctgtagctgg ttcactcctt ccttcctgct    95580
tgtcccaggg agaggatcgt ggctaagttc tcctgggcac gtgttctgtt ctacccttga    95640
agagcagtgc caggcctggg tacagcatga gtggcagcct ccctgccagc tgatagccct    95700
agctttccac tgtcaccagc ggagggtaag ggaacagtcc agcagcttca gaggcctgac    95760
gtggctcatg ctgcccgtgg ctctgcagat gtgtgattct ttctgtgtgt gagagagaca    95820
ccaaagccca cagtcaaatt ctcagtcact ttcgtaaatt acaaggaaga tgggctgtat    95880
agaatcattg aagattataa aaatgttggt ttttaccttt aaagtaactt ctttgtttat    95940
cctttccatg ttaattgcta ctccctgagt ttattcatct tttgtttatc tatcaagcat    96000
gtgttcagta gctgttaggt accaggcact gggattcagt ggtgagcagg acagctgcag    96060
cctttgcttc cgtgcacagc tcacggcatt gctcgaatga tgccacaggc atctgcttct    96120
ctctgccgct tccgtttcta tcttccatgg ggcttccctc ccaggagagc gtgcctcata    96180
tgtgcctggc tttcgttctt tgctctgcct gctttgcatg gtccaggctc tgtagcctgg    96240
catttaatta ttctgttcca gcttcccttc cttggtgctt ttcccctcc tgccacctcc     96300 cctggcaatg gagggcgacc tgtctcctcg gcacctcgcc agagactgtc atatgtccaa    96360
ggacaactta tcctttaagc acagtgccta gagcacacac ttgttagggg cccataaaat    96420
gtctaatttc acttaaaatc agaaaacata gttgagaaat ataacttgta atatttttta    96480
tggaggaagg gaaaagtgtt tagggcctat ggaagtcaca gtgtagtcct gcttgtgata    96540
cgtgccccat tgtgtgttgc tggatagttg ctgctggacc tgaccggttg ctcccagaga    96600
caggaactca cagagtacga gaaacatgcc tgagagccct ccacatctca ggccctaact    96660
cagggcctgg cttgtcttag gctctgcaaa catagcacag tgacagttgt tgaagtgtag    96720
cagcagcttt ttgcagggaa agagggagtt gtatttattg cttctccatg acatggttct    96780
tttctcatta gttcatgggc aagtcaaggg aaagagacct aggtagcagc tgagtctgta    96840
gcctacagat ggcctgggct ggcttggctc agtcacttcc cttagtcact tccacacatt    96900
ccagaaattg tgttttttctt acaggtgaca gaggaagtta tatatggaag gtagggttag    96960
gggcaccaac cccctgtgca attgacaatc catgcataac tttgaccctc caaaacatag    97020
ctaataataa tagcccactg ttgactggaa gccttaccaa taacataaac agactagtaa    97080
cctgtatata tcttatgtat tcatgatgta cctttttctg aaattaaaaa aaaaaattt     97140 ctgtgctaca cagttcgtca gttttttcaa actgttgcaa atctccaaaa aaatttcaa     97200 tatacttatt gaaaaaaaaa tctgtgtatg aatggacttc tgtggttcaa acccatgctg    97260 ttcaagggc aactgtagta gttaagagaa caggcttttg tagttttagg tcacctagcc     97320
tcttggaatc tcagttttcc tcatctgtaa aatgaatgaa accttccttg tagagttgct    97380
gtgaagatta aataacataa tatatataaa gtgcttgtta actcgtttca tgatgcctgt    97440
agtggtgttt gggtagctct cttttaaaat cctattcatc atgtaagata caccatcagt    97500
tgaatagcag caatctggga agtaggaaac actgccacgt aagctgtata tcttgattgc    97560
gtgatgaaac taagttgcag gaatgttaaa atgtcaatca aattggtctt ggattcgagg    97620
tagaatgggc ttagcagtgt ggctgatggt aagcgtgcag ggagctgtgg tcagcatgga    97680
gttccagtca gcaggtgttt ccctattctg gaagcatagt gagaagtcag aggagctgtc    97740
tttgtgatct tcgggaagtc actttagctc cctgagtcat agaggaggtg ctgatgggac    97800
acttctcacg cagcgctagt aagaaggaaa gagatggtga ggggctacaa ggggcagggt    97860
tgtctgcctg cttctcaggg cacttcagcc tccggcactg accactgttg gtgagccagg    97920
```

```
acgccctgcc cacatctggg tcccctttgc cacaattggc attcattttc ctgccttcca   97980
ggttctattt caccaattgg catggaacca acgacaatga gcagtcagtg tggcgtcatt   98040
ctccaaagaa gcagaaaaat ggctacgaga aaaaaaagat tccagatgca accctctcc    98100
ttgatgccag ctcactggag tatctgtttg ctcaggtagg aagtttgggc ccaggagaag   98160
ctggagtttg tgggatggga gaggcattgt agagctcaga cccctgctg cagctgaact    98220
tggtggtgct agagtgcttt aaggcctgtt ctgggtaagt tcttgccaca cctgacttg    98280
ccccaagtga ggagaaaaaa ggcagcattt cagctttcca agaggctggt tatccagctt   98340
gtgggctttg ggcttccttt cttcctat tccttccttt ttccccacct cctaccattt     98400
tattttcat ccgtattaat agccatatgt gcagaggtca gagggaagct ctgcttgtta    98460
gaagatgtaa ttcaacaggg ctgaagaagg cacttctcag cagccgtagt aatgtctggg   98520
gaggaaggag atggccactc tgtcactggt ggtaggatag aaagattaga cgctagaaaa   98580
aaaacaaaag agaaggtaga atcacctgaa attacattta ctctgagatt gctaagattt   98640
ttagtagtat gcttcctgat tttaacatgc aaatttagat actgtataga ttttgaaaat   98700
attttatggt tcattttgtt ttgtaaactg cttttttatt catctgattt tttttattgt    98760
ttgtccttca aatgtcaatt aaaatattga tcttcgttgt tttaatgact ttgtaacaat   98820
tcatttattc aacaaatatt gactggatgt ctgcgtacta tttgcctcag gcacttgtac   98880
ctgctaagat gctggagatg ctggagtgaa caagacagac atggcctctg catgcatcag   98940
atgtacatca agttagaaaa caagcaaata aatgataca tagataatac gtaagaaatt     99000
atggaaagta ctgtgaaagc agaagcttgc aatagagaat atggacaggg gggtttgaat   99060
gggaagacct aatttaaatc atatgatcag agaaggtctc tctaaggagg taacatttat   99120
aatgaatcct gaagaataaa aaggaatctg caattctaag agaggggtgg gggactattt    99180
cttccatgta gagtgtctca gcagcagcac tactgacctt ttggcccaga tgattctttg   99240
ctgtgatggc ctgccctatg cattgtaggg tatttaccag catccctgcc tccacccagt   99300
agatgccagt agcactctct ccttagcagt gatgaccaaa aatgtcttca atattgccga   99360
ctctcctctc agcctcagtt gaaaagatct gatgtagagg gaacagaatg ggggaaggcc   99420
ctgagggcca gtagagctgc aaggagagac catgtggctg cagaccagag gagggtgatg   99480
gggaacgagg ctggagaggc aggtgggggc agattgcata cacagagcct tgtaggagct   99540
ggcaaggggt tatgctttaa ccctgagtgt ggtgggaagc catttggaag gcttcatttt   99600
atgtatgttt caagtcgatg attcttgtta cacgtggaaa gcagattgtg ctgggtccaa   99660
gagtacactc gaaacataca agctgagagt ctgcagcaat gatcctggga gagaaaatgc   99720
tggtttggcc tagtgtagca acagtggcag tggagcaaaa tgagtagatc tgctgttcat   99780
cttgaagata gaattgatag gatttgctgt tgagttggat gtggaagctg agagaatttg   99840
aggaatcaaa gatgatgact gggtttctgt tttgggtgat gtcggatgga taatggagtc   99900
attccccaca cagggaaggt cttgggggaa gagggtgggg aaggggcaga aatcaggagt   99960
cctttttcgg agatgcctgt gaaacataca agtggagatt tcaagtagga aattgagtaa  100020
tgaggctgga gtccagagga aaagccgtca tttatttaac ttagtcaccc gttcctggac  100080
attttctgtt tttctcgttt tccctttat gctattactt tatagtctgt tgtgaacaac   100140
tgcatacgta ggtggtcctg tacacgttct gtttattatt accttagagt ataccattat  100200
gtgtgagatc acacacgtat cagtatatct gtgtcagagt tatgtcccac tgtagggctt  100260
```

```
tagttactaa ttgtccatta tctccattcc atctatgcct tagaactgcc atagagacaa    100320
cagagaaagg ggacagtgca cagccccagg cagatactgt gtggaaaaaa agaaaatgaa    100380
ctggccattt ttagatggtc tttttggatt cagcttccca gttttgtgta tccatagctg    100440
agatttattc tttacctttc ccgggagcag aggtgtaaag gaagagtgtg ccatacttga    100500
agaataagca tggcgttaga ttgaccttt ggaggctcag gaataagtga cttgaggtag     100560
ctgtacagtg aatgtttaca aaaaaaccac aggccaacag gacagtttca ggttttcctt    100620
tgctcttcac acattactgg catagatcat tgttcctcag aagttttttgg aatgtcagtg   100680 acctttcctc acctgagaga aacaagatat cccatggtga aaagaagaga acgggagca     100740 gtgggagccc tccatccaaa aaccattaat ctgaagttct tcagggaaag agagcatctc    100800
acatatgcag gaacacttct cccaggcttt gtgcctgccc tgctccaagc tggagaaagg    100860
cttaagagtt cacactttag tgttctatgt actttaagtc atttgatgaa aaccgaatgt    100920
ggctgtagca cggcattgaa cagtggtcct ggccaggtct agatttaatc ccagcctacc    100980
acttgctaag ccctgggccc ccagggtact caattcttct acttgacttg ggttttata     101040 actgcctgac gttagatact cctagtcatt tattctttc tttctcctta gagtggaatc     101100
tccaggagat caggaacgtg gttagttta ttgctgtttc cctagcacct agaataacat     101160
ctagcccata attagttctc ataattacc aaatgaagga gtgactgaat aggggctgtt     101220
tactgttttg tgccttagat tcctcatctg ttggagatga cgatgttaac atccacgttg    101280
taaggtgtta tgaggactaa ataaaggagc caagcactgt gtggcagcac tgaggcaggg    101340
tttaatcagt gggagccggc actggaatta tcgttttcac tctgtacaaa gctgggctgg    101400
gcactgctgg ttagccttgt tttagttttt gtgtttaaag ttcccgttag ttcttagaat    101460
gctgtgcacc tccatcagtg ggggggtata ttttggtgac acatttcact atgggaaact    101520
cgaacggtag atgtgggaaa atgtacatgt ggtgatgatg cactgcggaa cgttcccctt    101580
tccctagagc tacaccagaa tggagggaga gccccatcaa ctctgtacac ccagctccta    101640
gacaaggcca tctaagcatg tttgtggaat tcatgcatga tcagacctca gcccagtgtc    101700
accttccctt gctctggcgc agtccaggcc tagtacacag tgtttgtcag cgtcacttct    101760
atggcgaagg gacttcgtat gtctgtactg ttccccagtg cctggcatag tgctcagtca    101820
atgttttgtt aaatgaatga gcgggggaga acatctcctg agccccttca cacccaactc    101880
tgtttaaaag agctctgatg ctagagaaac tgccaatctg attcgtctcg ttgctgtgct    101940
gcgtttctag gcggccccctc cctgtgtagt agccttcttg tcaagatcaa aaacgggtgg    102000
gctctcatgg tttctcccc ttgctcctag ggacagtatg atttggtgaa atgcctggct    102060
cctattcgag accccaagac cgagcaggat ggacatgata ttgagaacga gtgtctaggg    102120
atggctgtcc tggccatctc acactatgcc atgatgaaga agatgcagtt gccagaactg    102180
cccaaggaca tcaggtaaag cttcccactg gctgaagaat tgattgtgag gatggtggtg    102240
tttctacatg ttcttacaca tttcagctta attactgcca gggtttggct gacctttgct    102300
ctctatgaaa cccagatctt ccttagaatg tttactacat acacgtagcc taattataat    102360
tgtgtcttga ttttggatgt tggctgctaa tctcagaaat ttgtgcttgg gtgaaatttc    102420
tgagctgagg atgccaataa aattagtggc ccccaggcct tctccgtccc ctccttgccc    102480
atggtggaca ctgtcgtcta tcactgcatt ttttccttt gttttggacc catcttaaaa     102540
atccttctca gtcagttct gtaagcagct actaccatcc caagcctgaa ctctgaacac     102600
gttacagtag ttcactacag agctgttaat tctaatgtga gaattgatca actactatta    102660
```

```
aatatctcaa gaaaattgca tttacttaaa aatatcgttt gagatcaagt ctctgtgaag  102720
gaatatttaa gttctgtcca tctatgacat ccaatagttt ttttcacca gtgggctatt   102780
aggatggtca taaatgaaga cagtctcatt ttgaagaagg gatttcgtag ctgcattgtt  102840
tgtgataggc ggcgtgcgtc ttctcattag gttgctgctt gtttctcctt gcgcttgacc  102900
agagtctaga gcagatcaca gcttgctcct cagtgatgca gggattgagt cgatactgct  102960
caactgctgc tttctctttt ttctgtggcc ttcactttgg gtacttcctc tttatttttt  103020
cataagctaa attgaaaaat gacagttctt ctctaattct gttatattac attaatctaa  103080
aagaaaaata acatttgttg aggatgaatc ccaaacttca caattttcta ctgttctgaa  103140
gccactccat gcggcaggga tgacccgggg ccaggtgctg tctcagtcct gggagtaaca  103200
agcagatcag tctccgcatt tggcccccag tggacttgtt ctttgtttca ggggtactca  103260
acgttcttct taacattgac tcccgttcta gcagtatatc agcttgttta gattctgttt  103320
gttgtagata ctcgcccact agcacctgga taggtaacta atctttcagc ttacctgttg  103380
atctttttaaa taatatatct gattcatatt cacatggcaa acactaagtc ttttgtatta  103440
attagcttta gtatgtcttt ctctctctct ctctcactct ctctctctct ctctttttg   103500
tgggggtgct tgggggacg gagttttgct gttgttgccc aggctgaagt acaatggcat   103560
gatcttggct caccgcaact ttggcctccc aggttcaagc gattctcctg cctcagcctc   103620
ctgagtagct gggattacag gcatgtgcca ccatacctgg ctacttttat attttagta   103680
cagatggggt ttctccatgt tggtcaagct ggtctctcac tcccgacctc agatgatccg   103740
cccgcctcgg cctcccaaag tgctgggatt acaggcgtga gccaccgccc ccagcctttc  103800
tttctcatttt ttaaaataaa aaatgtgatc tgtttagaaa agttataaat cagacatgca  103860
aatagaacat acaaagcatt tctcatcaca caaaatgaca attgctccta acaccttgca  103920
gaccattttc taactgatgc tcaatcctag taacagtgtg tagatgtgag tactaatgtg  103980
cacaagaatg gtgaagctag caagcaaaaa tgtagatgcc ctgccttggt gacccagaaa  104040
attgggcaat acttgtagca attcccattt cagtgaaatc tgtggagcat gtgctttgct  104100
tttctttccc agtttctatt cacctgcatc tccttatgat ggtcatcttc agtgctaact  104160
ccatctaacg tcctctggga atagatctcc cttttcccatt tggcaacatg tggattcatg   104220
gacttagatt tgtttctaaa ctattttctc ctaacctgta catgaaaagg agatgtactt   104280
ttctactgtc ttttagctac aagcgatata ttccagaaac attgaataag tccatcagac   104340
agaggaacct tctcaccagg atgcggataa ataatgtttt caaggatttc ctaaggaat    104400
ttaacaacaa gaccatttgt gacagcagcg tgtccacgca tgacctgaag gtgaaatact   104460
tggctacctt ggaaactttg acaaaacatt acggtgctga aatatttgag acttccatgt   104520
tactgatttc atcagaaaat gagatgaatt ggtttcattc gaatgacggt ggaaacgttc   104580
tctactacga agtgatggtg actgggaatc ttggaatcca gtggaggcat aaaccaaatg   104640
taagtggctg ttggcagtcg atcaaagaga acattcccgt gtcacatagc gtatgctgtt  104700
tatccttctg gagtcatctg tctgcatgtc catcactccc ataggctgag tttatttagg   104760
agaccatgta tcattcatat tttatttcat ccctgtagca caaggtctaa ataagtattt  104820
attgagttat gtagagaaat ataacaacat gtataatacg tagtagtata ataataatag   104880
cagatagttc ctgagtgttt accatgtgcc aagtactttt ctaagtattt tataagtatt  104940
aactcattta tttctaaaaa taaaaaaacc tttgagggaa gtattgctat tatctccatt  105000
```

```
ttacggatga atacaaagag gcacagagaa gttaagaaat ttgcccaagg tcataactaa    105060
taagcatttg tgccaagaat tgaacttagg cctctggctc cgtgaaattg actaattgat    105120
tttgctttat gggagcttct ttatgagata tttattggat gaagaaatag agcagagtgg    105180
cttaagagca tgggttttag acccacgtcg acggggttca gatcctagct tcatgactta    105240
tatggcctta ggagagttat ttcaccttta tcagcagcta aaaattactc ctctgttaaa    105300
tggaggtacc tactgtctaa ctcataaggt tgtgaagaaa ctaaacggca tttagcacaa    105360
agcctggcaa tacaataaat gttgaataaa ttattatagc cgttacaatt attattactg    105420
taattaataa tattaaagta aatgtgggtg ggtgcagtgg ctcacacctg taaccccagc    105480
actttgggag gctgaggcag gcagatcact tgagccgagg agtttgagcc tagcctgggc    105540
aacatggtga aaccctatct ttacaaaata taccaaaatt agcaggatgt ggtggcacgt    105600
gcctgtggtc ctagctactt gggaggctga gttgggagga tcgcctgagc ctgggaggtc    105660
aaggctacag tgagccatga ccttgccact gtgctccagc ctgggtgaca gcaagacact    105720
gtctcaaaaa attaaataaa tgaataaaat atgagactca ttttctcctc ctgtttatt     105780 ctcatgctaa aacaataatg cttgatactt actgagggtt ttctgtataa taggtattat    105840
actatgttag ttagcacttg tctaatctca gagaaccctg tgaagatgta agctatttca    105900
tgaataagga aaatgaggct caaagagatg atgtaactag ttaagtaatt ggcagaggca    105960
ggaacttaac ctagatctct ggtctccagg gctcatgcga cacaaaatat tttcacttgt    106020
gcagatatat attattcagt gtgtagatta tttcaagcat gaaattcgtg tcttctctgg    106080
aaaatcccga cttgagtact gttacaaagt caagacgatt ggtgatagga gaaagctcat    106140
gttcagctca gtggtaactg ggaagagtat gttatctgtt tgtgtcagag catgtgtagt    106200
agtctggaag tgaggagacc tgaatgtaga tgcatgtcta gtgagcagtg atttcccttt    106260
ctgagtttcc gtgcacattg cgtattatat agtttagaca gtgtgctcat taaggtctct    106320
tccagatatg aaagcccagg attccctgat acaacccagt tctttggtcc taaccctgca    106380
ggtgccaact cccccaatcc tgcaagtcca gaagagctgg cttttctcttc cttggaccta    106440 ggccctgcat aggtttccca gcagcactga ccttttacca atagaaaatg aagaaagcaa    106500
cttaaccctg tcccttttat gtatcttatc aggttgtttc tgttgaaaag gaaaaaaata    106560
aactgaagcg gaaaaactg gaaaataaac acaagaagga tgaggagaaa aacaagatcc     106620
gggaagagtg gaacaatttt tcttacttcc ctgaaatcac tcacattgta ataaaggagt    106680
ctgtggtcag cattaacaag caggacaaca agaaaatggt aagtttgtcc cagaagctct    106740
taagtctgga tctggtgatg agagggagaa ttgctgagtt ccgttctgca gcacatgatt    106800
ttcagagttc ctgtcctaaa gagaaaacag gattttctta ttgaagccaa aaagttccta    106860
ttaccaaggc attctcagtg tttaaagtt acaccgatac attccagtgc ctttctttgg     106920
tctcagaaat gtgaatctgc cttaggattt gcttccctcc caaatacacc tcagcatcaa    106980
tatttaattc acaaagctag tggatttgaa ggaaaagaaa accagcgaat gtcagtgttt    107040
cctcccaagg gttctggcac ggcctctctg ctgagctgaa gtgcaaagca ggaagcccca    107100
cgttgccctc aggcgagcct cggccacagt ggcagtcatc gatatggtgt caggcacacc    107160
ccagtgactc tcggacagag gaaagggtgt ttaatctcac ttcctctttt tggtatcac     107220 ttgaggacat aatctaaaca agcaggaagt gggaactctg ccaaaataaa cctgtttgtg    107280
tcaggggaag tcacagccaa caacatgcag agagagcggc tggtgagaca gctagcactc    107340
ttaaggtgag tggagccaac accaggaaag gccacattct gccaaaatgt ggcagatact    107400
```

```
gtgtcacaat gataacgctc agtgctgagg aagagcctgg tgatacggtt tagggcagac  107460
agtcactctc ttgtattcag aataacttgt ctttctgata taaccttttg gaaaacagtt  107520
tggtaacctg ttaaaagcct tgaaaatatt tatatatccc tctgttcagg aatctagaga  107580
atgaatctat cttccagaaa caatgtgaga ggcaggttat ggtttatgaa taagaatatt  107640
cattccagta gtaattaaag tgtcaaaatt ctgaaaataa cttaaatata caataatagg  107700
agaataggaa aataaatcac aatttgcctg agaagcagaa tattagaaaa tcaggttgct  107760 gaattttta  atgacctgga aaaaggtca  ggggaaaaag caggatataa aactttacct  107820
atagaatggg accagttttg ttcaaaatat caataggtat gcatgtatat acacatgctc  107880
ttagaaaaat aaatattaac agctacttat ttatggtggc attatgagtg gttttaattt  107940
tcttattctc ccctccttt  tttttaaaca aaaaacttac attaattta  ttagaaaaat  108000 atagtaaaaa caaagtgaag agggagaagt agaagagctc agatggatgt taatggaaag  108060
atgcgaaatg gagggagaaa agaagaagtg ctgttgatgg agcacatcct ggatatcagg  108120
ccccgtgtta tatgctgcat cctggatatt aggccccgtg tcatatgctg catcctggat  108180
attaggcccc gtgtcatatg ctgcatcctg gatattaggc cccgtgtcat atgctgcatc  108240
ctggatttta ggccccgtgt catatgctgc atcctggata ttaggccccc tgtcatatgc  108300
tgcatcctgg atattaggcc ccgtgtcata tgctgcatcc tggatattag ccccgtgtt  108360 atatgctgca tcctgggtat taggccccgt gttatatgct gcatcgtggg tattaggccc  108420
tgtgttatat gctgcatcct gggtattagg cccctgtta  tatgctgcat cctggatatt  108480 aggcccgtg  tcacatgctg catcctggat attaggcccc gtgttatatg ctgtgcctgt  108540
atcttggtct gtcttagtcc ttgtaagaac cttaggggac tgagcatcag ctctacttga  108600
aatgaggaat ctgagactaa tcaagaggca tgggatcttg cacagggtca ctcagtgaga  108660
aagtggcagg cacttgccca gctctgtctg gttcctgcct gtgcattttg cctgtgttgc  108720
tttggcttct aaggcgttat catcccccag agacccgaa  gggagtgagg gagaggctga  108780
catgtccatg atctggctct tcaacgtggt gtatgcctgg tgcacatttt atgagcctgc  108840
cccatcctgt cctgtcctgg ttgacacagt caagtctagc accaacacaa gttggtgcac  108900
ccatcatcta agtcagagct caccctggcc acatgggcca atgactctat gccaagccac  108960
agtgctgtgg agggagcagg aggagggcag gaagaaagaa atacttgatt cctccattag  109020 tttgttttc  tttaccacgc tagcccttac tgtgtgtcag gtacttccta ttctgagcac  109080
ttcacaaata ccacctattt taattttcat gtcaaccta  tgggtgagta tgataagggg  109140
aaactgaggc acgaagaggt taagtaacct gtccaaggtc acagagctgt taggttaaag  109200
catttgaaat tgccaatatt tgaccatttt gacctataaa aatgatgatt ccatatgcat  109260
aaccctacta gcaggtggag aggctgcgat ttgaacccag agcagctggc tctagagcct  109320
gagctgaggg ttgaccactg ctccatgctg ccagtttaga atctcatgcc ctcgttgtcc  109380
cctcccagcc atgggattcc caagcccttt aatcaggcag tgctttgaag aaaccctgat  109440
accagcatgt tgtcaagtca gaccttcatg tatcacttct ctctacatct ccttggcatc  109500
cctcatttct gtttagactc ctgttctcag gaaatgtaag tgcagatgtg gtcttactta  109560
tcatgtggct gggtgagggg ctgcccaggc cagcctgccc cttgttcaga gcatcttgaa  109620
tttgctcttc agggatatcc gcaggtgggt gcctggtcac acccgcaagg cagtgtgctc  109680
agtgtggttt cttttttctg aagtgccatt cctatggtga ccctgccctc tccaggcctc  109740
```

```
cttcctcata gccccaggca tgcttccttc ggcattacag ctgcactagg cccctgacct   109800
ccctcctgcc gagtggcttg tctcccctgc tccttttttcc cttcactgtc ctctcatttc   109860
tgccacctgc ctctcctttc tacagggcta tgaaagagtc attttgccct ttttttgaagc   109920 ctcagatgct ttttaatgtt ttttttgtgag tcaaagctcc aaatcatggc ttttgcatac   109980
cttcccttgc caggaaatgt tcttgattga cctgatagtt cctgtcaaat gggcagtctc   110040
ttcagggatc aatgatcagg acaaaagtac cccaaatcta caacacaggt gtctttcaga   110100
acaccttcct tgatggaaat cccctccctc ctcttctcca caggtgcctt tgcctcttcc   110160
cactctgagt aagacactct gctctctcca actctcagag ctccctaggc ttaatctagc   110220
aaactcttca ctgggcctgg gattattcct agattaaaat ccgggagttt caccttctag   110280
agcaagtctg ctatgagatg aaccacactg cctctgtttc ttttctccta agcaggaata   110340
atgccgattt agccattcac cgttgagtgc caagatcacg gtgcatgctt tgccccttcc   110400
cacctccact tttgtgcctc tgccaccttg attcaggctt cctcttctcc catctggacc   110460
caggggacag cttctctgca tgtctccctg cctgccacag cctcccccac cgcgtcaccc   110520
ccaacacaca cacacataca cacacacaca cacacacaca cacacgacc   110580 caggggacag cttctctgca tgtctccctg cctgccacag cctcccccac cgcgtcaccc   110640
ccaacacaca cacacacaca cacacacaca cacacacaga gtcatctgat agtttgagat   110700
aatagatggg aaaatgtgtt gaacagtgaa agtcctatat aaatgcaagg gggatcgggc   110760
acagtggctc acggctgtaa tcccagcact ttgggaggcc aaggtgggag atcactcgag   110820
gtcaggagtt caagaccagc ctggccaaca tggtgaaacc ccgtatctac taaaaataca   110880
aaaattagcc aggtgtgatg gcaggtgcct gtaatcccag ctacttggga ggctgaggca   110940
gaagaatcgc ttgacccag gaggcggagg ttgcagtgag ccgagatctc accactgcac   111000
tccagcctgg gcgacagagt gaaactccat ctcaaataaa taaataaata aataaataaa   111060
taaataaata aataaataaa taaatgcatg caagggtat atttagtatt gatgaaaagg   111120
ttttcccttt ggggttccca ttgggttata aaatcttct cactgtgcac ctccctacag   111180
agtcagccac ttaagctgat agagacatga tgtaaccgtg ggaatttctt ctctctcaac   111240
aggaactgaa gctctcttcc cacgaggagg ccttgtcctt tgtgtccctg gtagatggct   111300
acttccggct cacagcagat gcccatcatt acctctgcac cgacgtggcc ccccgttga   111360 tcgtccacaa catacagaat ggctgtcatg gtccaatctg gttggtccta gaaccttatc   111420
agttgccttt ggtgtgcaga gagcccgtgt tttagtgatg gggcatgtca tcattgttta   111480
ggtcaggcca gttgaccatg ctgcctggta cttgttggct gtcctccttt cctccctgct   111540
gtccaagctc tggtcaggcc ttcctgtaat ctcctaccat cctctttgca gcagcccctc   111600
aatgctgctt ctttacttgg atctctcttc atagtttaac cccctcacct ctccatagct   111660
gatcaagaag tactacactt tctgatttct tgctgtgtca acaatgtgg gcaattcaag   111720 aaacactgaa cacagctgag cgtgctgcca tgtgcctgta gtttcagctc cttgagaggc   111780
tgaggtggga ggatcacttg agcccaggag ttcaattcta gcctgggcaa catagcaata   111840
tcccatctct aaaatatata aagaagaaa agaaagatc agatgatgat ctcagcatca   111900
gacagtgtaa taaatggaat tgtcagtcag cttgtcccaa ggtgccaggt gaacagtggg   111960
gaccgtgagg gtaatacagc cttaaggcca gaagggctg tgtgggatgc cttgtcccac   112020
ctgcatctca gaactggcag cctgtgctga agtacctctg gtgatgggca atgtgtgagg   112080
cagcccatgg attggagctc tgactgtgag agatgtgcat acctttctga tatggagctg   112140
```

```
tagttggctt ctctgtaact tctgcctact cacttgaatt ctgccttttg agacaacagg  112200
gattcttttg actttctctt acatatgaca gcccttcagg caaaggaaaa cagccagctg  112260
ctgtgtttct tctgagcctc tcttttcaga ccacagaata tctggggaag catctcttct  112320
gccacctttc acatgatgtg cttctcacct tcttccctct tccggctgcc ttgtggacag  112380
gtagcttagt agtcacatgg ccctggcctt gagaggctca cagactcata gggaaacaga  112440
cacacaaaga atggcagagc aaggggttga gcatttgaaa agcgtcttct gccaatgtcc  112500
cagccatggt tgtgcttcag ggcccaggca ctcgctcttc ccttggccca gaatgccctt  112560
cctccagaat ctgcacagcc tccacttcct tcaggtgcta gtcagatatc accttatccg  112620
tgaagtcttc cttgaccacc ttatatacaa tcatacctct ttcccttctc catcccatac  112680
atgttggcca ctgcactcta ccttattttc cttcagtggc agttgttacc tcctgagata  112740
ctatgtttat ttacataaca taacatttgt tcctggtctg actaccctca cctcccagaa  112800
tatgagcttc ccaaaggctg gggctgcatt gctcactgct ttcttagcac acacagggtc  112860
tgacacattg taggccctca gtgagtattt gttgaatgaa tggatatttc atgtttgatg  112920
ggatgctgac attccttgcc taaagagcct gctcagagta ggtggcattc aaatctgatt  112980
aaaccaaaga atcaatgatg gcttgccagg ccttaaagca cggaaagggt acctagatga  113040
gaggtcagca catgcaaagg catggcgcag ttagaaagta cacaatgtcc ctgtctctct  113100
aaaacacacg aaccatggcg gccctctctc accagcactt agcaagcagc actcacctca  113160
tgcagggatg tattcagtca gtattcactg ctctctacat gccaggactc actggtcctg  113220
gggatacaaa gaaatgtaag acaggcctgt tcctactaac atctgtccag tcctcactga  113280
tgtattctct cagtgtgagc ccatggtgat acaacaataa acaacatggc ctccagttcc  113340
cacccccatg aggtttgtgc ttccactggg ctggctaggg gtggagggga ggcgtggcag  113400
atgctcatca ccagcctcca gagaggctct tctgtcttga gctggagatg atgtctgtag  113460
ggaatgcggg gacaagcagg gctcattgcc ttgggcagga gtctgagtcc tcttctcaac  113520
cttggagact ccatcggtcc tgaggccact cggtatttcc gctacgctca tggatggcat  113580 cagagggac tttaggatcc caggcagggc agatagtgtg atggggctgt taagacttga  113640
ggcagctcag gagagtggat agcccagagg ttcaaagtcc tgtttggtgt gagctctttc  113700 tcccttttgcc tacttctccc tctagtacag aatacgccat caataaattg cggcaagaag  113760
gaagcgagga ggggatgtac gtgctgaggt ggagctgcac cgactttgac aacatcctca  113820
tgaccgtcac ctgctttgag aagtctgagg tcagtcagga cactggcttg gaccaggcca  113880
tacagccatg aggtgtccag tgtagcctgg ttcaggagct gctgcagaca gaaccaccct  113940
tggcagggtg gaactgaaaa gcctgggtct ctgagaagat ccctgggagg tcaggcaagg  114000
gcccctgctc tcaaaaggag actgctcccc agtagccaga ccctgcatc ctcccctgt  114060 agggcccttc ttccttcatg ggacccatgg tggggtcca ccatggctct ggaagacaga  114120
acatgaccag aaaaccaatt cacacccaac acttggaaag tatagtgtca ttatttagag  114180
tggtttattt agactcagtg ccaccatcat ctcagaccca gagctatgcc tgtctacagc  114240
attcactggt acaaaccagc gcccaaatgc cacttcatcc acatggccta acacagtttt  114300
ttccaaatgg tagcttcaga cactttaaca aattgccacc ccatcttaga acaatgaata  114360
gagatgtctt ttagtgattg aagcgtagct gaagctgggg atgatgtgag atacattctg  114420
agggctaaga tattcaccag aattactgac tttgcctcac tagaccacaa atgcctttgt  114480
```

```
tattcatgta attaaaaaaa ctacaaagtg aatattttc aaagacagtg agttttacaa    114540
aacactttac atcagtacac tttaatcagt actggttagg ctccacatgc atggggagac    114600
ctgggacacg gaggggcctt tggcacggag ggtagacgca ggaaggacag cttattggcg    114660
aaccctggg gctggactca gtcaagagtg ggaggaggaa acggcagaag gaaccagcgc    114720
tgccaagtgt cctgggtgat gcaatgcagg aacaccacca cctgcccagg ctcttgctga    114780
acagctgggc ctcggggctc cgtggctcag agcctgtcag gttcattgcc ttcccagaat    114840
gcttgccgtc tattcatcag tcattggagg aagtttaatg tgtttacgat ggaggggtgc    114900
atgagacagc ccagcctcct cctgaagtgg aattggcctg tgcagtacca agagtgtccg    114960
tgactcccta acaatgtcac atcacccggg gaaaacagca gtcatagaaa tgattacttc    115020
caccgcacac tgtggcccac cagaccctgt gccaagcgtt gtacctactt gtgcttttt     115080
aagccttgta atagccatat taggtaggtg atattatccc attgtacaga tgaagtaact    115140
gagattttga atatcatctc ctagtttaca gcttatgtaa gtctttctgg ccctcattgt    115200
ttaccactaa aatagtttag tttgtacaaa aagagcccat gagggaaaac tgcttatacc    115260
tcctatctgg caccacagtg tcccaaacct gggtcagaca ctgaacacca gctcccagtg    115320
tggttttcct caagtggaga catggcctgg aagggctcag tttgaggctg ttccttgaga    115380
agttgtgcca tcataattat tacctcatat ataatatctg ctggacttta taaagggctt    115440
actaagtttt tcaatacacc atgttagata attgtagcaa caatcctatg aggttggatt    115500
ttcatgaact ttatcttaca ggtgaaaaac caagtgacgc ttttgtagaa atagctactg    115560
tgtctgctgt agtattaact cccttttatc aatgccttct cctggacctt gttttattat    115620
ttagttagtt gttggttgga ttatttattg ataataaact ttatttttga ataatttttag   115680
atttacagaa atgttacaga gatggtgcaa aattactctt catgcagctt cccctaatgt    115740
taatatctta catacccatg cctgaccca ttttaaacat gtaatttctg gtcatttccc     115800
gaatagcagg tgcagggtgc ccagaagcag ttcaagaact ttcagatcga ggtgcagaag    115860
ggccgctaca gtctgcacgg ttcggaccgc agcttcccca gcttgggaga cctcatgagc    115920
cacctcaaga agcagatcct gcgcacggat aacatcagct tcatgctaaa acgctgctgc    115980
cagcccaagc cccgaggttc gtctccctgt gccagagcca ggctgtatcc catcagtaat    116040
gtgctgagac ccagatcgac caaaacacgc tgactgactt aaacaaagtg gaccctcccc    116100
acagtttcta ggtgtttttt attgagttta attacacttc tgtgcccaac tcacatccaa    116160
tcccttgagt gtgagcattt tctgtagaag aggcatatac ctttctcagc atctcattag    116220
gctgcagaaa gaggcatgct cagcattagt aagcagaaaa tcacttcttt cttccttaag    116280
ataaaatgcc ttgaggagtc tcctgtcact ggtttattta tctgagagat attcctggca    116340
catcttttgt gggccaagaa ctatatcaga tgcaaagaat cagaaatgca taaggtccag    116400
tccctgctct ctgggggttt cccagcctaa tgctgatgtt acaggtaaat gaggccactg    116460
cagtttgtga tgggtgtttt aactaacata gatatcatac cctggagtca aacagaaagg    116520
gatggtcaaa atccctgagt tccgtggcac agggggctgc ctggaggagg cagctcttga    116580
actgagtgtg ggaggatgag tgggaggttg ccagtgcggt cagggcatct cggcacgtgc    116640
aaacagaggc atgggcgggg gctgccatga aggtgaaggt ggaaggaagg tgaaggtgga    116700
agggagggc aggtgaggct gagcttaggg tgtgggggcc ttgagtgcta tgccatggag     116760
ctgggtcttt atcctgcagg ctgtaggggc caggaggat cagggagtga aatggatcca      116820
aggggagcc actcagctgt ttcttgttaa gcctcttgaa tggcgtcact gatgttctgc     116880
```

```
aggtggattt gtctcttaga atgtgaggac tggaaagaca cgtagaggtc acacagtcaa  116940
ctgtctcatt ttatagatga gaaaattgag gcccagaaga gcgaagtggg tctcatcaaa  117000
ggtcagcgtc aaagaggggc ttgagtgcca ggcctaacct gagtgcccta gctcttgaga  117060
acggtttatt ttgctgctcc tcacctcaag atgctgccct tcatgcgtca ggttcttccc  117120
ttagaaggag gaaggcctca agaaggagc agcacgattg ccactgaggc cccatgagtg  117180
tcagaggaag accctctgag gagtctttat ctgggacaca tcttgttctt ccaagcgaac  117240
gtgtccataa accctcacac caccaggagt gggcagagga agcagcacca ggatagaaag  117300
ggacctgggt tcttgatgtt tgaatcagtt tttggtctca gcaaggggct tgtcactgaa  117360
cttggtgaaa gaggagggac ttgtgttctt gatcagatag gggttcctgc caggctcaga  117420
gaataactgc agcctttgtt ttcatgcttg aggattttcc gcaaaggtaa aaacacatct  117480
gccacttggc tgtgagacct cagagtaagt tcaaaccta aagcccaaca gccctattta  117540
ttcacagcaa cacactggaa cgaacccag ttgaggctcc tgaaactcag tgctgaatgt  117600
gtttcctgtt gcctttccca cctgactgtg aactcttaag acaggacctg agtctcactc  117660
accactctat gggctcgtgg ggaggacagt gcccagcacg gagtcagcgt gaataatgcc  117720
tgtcaagtga acaggtagca ggagctgctg gatggtgggt gcctactgtg gcccaggcag  117780
tttatgtacc tacctcattt atttcatcta cacagtagct ttttgtagat attacaaagg  117840
tgatgaaatt gagacttgag atggtaagtg acttgctcaa ggccatgtag ctagtagtat  117900
cggtagtagg tagaacagta gtaataatta ataagaacgg ctgctatcat gtgagcaggg  117960
cttacagttt gccaggcgtt gtttggagat ctttcatgtt ttaagtcatt tagtcctcaa  118020
aataacccag aatatgttgt tatcccaatt atacatgccc aagatcactt aggtagagga  118080
tgagtgggga tttgaactca cgttgtctga ctccaagtcc agtgattcct tctgtaccac  118140
tgcccccacc ctgcccaggt cacactgtct ttggaaaggt gcagccatca gcctaggact  118200
ttagagcagg caccaattct cctgaccttg ggagagtaag aataaggcct gtgtgtgagg  118260
cctccttaca taggtccccc aaagctctct ctcttccctt tgccatgtgc aaattagaga  118320
agtggggaaa tcgtgaaaat tagacatgag aatattgtgt tgggttcttc agctcctctg  118380
ctctcctaac cacggggttt tgatagccag accctgatct gggtttctca cttgaaaatg  118440
caactaagaa actcttcatg ggataaataa aaagcaaagt gaaaagcag gaggccattc  118500 agagtgggcg tgacggctca gcaggtccca catctctagt cctgtgtcct gtgtccagct  118560
ccactaccca tctcccactc cagaaccctg atgatacagg aagaatgatg acagtgacta  118620
agatgtaatg ccagtcataa tcacggcggc aaccagtcag ggagcgtttt actccatacc  118680
gggcactgaa ggcagccgtt cccttgcgtc atcccattct tccacacggt aacctatgaa  118740
ggacacaact gtggccccca ttttctagt gaggaaacac cttcatggag gcactgtggc  118800
ttcccccatt cacattgtta accctggtgc catgttccct gaagtgccca tgcaaagaat  118860
agtccataaa tggcttcggt tccatccgcc tctcatttcc caagtggctc tgctgcctgg  118920
cctcttgcct gtggacacca gccacggggc cccttcttga tgccttttct cctgagttga  118980
gttgagcctg agttgcctct gaatcggatt ttccccaggt aacagagtgg agtcaggaaa  119040
atggtatgga gggagcagcc tctggaaaaa gagtgcccag gttgtgagaa caaggggagc  119100 ctctcccctga gccctgtttc tggcacccac atttgttctc ccgattaggg ccaggtatgt  119160
tgtgggaagg gtagagacga gagcatctct gacttcagtg tgaatcctaa gattacgaac  119220
```

```
tgcctggcct tgggccaatt acttaatctc tcagaatctc tgttttctca tctataaaat    119280
ggggataaga atactgtgta ttccacagga ttgtcataag gacaaaggag ttaatgtgta    119340
taatgctcat agaacaccgg ctggcatgga gaaaacagtc ggaatatgtg agcttaaaaa    119400
attagaaagg aaaagaatgc cctgtcctga gggatagcag ggattagaga cgtggccctg    119460
tgcagggacc cggcgctcag cagccattgt ctcccagcgg tgtgtgtggt ggcctccatg    119520
ggttgtgcct ggctgttcta cagatgttct tttaggaact tccttctgtt acagtccagg    119580
aatcaggact ggaatggcta catttttctcc cctaacttgt tattgtcttc tagtgcagga   119640
aagaggaagt gaagggaaat gcatgttcgt tgtcattttg ctaatattcc tgcttcagtt    119700
aataaaattg atgaaaacat acaagtcttc agagattccc agaatacttt ccctgctagt    119760
cagaatctgg aagtcctttt cttgccttat gataacctcg ttccttgcag tagctccata    119820
gcgggaaagg tgatttctat ggattgtaga tttcctggcc tcgaggattt tgtaatgtgt    119880
tgggtttgct gtttgaatca gtagaatctg ggggatagtc tacttaaacc tgcatattga    119940
gggggcattt ggtaagcgcc tctccatgtc aggcactgct ggtaccacga gcttcagaca    120000
gggcactgtt atgggtctcc tgccctgatc ttctggctca aaccagcgt ttgttcacct     120060 cctcctctgg ttcccatcat gccctgggcc cgggtactgc ttcttccttc catagctctc    120120
atcctttaga aagacgccag tcattcattc actcatttaa caataataa ttgagtgcct     120180 actatgtacc gggctgtgga ggtggagaag aaaataagat agacagtctc tgacttcttt    120240
cagtttccag tcttacattt taaattttaa tttcattagg gaaactgttt ctgacctttc    120300
ttaccagaac agatcttgcc atgccaacct tggagcacca cacacctgtt ctttagagga    120360
gctgaacaaa ttgtagcttt ccatttaatt gtttatttgg gagttttggc tctgtcgtta    120420
ccctctgagc tcctggaggg taggagccat atgcctattg aataagcact tgtcgaatga    120480
ctgaagcagc aagcgcccgc acaccggtcc cacggccccg gctcagcaga cgttggctgt    120540
ctgagagctc ggatcttggg tgctgtgctc agactccccc aatctcttcc acagaaatct    120600
ccaacctgct ggtggctact aagaaagccc aggagtggca gcccgtctac cccatgagcc    120660
agctgagttt cgatcggatc ctcaagaagg atctggtgca ggtgagtcac ggctgcaggg    120720
tgtgggccag ctgtggtcct gcctccccac gatggagcag cttggggatc tgggggaagg    120780
aaggctgtgt ttggggaaat cttagtagaa aaagaacagg gagactttcc tttgatggca    120840
aaagccgtac aaccattgcc tccatcctct tcacccttgc tgatgctcct cagagacatg    120900
ttttgaggta agtggtttgg tcaggctttg tggggttacc tagaacagca gggaccttct    120960
gtggtgagct gaagggggtgg cagggcagga ggtggctctc cacaggggag catggccatc   121020
acacctcgct gcctgcagca ggctgtgtga tggagcacct ccagagttca gtcctgcact    121080
ttctgatgat gcttccagaa ggagcagagc tcaggaggag agaacacagg gagggaacaa    121140
gaggacatgc acactctggg cctgaaggag aactatcttg agaaacagat cccagtcttt    121200
ggaggccttt ttgcccagaa tctacaggct gagcggggag cccaggatct ccccagggggc   121260 tgccctggag ctgttgctgg tggtgtgagg cccaggaaaa gcccactttc tgttctgcca    121320
ccgctcccca gccctgttgc ataggggccac gcgttgggggt atcagggaga tggtgcggca   121380
gccttggaga gaagcaagca cggggccact caccacctcg ggagatggca gcgccttgga    121440
ggtgttggag ggtgaggcgg aagctgcctg ctgtgaagga gcctggggag agtggcactc    121500
gggggtttgt tactttacct ttttcagtga gtccccgaga ttgttggatg gggcttgagg    121560
gagtggaaat ccacagctaa actgcctcac ttccctcgtg gtacatttct tcaccaaagg    121620
```

```
cccatcattg ttctctattc ctctcgtggt gtgagagctg tgtcctgaga ttacagtcac   121680
cagagccaca gtttcatagc ctcttttctg tgtagaactt gacatagtct gtggggcctg   121740
cctcttttcc cttgcctcga gcctccaagc aggtaaccac catcctccat gccttccaca   121800
tccacttagc caacagagat caagcattac acgtgcgagg cacgattgct gcttcagcag   121860
gctcctgtct attttgaggg ggtaatcacg ttagcaagag tcaagttcca aagtagggaa   121920
gtacagcagg atgtggacct aatcttgaga ggacggagat agcttcctgg gggaagcggt   121980
atcaaagcag agtcccagac caggcacagc ggctcacaca gtggctcaca cctgtcgtcc   122040
cagcgctttg agaggccaag gcgggaggat cgcttgagcc taggagttca agaccagcct   122100
gggcaacaca atgagatccc atctctacta aaatacaaa tgaaaaaatg agctgcgtgt   122160
agtggtaagc agctgtagtc ccagctactc aggaggctga gttggaagga ttgcataagg   122220
ccaggagttt gaggttgcag tgagctatga ttgtgctgct gcactcccgc caggtgttag   122280
agcgagaccc tgtctgggga aaaaaaaaaa tcagggtctc ctcctggagg atgaactcaa   122340
gtagctaggc aaggtggagg aacagcatc agaggaggat gaagtgggcc atatgggcct   122400
ttgtgggtcc ctgcagaatc ctgacagcat ggtgtcatga cttggccacg ggaagagcaa   122460
ttattctgaa agcatatggc ttttacggga tgttctggga atacagcttc ccataacctt   122520
gatggatcac ttcatgacag atgcagcttt aatgaatagc caaagacctt gccaggatac   122580
agcagacagg gtggatgcat cgccattcgg ctctgacaga taacaaatgg tggcatttgt   122640
gcaaattaat atacctgatt aacaatggtg tatgttccta tgggggataa gactgattcc   122700
ctaggtatca gtgacagtcc cttttctgca tttccagggg gtcctcaaat aatagaataa   122760
tggatcttca gtttacaagt tttgtggtgc taatgtcaac aacttgacat tgcctaagtt   122820
tcgtgaatcc catttcgatt tccaaatatt aagaatttta aaagcagaat tattgcaact   122880
tgaactggaa gggtcctcag aaatagatca tggtatggct agggctttgc acggatcatc   122940
tcattcagtc ctcctgccac tcatctgggg gtattgttcc ctttcacatg tcaggaaatc   123000
caggacacat caccccaggc tccaccttca tcttcacatt gccatctcct ctgtgaggtt   123060
gccagggcaa atgcaggtgt actttgcacc actaatttta aatcctagcg tgcatgcaca   123120
cacatgagca cacacactgg ataaatggat gggaaacaga tggttccagt gtgagaaact   123180
gtgcctacct gtgccagagg gcttcagata acacatggat ccaccagatg ggtttctacg   123240 catcccccg tgtgcctgag tctgtaccag gagcctccat ccctgtttcc tggtttgatt   123300
cttaccacag ccctatgagg tcagtaccat tattacctcc atttgcagaa agtgggcaga   123360 gattgcccc atgtcacatg ccagcgggt agtagagctg ggatttgcaa gcctcttcac   123420
agggtagcac agcctgtgag tagaggagct gcctgggggc cctctcttg agtcttctct   123480 ggaggcctgg ggtgggaccc atgtggctgg ctgttgatgg ccctgtttgc agtgtcctga   123540
catgttagga ctgtgttttg gccaaaggct gttcctaggg gtagaaagca aggagccgtt   123600
tagggagtag gaggactgtc tcctggggcc cagcaaatgt caccactgtg tttggccaaa   123660
tagcttgttg ttttctctgg aggcctgggg accacgagct ggggcaggga gccctcttgc   123720
ctttgcccca tccattgat agtccatgtt cccattgagg acccattccc agacggtcca   123780
tcacttcagg gcacagagag gtcacccagc cttctgcttc ttccctcagg gcgagcacct   123840
tgggagaggc acgagaacac acatctattc tgggaccctg atggattaca aggatgacga   123900
aggaacttct gaagagaaga agataaaagt gatcctcaaa gtcttagacc ccagccacag   123960
```

```
ggatatttcc ctggcaagtg tcttcctctg aactcctccc ctcccctctc ccgtttctgg   124020
agccagtgga acacaatggg ttgagaagaa cccttgccct tcttgtggcc cagtggtttt   124080
caaacttgcc ttttactcag aatttttttc tccacatatg atcttagtgg accctgcatg   124140
tagagtaagt gaggtgggtt gaacagctcc tcacactcag cctgtgccct cccttccacc   124200
cccaaccccc acctttccta aggacaggtc caggtggctg tgctgtggag ccctaggact   124260
ctggccaaat ggttcaaagt tcctgataca gtccatggct ctcaccacac agtctggaaa   124320
acgaaagccc agaggagtaa aaggactcac ccaggattct acagactatt agagtgacac   124380
agtcaaatct tgagcagaga tcggctgcct tcatttcccc tttgttccag catagtgcta   124440
aatatgggta tttcccagag ctgaaaggaa gagagagagg tgggcatgag tatccagtgg   124500
gaaaattctt agccagcttc tcccaccagc cctgctctgc atcctgttag gttttctaaa   124560
taaacctcac atccctgcca ggttggccca gagaacaagg cttggcagtg cctctggaca   124620
gccaaggcca gaggattgat gttcagggcc tggggtggcg acagtggtga gctttcctgg   124680
gtccactggc tttcccctca acagagcccc tggggagcag ccccctggag gctggcctga   124740
gacattccta tgtcctgctc gcccacaggc cttcttcgag gcagccagca tgatgagaca   124800
ggtctcccac aaacacatcg tgtacctcta tggcgtctgt gtccgcgacg tggagagtaa   124860
gtgtgttctc tttcaaaggg gtgggtggcc tggctgggga gcttgggtgc tgtggagatg   124920
gtggaggctc ttcccaccct cacgttgccc aggcttcttg cctttctttt tgcagttgag   124980
gagattgagg gactgagcag gtcatttgct taagttaata gtggaggtgg aactaaaacc   125040
aattgctttt cattcatttg tgtaatgttt tcttgtcaac gctggccaag aaccctacac   125100
tgtgctagac ctgggaggct gaggtgagtg aaatgaggtc aaggccacaa gagtcaggcc   125160
caaggagctc tgggcaggtg agcgaggtga gcgcacccca caagcagcaa gacgctggct   125220
cctcgaatgg actggcttcc attttaacca caggcaggct tggccctttc ttggttgtca   125280
agccactgag ccggtgggcc cttgggctgc tgctgcacac tgagatggag gggtggcctt   125340
ggcctctgag ttcctgacat gtaagtttgg aagaagagcg attttttttt taaccccaag   125400
tgacttcttc cctgtggaat ccaacaatgt gagctgttcc gtgtactcac acaggagtcc   125460
tgttgagagg gaagttttgc cgtgtgagcg gcctgacctc tgcatcacag tgtgttgtag   125520
aacagcagca gtggtggcgg ttgttcccag agcccttgtt ctctgtgtca ggccctccgc   125580
caaggctttc caggccttgt gacatttagc cgccatctgt tattacagat gagggaattg   125640
aggctcagaa aagtgtcact tgctcagtgc caccgtttag aagaagagct tggggttgaa   125700
cttggccttt ccagctctga agcccctgca ccattgcacc cccaaggat atctgtgtac   125760 tctgaggccg agtagtgtcc actgaagtgg actgtcgtaa ggggatgaag gagaggaccg   125820
tgccacagac caggttccag acatggctat ttttatgcct acagatatca tggtggaaga   125880
gtttgtggaa gggggtcctc tggatctctt catgcaccgg aaaagcgatg tccttaccac   125940
accatggaaa ttcaaagttg ccaaacagct ggccagtgcc ctgagctact ggtgagaat   126000 gtcctgatgt ccataatggt cccaccagaa accagagtgt cctgggaggg gtggcaggaa   126060
ggaggtgcta gccaagcagc tagaggggcc tgtccttggg ttccatgggg ccagggctct   126120
gtggttgaac aaaggtgtgc ctggtgctta ctgaagatgg tcgtttgggg ccgttccctg   126180
tgctcacatg agttctgttt agtgggaaat gttagcacgt cagagggccg acttgcatac   126240
tgcagcatat ggatgcaag gctgaaagca gtgcagtacg tgttgagtga atgagtgaac   126300
tgccagcatc tagtagctga cgtgtggagt gctcaccatg ggtcagctgt tcaggcgttt   126360
```

```
cacagattct aatcagtatc atgctcacga agcccaatga gatacgtgcc actatttagc   126420
cacattcagt gatgagggag ctggagccaa ggggcacctg tgatgtgcct aagtcacaca   126480
gatgattggc agcagggcca ggctgtccag atctggctgt agctgggggt aggaagagat   126540
gacctgaggg accagggttg gaaatagaat gcgggaagga gcagcttggc taaacttgac   126600
ctttttactc tgcaggagga taaagacctg gtccatggaa atgtgtgtac taaaaacctc   126660
ctcctggccc gtgagggcat cgacagtgag tgtggcccat tcatcaagct cagtgacccc   126720
ggcatcccca ttacggtgct gtctaggcaa ggtgtgtctc ccctctcttc cctctggccc   126780 cacccccgagt caggggcaag tcagcagaga aagggctgg gctggggttg gtctcctttt   126840
agagagtcat ttttttttttg tattttagta gagacggggt ttcaccatgt tggccaggat   126900
ggtcttgatc tcctgccttc tcttaagtcc ttgaacgagc cccgttcgt cctcctgccc   126960 tgggtgatgg cccccaccct gggatgtttt gctgatccta aggccagggc ttcagaagcc   127020
tggcttcaca cgaccctcct ggggagcttg gaggcaggga cccatctgct ggctgtgacc   127080
cagactgatg tatcagaagt gctggtggtg gcttggaggg ctgcacgcct gcaggccccc   127140
cgcacagggc ctatgtggcc atgggccatg tttgggcaca ctgcttgaag tagttccttc   127200
attggctcac tgttctggct gcagtgacag taattgaatc cctaggagat cccagaaact   127260
gctccatcag tgtgtctgtt gtcttccaga atgcattgaa cgaatcccat ggattgctcc   127320
tgagtgtgtt gaggactcca agaacctgag tgtggctgct gacaagtgga gctttggaac   127380
cacgctctgg gaaatctgct acaatggcga gatcccttg aaagacaaga cgctgattga   127440
ggtgagcagg tgtttcccgg ggcgtgaggc aagtgagggc tttcaggtgc tcgtgggctt   127500
cccaggagtt gtcggaagcc tggcactgtg ggaagagatg ggcatgggtt tgaatctctt   127560
cacgggccta ctgggtgtgt gacctcacaa atgtaactga acttccgtga gcctcagttt   127620
catcatctat aaaatgggga taatcagtaa ctacttgtag ggttgttgtg aagattaaat   127680
aatgcatata gagtgacagg catgcagtac aagctcgata gatgttatag tattatttat   127740
ctgagatttt aagtgcctgt tattcagcaa aattaccaca caaatacgta tggagttcct   127800
attgtgtatc aggcatcaag cttgggaaaa gctggaggtt cactataaaa taagatacag   127860
gccttgcctt cccttgaggg ccttagggta tggtagggag ttaggctaaa ataacaacgg   127920
taagaattcc agaaagaata cctgaaagtg tcaccctaag agccctgcaa attaggtagg   127980
atggtgtcat taccctcatt tgacagatca ggtaactgag actcaggtag ccccacttac   128040
ctgggttcct cagctagaat gcaaaacagg cgaggtgtgg acctcctcca aatctacctg   128100 tggaaaagt ggagactcta actccaaagg ggtaaagtag taaaaatcac aatgaaagac   128160
cattgtccct tcatctcagt gactgcaatt ggaatgtgct cctgttgttt agaggggca   128220 ggcatcagtt tcggctgtga gagcctggtt tcagtgctgt gtcgggagcc tgggtagttt   128280
ggtgtgcctg gccttgagtg tctggagtgg ggaaaggaat aacagtgatc aggtgggaaa   128340
ggccatttgg gttcagattt ttaaagtccc tgattccagg ctgcagaacc tacatttttac   128400 tgggggtggc atgggacaag gaaggatttg ggtggaggag ggagggggctt ggaggtcggc   128460 cttgggatgt tcttctggat gcagtagctg ggatggacag aggagagacc tggagggaga   128520
caggggcccc gagtctctca gcaatgggag ccccatgtcc ggaaatggca gcggaagtcc   128580
agagtgcagg gtgggagata ttgaagaggt agaacctta tgacttgcca gttaatgatg   128640
gtgcaggact tgggaaagga tcttaaaccc gcagggaaac catcagatct acagatctgc   128700
```

```
tatttggaat tttcagccta ggcttttggg aaattcatat ttattttaa cttccttgga    128760
tccttggaaa tgaaacaaca tacccttgt catcagtcag tatttattga gcacgtgctg    128820
cgtaccctgg gctgaacagc atacagggtg gtgtaaggaa ggacccgtgt ctttaataaa    128880
atagggtct ctctccacct aagtcccctt gggttagatg gcttttctgc aggctgcact    128940
gacgcaggga tgtgtgagtg acactcaagg acaagagcaa ttctcagctc cttaattcca    129000
gtcctccctc ctccctgtcc tctgggcct gcccacccca ccccacccca gggcccacgg     129060
ggaccagaga ggaacttagt acccttggag tccagctatg aagtagaaac tggaatgcag    129120
tggtttcact tcatcttcca aaagtagcat aagttcttgt ttctaaaatt taaagtaata    129180
aacagttgaa gaaattttt aaaatgaaac tattaaaaaa agaaacagc aatcactgca      129240
ttcttgtcat ccctgaccac tgttaacact ttggcatttt gtcttccagc ctgtttgtat    129300
ctctctttt taaacaaaat tgggggccatg ctagatagag ttatataaaa ttctgagttt    129360
tttcatttaa tactgagaat gctttcctgt gagattaaat cataattttt acaaatttaa    129420
tgtaagagtt aattgttttg tttaatttac ttgactaatt ttatatttgg catttaagtt    129480
ttcaaatttc cagtgttctg tctaattctg caggaaacat ccttgtacat aaatatttgt    129540
tcatatctga tttatttctg agtcattcag tcattgaagt taatgcatca gagggtttga    129600
agaatctgaa gattttttgta catgttgccc aattgtattc cagaaaggct gcatgccttt    129660
acttgaatga agcttttttgg gactgggcta tagtgcccag tctccttgaa tttggactat    129720
tcagtattag gactgtgatt tccccttgca agaataaggc agcagtaaca aacacttacg    129780
aaatctacct gtaagtggag atgttgagaa tcgaatgagg aattggcaat tccacctgac    129840
ctggggctga gaagtttgta ggtggttcct ttggtttctt ccatgtgccc ctcttgttta    129900
cagaaagaga gattctatga aagccggtgc aggccagtga caccatcatg taaggagctg    129960
gctgacctca tgacccgctg catgaactat gaccccaatc agaggccttt cttccgagcc    130020
atcatgagag acattaataa gcttgaagag cagagtaaga cctgccatgt gctgcttaa    130080
cccagcttgg ggagaaacag gagcctgggt ggcaatccct ggcaatcgac tgcctttcac    130140
tctgttttct tttctcttct gttagatcca gatattgttt cagaaaaaaa accagcaact    130200
gaagtggacc ccacacattt tgaaaagcgc ttcctaaaga ggatccgtga cttgggagag    130260
gtaagttaca cccgtgctgc ttgctgctga tggcagagcc ctccgccatc cacagcgcca    130320
ctctctgcac gtacagctgc tctccattct tttcattct ggggccaggt ccatgagcga    130380
aagcacctta ctgcatttgg gggccacttt catcacaagg gattgtgtct ttctccatgt    130440
gacacacggc acggacggaa tgcacgtccc tgcctgcatg cacgactgtg tatgcacacg    130500
ggactctggg cagctccctt gagagacttg agttttctct acaggacaga agagaatgga    130560
aagagggaga gatgggggag taggtataga tatggtggaa taggaaaatc cttgcctctg    130620
actttcccgg gcatatatat cctgtaagct tctctctttt tcttttgccc ccgagagaca    130680
gggtctcgct ctgtgtccca ggctggagtg agtggtgtga tcatagctca ctgcagcctc    130740
aacttcccag gctcaagcaa tcttcctgcc tcagcctcct gagtagctgg aactacaggc    130800
acacgccccc atgctggcta atattttta ttttttattg tagaaatggg gtcttgctat     130860
gttgactagg ctgctctcag actcctggcc tcaagcaagg aggcctccca aagtgctggg    130920
attataggca taagccacca tacccagccc tgtaaggctc tttagagcag ggataggttt    130980
attgcacaga atcccaaaat agagtgtcag cgtttctttg gaccttaaat gggagtttcc    131040
aaacagttaa ttgtgactag agaagctact gagatttgtg tctttataca gattttctgt    131100
```

```
agtctggtta atgaaacaga cttgatacat ctccaggatc tgctgtgtgc cagccactgt 131160
gccaggcatt gtcagaagca tggcatcctt agttccccc accgtccccg aggccagttt 131220
ctgtatgcag cgagtgcatc aggagccagc tccgatttgg ggacttggcc accactgtcg 131280
ctgtcaggtg gcttggctgg aacctgatct cacgtcttct aaagactcct catgcatttg 131340
ctcttttcag ccatgctgtg gggcctgtcc tgtaacgtga gcccagggct tttagagaac 131400
ggcagttgtc ctgcaggccc agaaataacc ttcatttcct gtggtcatag aaattgggat 131460
tgatgagttg gttcatcgtc acctgctact ttgtcttggc tcagtaactg aggggacagt 131520
ttgtgaggcc aagagagcga gggggctgta gtgagcaagt acagtccagg tgagaggctt 131580
ctgcctgcaa ggccagacag cgagaacccc tggccctcag gggaacggct gtgaggagca 131640
agacttctgt gtgttccgtg gcctacgatg gggcttccct gataacagca catgcatctt 131700
tccctccagg gccactttgg gaaggttgag ctctgcaggt atgaccccga aggggacaat 131760
acaggggagc aggtggctgt taaatctctg aagcctgaga gtgaggtaa ccacatagct 131820 gatctgaaaa aggaaatcga gatcttaagg aacctctatc atgagaacat tgtgaagtac 131880
aaaggaatct gcacagaaga cggtatgtta tgcaaggctg gggtccggtt taaagatttg 131940
gtgactgtct agggtcataa aggccagtgc aaaacaggca ctccgtggcc ttacctgggc 132000
gtctgacatg ctagctggtg gttcccacac actctcaagg cttccaagtc atatgtcaaa 132060
tccctcagca gctgcagggc tcctgaggag gccacccagg cccctccatc caggggctgg 132120
ttccagcact gtctctccac gtcacttgca cttatgcctt atgaaactga ttcctactct 132180
acctccaccc acttcctgtt ctgatccaat actagccagg gtatttcatt ttctagttgt 132240
ctaaatcaaa gtgcaagta atatttacta ataattgtat cttatttgca agccagcatc 132300
tactcatggt agtgaaattg acagctgatg ataatttttt tttttttttt ttttttttg 132360 agacggagtc tcgctctgtg gcccaggctg gactgcagtg gcgcaatctc ggctcactgc 132420
aagctccgcc tcccgggttc acgccattct cctgcctcag cctcccgagt agctgggact 132480
acaggcgccc gccatcacgc ccggctaatt ttttttgtatt tttagtagag acggggtttc 132540
accgtgttag ccaggatggt ctcgatctcc tgacctcgtg atccgcccgc ctcggcctcc 132600
caaagtgctg ggattacaag cgtgagccac cgcgcccagc ccgataattt ttgaaaacag 132660
tcatttgcct gtggtttaca gagcactctg actgttatct cagtgagtgc ttatgcctgt 132720
gaggtaggta caccattgtt accatctcca ttcactgctg aggatcttga ggcataagag 132780
gtcaagtaac atgcctgtaa tgaaggggcg aagctggcgt cacctcaggg cctctgtctc 132840
atatcctgtg cccttgcctc tcccatggtt ccctcatttg gcagcctcag actgatggat 132900
gttttttcta aacaggagga aatggtatta agctcatcat ggaatttctg ccttcgggaa 132960
gccttaagga atatcttcca aagaataaga acaaaataaa cctcaaacag cagctaaaat 133020
atgccgttca gatttgtaag gtaaaaaata aagacatcat gttacagatt aagacatcag 133080
gcactctgtc ctgggtaatt ggtttgtaat ttgactctaa gtgggtaagt ttatgataat 133140
tatactgttt gttttttctct gcattattta gatgaaaagt tagcttctac taagaaagta 133200
aacggattta aatatggtta ttttaatgtg tatttatttg aatcagtttg ttcttaatat 133260
tcttgcataa aagtcagaac caaaaaaatt gtcagtgata tgtgaatgaa atgacatttc 133320
tattttttct gatgaagtga tagataatac aatctaaagt gactttagca atgtgcttga 133380
cttttacttc tctctctcag gggatggact atttgggttc tcggcaatac gttcaccggg 133440
```

```
acttggcagc aagaaatgtc cttgttgaga gtgaacacca agtgaaaatt ggagacttcg    133500
gtttaaccaa agcaattgaa accgataagg agtattacac cgtcaaggat gaccgggaca    133560
gccctgtgtt ttggtaactg aatcaaacca ctaggtttta tcaatgcttc atagagttta    133620
cactgtttta ataggcccctt tctggctata ttaatgtgtc tcattcctct ggcctgactc    133680
aaggttagag aaggtttaga acatttggaa ttgattgata tttatcttca agaaacacac    133740
ctttcagcct gtttcattga aagcagccta tataaatgac tgagcttcat atgacaccgt    133800
cttccaagga atgaaagaaa tctaaccacc agctcaacat tcctagcttt ccaggagagg    133860
gcattcatct gatgcagttc ttaaaactgt gagcaggtgg agagaatcta gttcctttct    133920
taaacacatt cctgcagagg gaggctgtag gacagagtgg gcattgcaga ttcagggaac    133980
tcctggacag agcagagcaa aacctacggg agacctggct gtctcatgaa tcaccagagg    134040
ttcccaggtt agaaggccac acactggcta caaccatgtc tcagccggga acactgtcca    134100
ggggagaggc tgcttacatc tctaccgcac cctgccacgt aaccacataa cgacataacc    134160
aatcagcact cccctaggtg catcctacat ggacacaaac atagacctct cccacttatg    134220
gagcctaaac ttactcattc attcatttaa gaaaatgcat caaggtcctg ctttgtgcca    134280
gtactggaga tatggtgaac aagtaggccg agtttagagt ttaacaggct aggcagccaa    134340
cggcatggag caggaaacat acagaagggt tcgggcttgg ttttctggaa gtcgtgagta    134400
ttcagaagaa acctgaaaga ttcatgcggg tttagacaga cggttgctag acagcatgcg    134460
tgactaggaa gaatgagaca agagcagtcg atttcccagg aactgaacct cagtgaggtc    134520
agatcatgga ataggaggtt tgcaggagga agcttgagtc atggagctgg gacttcatct    134580
caagaacaat gggatgctgc tggagagttt aaggagggag actttgtttt aaaaagacca    134640
ccactgaatg aagggaacaa gattggagcc agggagtctg gagccaggga gtctggagcc    134700
agggagtctg atttggctgc ttcaacagct caggccagag ctagtgacag catgaattag    134760
gacagggact gggagagtga cagtagggtt tgagagaagt gagtaggttc aaggagtata    134820
taaggagatt gggtgcggtg gaatgccttc atttttggct tgggcaagtg ggtgtcattc    134880
agcaaagtag gcaatgctgg aagaggattg gacagcgatg ccacattgtg cagtgaggcc    134940
actgctgtct catttagagc ctgcaggcaa atcagacctg gggctcatca ttacacggcc    135000
acctcctccc ataccctgag agcatgttct cagtgaaatg aagagcacag acttggcgtg    135060
ttattttagg gcagatacgt gctaccgaga gcctgtaaag gataccgtac tataggtcag    135120
atgtgcacca tagcagcgta tacatggtat gtgtaaaata tataatacac agtcagatgc    135180
tgtattaaat tataagaaaa accgaagagg tgatttttca gttatcctgt aatgtcggat    135240
ggagtgtgcc tcccaggaaa tgaagttttg tgttctgctt cctttcaagg tatgctccag    135300
aatgtttaat gcaatctaaa ttttatattg cctctgacgt ctggtctttt ggagtcactc    135360
tgcatgagct gctgacttac tgtgattcag attctagtcc catggctgta agtcctactt    135420
ttctcttcat ttgaatccag tacccattta aaatgtgtcc atccctctgc ttggttaact    135480
tttgttttta aatggaatcc aatgaatgta ttataatgga aaatgtcact ttcccattaa    135540
cttggtttgc tacttgacag ttatttgtga atctctaaag tcttgctttc acaacgagcc    135600
cggagttcta taggatgacc ttgactctca aggatcttat ctgtgtagag atgaagggca    135660
gttttatggg aaaatgagca agttaagtgg ggtagcactg ggtagggacc agccttgtct    135720
gtgcctcctt cattcctaaa tcagatcatt ttccttgggaa cagactcctt gaccagcaca    135780
agcacaagga gtggttggta gagtctaaga cactggttag agacagatca ttgaaagcta    135840
```

```
ataaggattt tggattttta tttaaagtta ctaaggagaa aagcctttt  attgctactt   135900 aaatttccag ttgattgtag aaatttcacc ttaatctgtt tggcatttat gtaaatactt   135960
gcaaagttaa acgttttgtt tgattttatt ttatatagtt gttcctgaaa atgataggcc   136020
caacccatgg ccagatgaca gtcacaagac ttgtgaatac gttaaaagaa ggaaaacgcc   136080
tgccgtgccc acctaactgt ccagatgagg tatctatggg ccacgtcaca gtaataacac   136140
tccatttcta ttatgttttc gcagcttgag ttgtccagca atgggtagag gggagagcga   136200
ggaaatgatg cagtgaagtc cttgtaaaat agttttctga agctgaattt cacataagat   136260
aactgagaaa tcgcctttgg ggctagatga tagccaccag ttaggttcag agcaaggatt   136320
ccctccaaaa gccagcccct ctttatccac ttgcttgccc cagagggaca ggttttggtg   136380
tagccttagt gtgacaaata catataattg cattttttgt gtgtaagttt atcccactta   136440
ttagcattta taattcagtt ttctaagtga attgagcctt taatactaaa ctcttgagac   136500
tgtgtaagac acactgaaca gtatgagtca gagagtgagg cagccagtct ggaaagttca   136560
agtctgaact gagattctgc ttcaccctct aactggttta caggaatgac ctggatttta   136620
ttgcagccag tcaacccttg agcttctcaa atgttaaaat attatttatg aactagagtt   136680
gtatcccatt ttctgtgttt taaactattc aaatactctt gttttctag  tctttaagga   136740 aaagtcattg catttccaaa attattttct tactcttgat atttctgtta ttttttaaag   136800
ttcccagatc taacatttt  actgttgtta cttctttctt tttacaggtt tatcaactta   136860
tgaggaaatg ctgggaattc caaccatcca atcggacaag ctttcagaac cttattgaag   136920
gatttgaagc acttttaaaa taagaagcat gaataacatt taaattccac agattatcaa   136980
gtccttctcc tgcaacaaat gcccaagtca tttttaaaa  atttctaatg aaagaagttt   137040
gtgttctgtc caaaaagtca ctgaactcat acttcagtac atatacatgt ataaggcaca   137100
ctgtagtgct taatatgtgt aaggacttcc tctttaaatt tggtaccagt aacttagtga   137160
cacataatga caaccaaaat atttgaaagc acttaagcac tcctccttgt ggaaagaata   137220
taccaccatt tcatctggct agttcaccat cacaactgca ttaccaaaag gggattttg   137280 aaaacgagga gttgaccaaa ataatatctg aagatgattg cttttccctg ctgccagctg   137340
atctgaaatg ttttgctggc acattaatca tagataaaga aagattgatg gacttagccc   137400
tcaaatttca gtatctatac agtactagac catgcattct taaaatatta gataccaggt   137460
agtatatatt gtttctgtac aaaaatgact gtattctctc accagtagga cttaaacttt   137520
gtttctccag tggcttagct cctgttcctt tgggtgatca ctagcaccca tttttgagaa   137580
agctggttct acatgggggg atagctgtgg aatagataat ttgctgcatg ttaattctca   137640
agaactaagc ctgtgccagt gctttcctaa gcagtatacc tttaatcaga actcattccc   137700
agaacctgga tgctattaca catgctttta agaaacgtca atgtatatcc ttttataact   137760
ctaccacttt ggggcaagct attccagcac tggttttgaa tgctgtatgc aaccagtctg   137820
aataccacat acgctgcact gttcttagag ggtttccata cttaccaccg atctacaagg   137880
gttgatccct gttttacca  tcaatcatca ccctgtggtg caacacttga aagacccggc   137940
tagaggcact atggacttca ggatccacta gacagttttc agtttgcttg gaggtagctg   138000
ggtaatcaaa aatgtttagt cattgattca atgtgaacga ttacggtctt tatgaccaag   138060
agtctgaaaa tctttttgtt atgctgttta gtattcgttt gatattgtta cttttcacct   138120
gttgagccca aattcaggat tggttcagtg gcagcaatga agttgccatt taaatttgtt   138180
```

-continued

```
catagcctac atcaccaagg tctctgtgtc aaacctgtgg ccactctata tgcactttgt  138240
ttactcttta tacaaataaa tatactaaag actttacatg catatgcctt ttaatattaa  138300
gatttcattt tcaaagcatt tcaaacaatt tgcttacata gaaaaataac agtatagttt  138360
tggggggagg aagggtggg ttacggtcct tactactaac aaacaaacaa acaccacttg  138420
atttgcactt cttcactgtt gtgcccagtg attgataacg gggcacaggc cagtatggat  138480
ggcatgtcca ctgtgctgta gtccagacac ctttgtttgt ttgttttagt tccttcaacc  138540
tcttcctgct ttgactgact gacttttttgc agctctgttg caaaattcac catctttcct  138600
ttcttctgtt tgtttgtttg tttgtactat agtggaggtg tgactaagca ttgaagaggc  138660
tgaatgcaac aggaaaatgg gaagagaag tgcagggcct gaaaaaccca ttagtcatct  138720
gctatatcac tgaatgatgc ctaattctta tcagttactt ataggtagta tacttagaaa  138780
ttaccttaaa ctttctagct gtcagtcatt ttccaacaga agctagtata tgcaataaat  138840
tagaccaagt gaaattcttt acaaagcata caacatatgt accaattcta gacttcataa  138900
ttaaaacagg atatccacat catagttaaa aataacaagt ccccaaagtg acgagatatt  138960
taatgatctg atttcaaaaa gccccggatt gagatcccaa attccctatc aattaattac  139020
agtcttataa cataaacaaa cttagaaatt tctagatggc aaaaggtttc tcatgcattt  139080
aataccaagg tcttcaagaa atggtgatgt caaagtcat catagtccat aaagataaaa  139140
cttctttcac aagtaaattg ggttaaataa ctgattttc accctaacac actatcaaaa  139200
agagtgagag agaaagcaga gagtgaggta tagcttatta gctcaaaatg gttataaata  139260
ctgtgactcc ttaagactcc atcagaaagt gcagtattga ctgctttact atactatatt  139320
gtggaaataa tagggcattt agtgatcaaa ataggcccca ttctagtcat tagatcatta  139380
ctagtctacg ctatgaaatg agcacagaaa cccatgttcc tttccactta caagtctgtc  139440
taaaggctaa aggtctgtct ttaggtgaat tgaaaggaat agttgctatt agaattagtg  139500
ctattagatc agggatcagc aaactatata taaatggcca gatacttgaa attttaggcc  139560
atatggtctt tgtaggccat acagtctctg ttgaagctaa tcagttctgc ccttgtagcg  139620
taagagtgcc acagacaaca cgtaaatgaa tgagcatggc aacgtcccaa taaaagttta  139680
tttatggaca ctgaaatctg aatttcatat aaatttcatg tcataagttt tctttttcc  139740 tccaaccatt taaaaatgta aacattagtc ttagcttgca ggcagcacaa aagcgggtgg  139800
tagaccaaat gtggacccag ggtgtagttt gccaaaccct tttattagat caccaaagtt  139860
acttttctta aaataccttc tattttcac agaaggtata aatggtaaac aacatcttaa  139920
agcatcggta gtagtggata ccttggatat cactgtcact ctcttaccgg gtttaatttt  139980
gcatggctgg tgtgggcgta attgagtgtg catgtagagc atctttataa tattaccatc  140040
agcacatttg gtacttgcac ccttgtagtt ctaggaaaag tcctaaaaat ctataaatgc  140100
aattacttct agggaaagta aattgaaatg cacattggct tataagaaac tcattcttct  140160
aaggctcagg aaacaacact gtttcccatt tattgcttca aacttctttt atatatggta  140220
tcagaattat tcccagtcct aaatcaagga atattggaac attgttagtt tctccaatgg  140280
at                                                                 140282
```

<210> SEQ ID NO 4
<211> LENGTH: 1154
<212> TYPE: PRT
<213> ORGANISM: Homo sapiens

<400> SEQUENCE: 4

-continued

```
Met Gln Tyr Leu Asn Ile Lys Glu Asp Cys Asn Ala Met Ala Phe Cys
1               5                   10                  15

Ala Lys Met Arg Ser Ser Lys Lys Thr Glu Val Asn Leu Glu Ala Pro
            20                  25                  30

Glu Pro Gly Val Glu Val Ile Phe Tyr Leu Ser Asp Arg Glu Pro Leu
            35                  40                  45

Arg Leu Gly Ser Gly Glu Tyr Thr Ala Glu Glu Leu Cys Ile Arg Ala
    50                  55                  60

Ala Gln Ala Cys Arg Ile Ser Pro Leu Cys His Asn Leu Phe Ala Leu
65                  70                  75                  80

Tyr Asp Glu Asn Thr Lys Leu Trp Tyr Ala Pro Asn Arg Thr Ile Thr
                85                  90                  95

Val Asp Asp Lys Met Ser Leu Arg Leu His Tyr Arg Met Arg Phe Tyr
            100                 105                 110

Phe Thr Asn Trp His Gly Thr Asn Asp Asn Glu Gln Ser Val Trp Arg
        115                 120                 125

His Ser Pro Lys Lys Gln Lys Asn Gly Tyr Glu Lys Lys Lys Ile Pro
    130                 135                 140

Asp Ala Thr Pro Leu Leu Asp Ala Ser Ser Leu Glu Tyr Leu Phe Ala
145                 150                 155                 160

Gln Gly Gln Tyr Asp Leu Val Lys Cys Leu Ala Pro Ile Arg Asp Pro
                165                 170                 175

Lys Thr Glu Gln Asp Gly His Asp Ile Glu Asn Glu Cys Leu Gly Met
            180                 185                 190

Ala Val Leu Ala Ile Ser His Tyr Ala Met Met Lys Lys Met Gln Leu
        195                 200                 205

Pro Glu Leu Pro Lys Asp Ile Ser Tyr Lys Arg Tyr Ile Pro Glu Thr
    210                 215                 220

Leu Asn Lys Ser Ile Arg Gln Arg Asn Leu Leu Thr Arg Met Arg Ile
225                 230                 235                 240

Asn Asn Val Phe Lys Asp Phe Leu Lys Glu Phe Asn Asn Lys Thr Ile
                245                 250                 255

Cys Asp Ser Ser Val Ser Thr His Asp Leu Lys Val Lys Tyr Leu Ala
            260                 265                 270

Thr Leu Glu Thr Leu Thr Lys His Tyr Gly Ala Glu Ile Phe Glu Thr
        275                 280                 285

Ser Met Leu Leu Ile Ser Ser Glu Asn Glu Met Asn Trp Phe His Ser
    290                 295                 300

Asn Asp Gly Gly Asn Val Leu Tyr Tyr Glu Val Met Val Thr Gly Asn
305                 310                 315                 320

Leu Gly Ile Gln Trp Arg His Lys Pro Asn Val Val Ser Val Glu Lys
                325                 330                 335

Glu Lys Asn Lys Leu Lys Arg Lys Lys Leu Glu Asn Lys His Lys Lys
            340                 345                 350

Asp Glu Glu Lys Asn Lys Ile Arg Glu Glu Trp Asn Asn Phe Ser Tyr
        355                 360                 365

Phe Pro Glu Ile Thr His Ile Val Ile Lys Glu Ser Val Val Ser Ile
    370                 375                 380

Asn Lys Gln Asp Asn Lys Lys Met Glu Leu Lys Leu Ser Ser His Glu
385                 390                 395                 400

Glu Ala Leu Ser Phe Val Ser Leu Val Asp Gly Tyr Phe Arg Leu Thr
                405                 410                 415
```

-continued

Ala Asp Ala His His Tyr Leu Cys Thr Asp Val Ala Pro Pro Leu Ile
            420                 425                 430

Val His Asn Ile Gln Asn Gly Cys His Gly Pro Ile Cys Thr Glu Tyr
        435                 440                 445

Ala Ile Asn Lys Leu Arg Gln Glu Gly Ser Glu Glu Gly Met Tyr Val
    450                 455                 460

Leu Arg Trp Ser Cys Thr Asp Phe Asp Asn Ile Leu Met Thr Val Thr
465                 470                 475                 480

Cys Phe Glu Lys Ser Glu Gln Val Gln Gly Ala Gln Lys Gln Phe Lys
                485                 490                 495

Asn Phe Gln Ile Glu Val Gln Lys Gly Arg Tyr Ser Leu His Gly Ser
            500                 505                 510

Asp Arg Ser Phe Pro Ser Leu Gly Asp Leu Met Ser His Leu Lys Lys
        515                 520                 525

Gln Ile Leu Arg Thr Asp Asn Ile Ser Phe Met Leu Lys Arg Cys Cys
    530                 535                 540

Gln Pro Lys Pro Arg Glu Ile Ser Asn Leu Leu Val Ala Thr Lys Lys
545                 550                 555                 560

Ala Gln Glu Trp Gln Pro Val Tyr Pro Met Ser Gln Leu Ser Phe Asp
                565                 570                 575

Arg Ile Leu Lys Lys Asp Leu Val Gln Gly Glu His Leu Gly Arg Gly
            580                 585                 590

Thr Arg Thr His Ile Tyr Ser Gly Thr Leu Met Asp Tyr Lys Asp Asp
        595                 600                 605

Glu Gly Thr Ser Glu Glu Lys Lys Ile Lys Val Ile Leu Lys Val Leu
    610                 615                 620

Asp Pro Ser His Arg Asp Ile Ser Leu Ala Phe Phe Glu Ala Ala Ser
625                 630                 635                 640

Met Met Arg Gln Val Ser His Lys His Ile Val Tyr Leu Tyr Gly Val
                645                 650                 655

Cys Val Arg Asp Val Glu Asn Ile Met Val Glu Glu Phe Val Glu Gly
            660                 665                 670

Gly Pro Leu Asp Leu Phe Met His Arg Lys Ser Asp Val Leu Thr Thr
        675                 680                 685

Pro Trp Lys Phe Lys Val Ala Lys Gln Leu Ala Ser Ala Leu Ser Tyr
    690                 695                 700

Leu Glu Asp Lys Asp Leu Val His Gly Asn Val Cys Thr Lys Asn Leu
705                 710                 715                 720

Leu Leu Ala Arg Glu Gly Ile Asp Ser Glu Cys Gly Pro Phe Ile Lys
                725                 730                 735

Leu Ser Asp Pro Gly Ile Pro Ile Thr Val Leu Ser Arg Gln Glu Cys
            740                 745                 750

Ile Glu Arg Ile Pro Trp Ile Ala Pro Glu Cys Val Glu Asp Ser Lys
        755                 760                 765

Asn Leu Ser Val Ala Ala Asp Lys Trp Ser Phe Gly Thr Thr Leu Trp
    770                 775                 780

Glu Ile Cys Tyr Asn Gly Glu Ile Pro Leu Lys Asp Lys Thr Leu Ile
785                 790                 795                 800

Glu Lys Glu Arg Phe Tyr Glu Ser Arg Cys Arg Pro Val Thr Pro Ser
                805                 810                 815

Cys Lys Glu Leu Ala Asp Leu Met Thr Arg Cys Met Asn Tyr Asp Pro
            820                 825                 830

Asn Gln Arg Pro Phe Phe Arg Ala Ile Met Arg Asp Ile Asn Lys Leu

```
                    835                 840                 845
Glu Glu Gln Asn Pro Asp Ile Val Ser Glu Lys Lys Pro Ala Thr Glu
            850                 855                 860
Val Asp Pro Thr His Phe Glu Lys Arg Phe Leu Lys Arg Ile Arg Asp
865                 870                 875                 880
Leu Gly Glu Gly His Phe Gly Lys Val Glu Leu Cys Arg Tyr Asp Pro
                885                 890                 895
Glu Gly Asp Asn Thr Gly Glu Gln Val Ala Val Lys Ser Leu Lys Pro
            900                 905                 910
Glu Ser Gly Gly Asn His Ile Ala Asp Leu Lys Lys Glu Ile Glu Ile
        915                 920                 925
Leu Arg Asn Leu Tyr His Glu Asn Ile Val Lys Tyr Lys Gly Ile Cys
    930                 935                 940
Thr Glu Asp Gly Gly Asn Gly Ile Lys Leu Ile Met Glu Phe Leu Pro
945                 950                 955                 960
Ser Gly Ser Leu Lys Glu Tyr Leu Pro Lys Asn Lys Asn Lys Ile Asn
            965                 970                 975
Leu Lys Gln Gln Leu Lys Tyr Ala Val Gln Ile Cys Lys Gly Met Asp
        980                 985                 990
Tyr Leu Gly Ser Arg Gln Tyr  Val  His Arg Asp Leu Ala  Ala Arg Asn
        995                 1000                1005
Val Leu Val Glu Ser Glu  His  Gln Val Lys Ile  Gly  Asp Phe Gly
    1010                1015                1020
Leu Thr Lys Ala Ile Glu  Thr  Asp Lys Glu Tyr  Tyr  Thr Val Lys
    1025                1030                1035
Asp Asp Arg Asp Ser Pro  Val  Phe Trp Tyr Ala  Pro  Glu Cys Leu
    1040                1045                1050
Met Gln Ser Lys Phe Tyr  Ile  Ala Ser Asp Val  Trp  Ser Phe Gly
    1055                1060                1065
Val Thr Leu His Glu Leu  Leu  Thr Tyr Cys Asp  Ser  Asp Ser Ser
    1070                1075                1080
Pro Met Ala Leu Phe Leu  Lys  Met Ile Gly Pro  Thr  His Gly Gln
    1085                1090                1095
Met Thr Val Thr Arg Leu  Val  Asn Thr Leu Lys  Glu  Gly Lys Arg
    1100                1105                1110
Leu Pro Cys Pro Pro Asn  Cys  Pro Asp Glu Val  Tyr  Gln Leu Met
    1115                1120                1125
Arg Lys Cys Trp Glu Phe  Gln  Pro Ser Asn Arg  Thr  Ser Phe Gln
    1130                1135                1140
Asn Leu Ile Glu Gly Phe  Glu  Ala Leu Leu Lys
    1145                1150

<210> SEQ ID NO 5
<211> LENGTH: 5449
<212> TYPE: DNA
<213> ORGANISM: Homo sapiens

<400> SEQUENCE: 5
cacacaggaa ggagccgagt gggactttcc tctcgctgcc tcccggctct gcccgccctt     60
cgaaagtcca gggtccctgc cgctaggca  agttgcactc atggcacctc caagtgaaga    120
gacgcccctg atccctcagc gttcatgcag cctcttgtcc acggaggctg gtgccctgca    180
tgtgctgctg cccgctcggg gccccgggcc ccccagcgc  ctatctttct cctttgggga    240
ccacttggct gaggacctgt gcgtgcaggc tgccaaggcc agcggcatcc tgcctgtgta    300
```

```
ccactccctc tttgctctgg ccacggagga cctgtcctgc tggttccccc cgagccacat    360
cttctccgtg gaggatgcca gcacccaagt cctgctgtac aggattcgct tttacttccc    420
caattggttt gggctggaga agtgccaccg cttcgggcta cgcaaggatt tggccagtgc    480
tatccttgac ctgccagtcc tggagcacct ctttgcccag caccgcagtg acctggtgag    540
tgggcgcctc cccgtgggcc tcagtctcaa ggagcagggt gagtgtctca gcctggccgt    600
gttggacctg gcccggatgg cgcgagagca ggcccagcgg ccgggagagc tgctgaagac    660
tgtcagctac aaggcctgcc taccccccaag cctgcgcgac ctgatccagg cctgagctt    720 cgtgacgcgg aggcgtattc ggaggacggt gcgcagagcc ctgcgccgcg tggccgcctg    780
ccaggcagac cggcactcgc tcatggccaa gtacatcatg gacctggagc ggctggatcc    840
agccggggcc gccgagacct tccacgtggg cctccctggg gcccttggtg ccacgacgg    900 gctggggctg ctccgcgtgg ctggtgacgg cggcatcgcc tggacccagg gagaacagga    960
ggtcctccag cccttctgcg actttccaga aatcgtagac attagcatca agcaggcccc   1020
gcgcgttggc ccggccggag agcaccgcct ggtcactgtt accaggacag acaaccagat   1080
tttagaggcc gagttcccag gctgccgga ggctctgtcg ttcgtggcgc tcgtggacgg   1140
ctacttccgg ctgaccacgg actcccagca cttcttctgc aaggaggtgg caccgccgag   1200
gctgctggag gaagtggccg agcagtgcca cggccccatc actctggact ttgccatcaa   1260
caagctcaag actgggggct cacgtcctgg ctcctatgtt ctccgccgca gcccccagga   1320 cttttgacagc ttcctcctca ctgtctgtgt ccagaacccc cttggtcctg attataaggg   1380
ctgcctcatc cggcgcagcc ccacaggaac cttccttctg gttggcctca gccgaccca   1440 cagcagtctt cgagagctcc tggcaacctg ctgggatggg gggctgcacg tagatggggt   1500
ggcagtgacc ctcacttcct gctgtatccc cagacccaaa gaaaagtcca acctgatcgt   1560
ggtccagaga ggtcacagcc cacccacatc atccttggtt cagccccaat cccaatacca   1620
gctgagtcag atgacatttc acaagatccc tgctgacagc ctggagtggc atgagaacct   1680
gggccatggg tccttcacca agatttaccg gggctgtcgc catgaggtgg tggatgggga   1740
ggcccgaaag acagaggtgc tgctgaaggt catggatgcc aagcacaaga actgcatgga   1800
gtcattcctg gaagcagcga gcttgatgag ccaagtgtcg taccggcatc tcgtgctgct   1860
ccacggcgtg tgcatggctg gagacagcac catggtgcag gaatttgtac acctgggggc   1920
catagacatg tatctgcgaa aacgtggcca cctggtgcca gccagctgga agctgcaggt   1980
ggtcaaacag ctggcctacg ccctcaacta tctggaggac aaaggcctgc ccatggcaa   2040 tgtctctgcc cggaaggtgc tcctggctcg ggagggggct gatgggagcc cgcccttcat   2100
caagctgagt gaccctgggg tcagcccgc tgtgttaagc ctggagatgc tcaccgacag   2160
gatcccctgg gtggcccccg agtgtctccg ggaggcgcag acacttagct ggaagctga   2220 caagtggggc ttcggcgcca cggtctggga agtgtttagt ggcgtcacca tgcccatcag   2280
tgccctggat cctgctaaga aactccaatt ttatgaggac cggcagcagc tgccggcccc   2340
caagtggaca gagctggccc tgctgattca acagtgcatg gcctatgagc cggtccagag   2400
gccctccttc cgagccgtca ttcgtgacct caatagcctc atctcttcag actatgagct   2460
cctctcagac cccacacctg gtgccctggc acctcgtgat gggctgtgga atggtgccca   2520
gctctatgcc tgccaagacc ccacgatctt cgaggagaga cacctcaagt acatctcaca   2580
gctgggcaag ggcaactttg gcagcgtgga gctgtgccgc tatgaccgc taggcgacaa   2640
```

```
tacaggtgcc ctggtggccg tgaaacagct gcagcacagc gggccagacc agcagaggga   2700
ctttcagcgg gagattcaga tcctcaaagc actgcacagt gatttcattg tcaagtatcg   2760
tggtgtcagc tatggcccgg ccgccagag cctgcggctg gtcatggagt acctgcccag   2820
cggctgcttg cgcgacttcc tgcagcggca ccgcgcgcgc ctcgatgcca gccgcctcct   2880
tctctattcc tcgcagatct gcaagggcat ggagtacctg gctcccgcc gctgcgtgca   2940
ccgcgacctg gccgcccgaa acatcctcgt ggagagcgag gcacacgtca agatcgctga   3000
cttcggccta gctaagctgc tgccgcttga caaagactac tacgtggtcc gcgagccagg   3060
ccagagcccc attttctggt atgcccccga atccctctcg acaacatct tctctcgcca   3120
gtcagacgtc tggagcttcg gggtcgtcct gtacgagctc ttcacctact gcgacaaaag   3180
ctgcagcccc tcggccgagt tcctgcggat gatgggatgt gagcgggatg tccccgccct   3240
ctgccgcctc ttggaactgc tggaggaggg ccagaggctg ccggcgcctc ctgcctgccc   3300
tgctgaggtt cacgagctca tgaagctgtg ctgggcccct agcccacagg accggccatc   3360
attcagcgcc ctgggccccc agctggacat gctgtgagc ggaagccggg ggtgtgagac   3420
tcatgccttc actgctcacc cagagggcaa acaccactcc ctgtccttt catagctcct   3480
gccccgcagac ctctggatta ggtctctgtt gactggctgt gtgaccttag gcccggagct   3540
gcccctctct gggcctcaga ggccttatga gggtcctcta cttcaggaac accccccatga   3600
cattgcattt ggggggggctc ccgtggcctg tagaatagcc tgtggccttt gcaatttgtt   3660
aaggttcaag acagatgggc atatgtgtca gtggggctct ctgagtcctg gcccaaagaa   3720
gcaaggaacc aaatttaaga ctctcgcatc ttcccaaccc cttaagccct ggccccctga   3780
gtttcctttt ctgtctctct cttttattt ttttattt tatttttatt tttgagacag   3840
agcctcgctc tgttacccag ggtggagtgc agtggtgcga tctcggctca gtgcaacctc   3900
tgcttcccag gttcaagcga ttctcctgcc tcagcctccc gagtagctgg gattacaggt   3960
gtgcaccacc acacccggct aattttttt attttaata gagatgaggt ttcaccatga   4020
tggccaggct gatctcgaac tcctaacctc aagtgatcct cccacctcag cctcccaaag   4080
tgttggaata ataggcatga gccactgcac ccaggctttt ttttttttaa atttattatt   4140
attattttta agagacagga tcttgctacg ttgcccaggc tggtcttgaa ctcctgggct   4200
acagtgatcc tcctgcctta tcctcctaaa tagctgggac tacagcacct agttttgagt   4260
ttcctgtctt atttccaatg gggacattca tgtagctttt tttttttt ttttttgag   4320
acggagtctc gctctgtcgc ccaggctgga gtacagtggc gcaatctagg ctcactgcaa   4380
gctccgcctc ctgggttcac accattctct cgcctcagcc tccaagtag ctgggactac   4440
aggcgcccgc caccacccc ggctaatttt ttgtattttt agtagagacg gggtttcacc   4500
ttgttagcca ggatggtttc catctcctga cctcgtgatc tgcccgtctc ggcctcccaa   4560
agtgctggga ttacaggcat gagccactgc gccggccct catgtagctt taaatgtatg   4620
atctgacttc tgctccccga tctctgtttc tctggaggaa gccaaggaca agagcagttg   4680
ctgtggctgg gactctgcct tttaggggag cccgtgtatc tctttgggat cctgaaaggg   4740
ggcaggaaag gctggggtcc cagtccaccc taatggtatc tgagtgtcct agggcttcag   4800
ttttcccacc tgtccaatgg gacccttttct gtcctcaccc tacaaggggc acaaagggat   4860
gacaccaaac ctggcaggaa cttttcacgc aatcaaggga aggaaaggca ttcctggcag   4920
agggaacagc atgccaagcg tgagaaggct cagagtaagg aggttaagag cccaagtatt   4980
ggagcctaca gttttgcccc ttccatgcag tgtgacagtg ggcaagttcc tttccctctc   5040
```

```
tgggtctcag ttctgtcccc tgcaaaatgg tcagagctta cccccttggct gtgcagggtc    5100 aactttctga ctggtgagag ggattctcat gcaggttaag cttctgctgc tcctcctcac    5160
ctgcaaagct tttctgccac ttttgcctcc ttggaaaact cttatccatc tctcaaaact    5220
ccagctacca catccttgca gccttccctc atataccccc actactactg tagccctgtc    5280
cttccctcca gccccactct ggccctgggg ctggggaagt gtctgtgtcc agctgtctcc    5340
cctgacctca gggttccttg ggggctgggc tgaggcctca gtacagaggg ggctctggaa    5400
atgtttgttg actgaataaa ggaattcagt ggaaaaaaaa aaaaaaaa                  5449
```

<210> SEQ ID NO 6
<211> LENGTH: 5053
<212> TYPE: DNA
<213> ORGANISM: Homo sapiens

<400> SEQUENCE: 6

```
tgcagacagt gcgggcctgc gcccagtccc ggctgtcctc gccgcgaccc ctcctcagcc      60
ctgggcgcgc gcacgctggg gccccgcggg gctggccgcc tagcgagcct gccggtcgac     120
cccagccagc gcagcgacgg ggcgctgcct ggcccaggcg cacacggaag tgcgcttctc     180
tgaagtagct ttggaaagta gagaagaaaa tccagtttgc ttcttggaga cactggaca     240 gctgaataaa tgcagtatct aaatataaaa gaggactgca atgccatggc tttctgtgct     300
aaaatgagga gctccaagaa gactgaggtg aacctggagg cccctgagcc aggggtggaa     360
gtgatcttct atctgtcgga cagggagccc ctccggctgg gcagtggaga gtacacagca     420
gaggaactgt gcatcagggc tgcacaggca tgccgtatct ctcctctttg tcacaacctc     480
tttgccctgt atgacgagaa caccaagctc tggtatgctc caaatcgcac catcaccgtt     540
gatgacaaga tgtccctccg gctccactac cggatgaggt tctatttcac caattggcat     600
ggaaccaacg acaatgagca gtcagtgtgg cgtcattctc caaagaagca gaaaaatggc     660
tacgagaaaa aaaagattcc agatgcaacc cctctccttg atgccagctc actggagtat     720
ctgtttgctc agggacagta tgatttggtg aaatgcctgg ctcctattcg agaccccaag     780
accgagcagg atggacatga tattgagaac gagtgtcag ggatggctgt cctggccatc     840
tcacactatg ccatgatgaa gaagatgcag ttgccagaac tgcccaagga catcagctac     900
aagcgatata ttccagaaac attgaataag tccatcagac agaggaacct tctcaccagg     960
atgcggataa ataatgtttt caaggatttc ctaaaggaat ttaacaacaa gaccatttgt    1020
gacagcagcg tgtccacgca tgacctgaag gtgaaatact ggctaccttg gaaactttg    1080 acaaaacatt acggtgctga atatttgag acttccatgt tactgatttc atcagaaaat    1140
gagatgaatt ggtttcattc gaatgacggt ggaaacgttc tctactacga agtgatggtg    1200
actgggaatc ttggaatcca gtggaggcat aaaccaaatg ttgtttctgt tgaaaaggaa    1260
aaaaataaac tgaagcggaa aaaactggaa aataaacaca gaaggatgga ggagaaaaac    1320
aagatccggg aagagtggaa caattttctc tacttccctg aaatcactca cattgtaata    1380
aaggagtctg tggtcagcat taacaagcag gacaacaaga aatgtgaact gaagctctct    1440
tcccacgagg aggccttgtc ctttgtgtcc ctggtagatg ctacttccg gctcacagca    1500 gatgcccatc attacctctg caccgacgtg gccccccgt tgatcgtcca acatacag      1560 aatggctgtc atggtccaat ctgtacagaa tacgccatca ataaattgcg gcaagaagga    1620
agcgaggagg ggatgtacgt gctgaggtgg agctgcaccg actttgacaa catcctcatg    1680
```

-continued

| | |
|---|---|
| accgtcacct gctttgagaa gtctgagcag gtgcagggtg cccagaagca gttcaagaac | 1740 |
| tttcagatcg aggtgcagaa gggccgctac agtctgcacg gttcggaccg cagcttcccc | 1800 |
| agcttgggag acctcatgag ccacctcaag aagcagatcc tgcgcacgga taacatcagc | 1860 |
| ttcatgctaa aacgctgctg ccagcccaag ccccgagaaa tctccaacct gctggtggct | 1920 |
| actaagaaag cccaggagtg gcagcccgtc tacccatga gccagctgag tttcgatcgg | 1980 |
| atcctcaaga aggatctggt gcagggcgag caccttggga gaggcacgag aacacacatc | 2040 |
| tattctggga ccctgatgga ttacaaggat gacgaaggaa cttctgaaga gaagaagata | 2100 |
| aaagtgatcc tcaaagtctt agaccccagc cacagggata tttccctggc cttcttcgag | 2160 |
| gcagccagca tgatgagaca ggtctcccac aaacacatcg tgtacctcta tggcgtctgt | 2220 |
| gtccgcgacg tggagaatat catggtggaa gagtttgtgg aagggggtcc tctggatctc | 2280 |
| ttcatgcacc ggaaaagcga tgtccttacc acaccatgga aattcaaagt tgccaaacag | 2340 |
| ctggccagtg ccctgagcta cttggaggat aaagacctgg tccatggaaa tgtgtgtact | 2400 |
| aaaaacctcc tcctggcccg tgagggcatc gacagtgagt gtggcccatt catcaagctc | 2460 |
| agtgaccccg gcatccccat tacggtgctg tctaggcaag aatgcattga acgaatccca | 2520 |
| tggattgctc ctgagtgtgt tgaggactcc aagaacctga gtgtggctgc tgacaagtgg | 2580 |
| agctttggaa ccacgctctg ggaaatctgc tacaatggcg agatcccctt gaaagacaag | 2640 |
| acgctgattg agaaagagag attctatgaa agccggtgca ggccagtgac accatcatgt | 2700 |
| aaggagctgg ctgacctcat gacccgctgc atgaactatg accccaatca gaggcctttc | 2760 |
| ttccgagcca tcatgagaga cattaataag cttgaagagc agaatccaga tattgtttca | 2820 |
| gaaaaaaaac cagcaactga agtggacccc acacattttg aaaagcgctt cctaaagagg | 2880 |
| atccgtgact gggagagggg ccactttggg aaggttgagc tctgcaggta tgaccccgaa | 2940 |
| ggggacaata caggggagca ggtggctgtt aaatctctga gcctgagagt ggaggtaaac | 3000 |
| cacatagctg atctgaaaaa ggaaatcgag atcttaagga acctctatca tgagaacatt | 3060 |
| gtgaagtaca aggaatctg cacagaagac ggaggaaatg gtattaagct catcatggaa | 3120 |
| tttctgcctt cgggaagcct taaggaatat cttccaaaga ataagaacaa aataaacctc | 3180 |
| aaacagcagc taaatatgc cgttcagatt tgtaagggga tggactattt gggttctcgg | 3240 |
| caatacgttc accgggactt ggcagcaaga aatgtccttg ttgagagtga acaccaagtg | 3300 |
| aaaattggag acttcggttt aaccaaagca attgaaaccg ataaggagta ttacaccgtc | 3360 |
| aaggatgacc gggacagccc tgtgttttgg tatgctccag aatgtttaat gcaatctaaa | 3420 |
| ttttatattg cctctgacgt ctggtctttt ggagtcactc tgcatgagct gctgacttac | 3480 |
| tgtgattcag attctagtcc catggctttg ttcctgaaaa tgataggccc aacccatggc | 3540 |
| cagatgacag tcacaagact tgtgaatacg ttaaaagaag gaaaacgcct gccgtgccca | 3600 |
| cctaactgtc cagatgaggt ttatcaactt atgaggaaat gctgggaatt ccaaccatcc | 3660 |
| aatcggacaa gctttcagaa ccttattgaa ggatttgaag cacttttaaa ataagaagca | 3720 |
| tgaataacat ttaaattcca cagattatca agtccttctc ctgcaacaaa tgcccaagtc | 3780 |
| attttttaaa aatttctaat gaaagaagtt tgtgttctgt ccaaaaagtc actgaactca | 3840 |
| tacttcagta catatacatg tataaggcac actgtagtgc ttaatatgtg taaggacttc | 3900 |
| ctctttaaat ttggtaccag taacttagtg acacataatg acaaccaaaa tatttgaaag | 3960 |
| cacttaagca ctcctccttg tggaaagaat ataccaccat ttcatctggc tagttccacca | 4020 |
| tcacaactgc attaccaaaa ggggatttt gaaaacgagg agttgaccaa aataatatct | 4080 |

-continued

```
gaagatgatt gcttttccct gctgccagct gatctgaaat gttttgctgg cacattaatc    4140
atagataaag aaagattgat ggacttagcc ctcaaatttc agtatctata cagtactaga    4200
ccatgcattc ttaaaatatt agataccagg tagtatatat tgtttctgta caaaaatgac    4260
tgtattctct caccagtagg acttaaactt tgtttctcca gtggcttagc tcctgttcct    4320
ttgggtgatc actagcaccc attttgaga aagctggttc tacatggggg gatagctgtg    4380
gaatagataa tttgctgcat gttaattctc aagaactaag cctgtgccag tgctttccta    4440
agcagtatac ctttaatcag aactcattcc cagaacctgg atgctattac acatgctttt    4500
aagaaacgtc aatgtatatc cttttataac tctaccactt tggggcaagc tattccagca    4560
ctggttttga atgctgtatg caaccagtct gaataccaca tacgctgcac tgttcttaga    4620
gggtttccat acttaccacc gatctacaag ggttgatccc tgttttacc atcaatcatc     4680 accctgtggt gcaacacttg aaagacccgg ctagaggcac tatggacttc aggatccact    4740
agacagtttt cagtttgctt ggaggtagct gggtaatcaa aaatgtttag tcattgattc    4800
aatgtgaacg attacggtct ttatgaccaa gagtctgaaa atcttttgt tatgctgttt     4860 agtattcgtt tgatattgtt acttttcacc tgttgagccc aaattcagga ttggttcagt    4920
ggcagcaatg aagttgccat ttaaatttgt tcatagccta catcaccaag gtctctgtgt    4980
caaacctgtg gccactctat atgcactttg tttactcttt atacaaataa atatactaaa    5040
gactttacat gca                                                       5053

<210> SEQ ID NO 7
<211> LENGTH: 21
<212> TYPE: DNA
<213> ORGANISM: artificial
<220> FEATURE:
<223> OTHER INFORMATION: JAK1_Seq_Exon14F

<400> SEQUENCE: 7
ctggcctgag acattcctat g                                               21

<210> SEQ ID NO 8
<211> LENGTH: 26
<212> TYPE: DNA
<213> ORGANISM: artificial
<220> FEATURE:
<223> OTHER INFORMATION: JAK1_ Seq_Exon14R

<400> SEQUENCE: 8
tgaaagagaa cacacttact ctccac                                          26

<210> SEQ ID NO 9
<211> LENGTH: 23
<212> TYPE: DNA
<213> ORGANISM: artificial
<220> FEATURE:
<223> OTHER INFORMATION: JAK1_HRM_Exon14F

<400> SEQUENCE: 9
gcatgatgag acaggtctcc cac                                             23

<210> SEQ ID NO 10
<211> LENGTH: 24
<212> TYPE: DNA
<213> ORGANISM: artificial
<220> FEATURE:
<223> OTHER INFORMATION: JAK1_HRM_Exon14R
```

```
<400> SEQUENCE: 10
gagaacacac ttactctcca cgtc                                          24

<210> SEQ ID NO 11
<211> LENGTH: 21
<212> TYPE: DNA
<213> ORGANISM: artificial
<220> FEATURE:
<223> OTHER INFORMATION: JAK2_Seq_Exon12F

<400> SEQUENCE: 11
cagcaagtat gatgagcaag c                                             21

<210> SEQ ID NO 12
<211> LENGTH: 20
<212> TYPE: DNA
<213> ORGANISM: artificial
<220> FEATURE:
<223> OTHER INFORMATION: JAK2_Seq_Exon12R

<400> SEQUENCE: 12
acagatgctc tgagaaaggc                                               20

<210> SEQ ID NO 13
<211> LENGTH: 20
<212> TYPE: DNA
<213> ORGANISM: artificial
<220> FEATURE:
<223> OTHER INFORMATION: JAK2_HRM_Exon12F

<400> SEQUENCE: 13
gctttctcac aagcatttgg                                               20

<210> SEQ ID NO 14
<211> LENGTH: 20
<212> TYPE: DNA
<213> ORGANISM: artificial
<220> FEATURE:
<223> OTHER INFORMATION: JAK2_HRM_Exon12R

<400> SEQUENCE: 14
ggcattagaa agcctgtagt                                               20

<210> SEQ ID NO 15
<211> LENGTH: 21
<212> TYPE: DNA
<213> ORGANISM: artificial
<220> FEATURE:
<223> OTHER INFORMATION: JAK3_Seq_Exon12F

<400> SEQUENCE: 15
gcaggtctgt gagcacaaaa t                                             21

<210> SEQ ID NO 16
<211> LENGTH: 19
<212> TYPE: DNA
<213> ORGANISM: artificial
<220> FEATURE:
<223> OTHER INFORMATION: JAK3_Seq_Exon12R

<400> SEQUENCE: 16
actgtctcca gccatgcac                                                19

<210> SEQ ID NO 17
<211> LENGTH: 19
```

```
<212> TYPE: DNA
<213> ORGANISM: artificial
<220> FEATURE:
<223> OTHER INFORMATION: JAK3_HRM_Exon12F

<400> SEQUENCE: 17
ccaccttccc cagtcattc                                              19

<210> SEQ ID NO 18
<211> LENGTH: 21
<212> TYPE: DNA
<213> ORGANISM: artificial
<220> FEATURE:
<223> OTHER INFORMATION: JAK3_HRM_Exon12R

<400> SEQUENCE: 18
gagatgccgg tacgacactt g                                           21
```